US012630575B2

(12) United States Patent
Moon et al.

(10) Patent No.: US 12,630,575 B2
(45) Date of Patent: May 19, 2026

(54) ORGANOMETALLIC COMPOUND AND ORGANIC ELECTROLUMINESCENT DEVICE INCLUDING THE SAME

(71) Applicants: LG DISPLAY CO., LTD., Seoul (KR); LT MATERIALS CO., LTD., Yongin-si (KR)

(72) Inventors: Jaemin Moon, Seoul (KR); Inbum Song, Seoul (KR); Dohan Kim, Goyang-si (KR); Sungjin Park, Paju-si (KR); Yong Woo Kim, Osan-si (KR); Seokhyeon Yu, Osan-si (KR)

(73) Assignees: LG DISPLAY CO., LTD., Seoul (KR); LT MATERIALS CO., LTD., Yongin-si (KR)

( * ) Notice: Subject to any disclaimer, the term of this patent is extended or adjusted under 35 U.S.C. 154(b) by 906 days.

(21) Appl. No.: 17/825,866

(22) Filed: May 26, 2022

(65) Prior Publication Data

US 2023/0002427 A1 Jan. 5, 2023

(30) Foreign Application Priority Data

May 27, 2021 (KR) ........................ 10-2021-0068619
Apr. 26, 2022 (KR) ........................ 10-2022-0051599

(51) Int. Cl.
*H01L 51/50* (2006.01)
*C07C 211/54* (2006.01)
(Continued)

(52) U.S. Cl.
CPC ........ *C07F 15/0033* (2013.01); *C07C 211/54* (2013.01); *C07D 209/82* (2013.01);
(Continued)

(58) Field of Classification Search
None
See application file for complete search history.

(56) References Cited

U.S. PATENT DOCUMENTS

| | | | | |
|---|---|---|---|---|
| 10,686,146 B2 | 6/2020 | Yen et al. | | |
| 2003/0170491 A1* | 9/2003 | Liao | H05B 33/00 428/690 | |

(Continued)

FOREIGN PATENT DOCUMENTS

| | | | | |
|---|---|---|---|---|
| CN | 107501336 | * 12/2017 | H01L 51/54 | |
| CN | 107501336 A | 12/2017 | | |

(Continued)

OTHER PUBLICATIONS

Jiang et. al., Highly efficient red iridium(III) complexes cyclometalated by 4-phenylthieno[3,2-c]quinoline ligands for phosphorescent OLEDs with external quantum efficiencies over 20%\, 2017; J. Mater. Chem. C, 2017, 10220-10224 (Year: 2017).*

(Continued)

*Primary Examiner* — Gregory D Clark
(74) *Attorney, Agent, or Firm* — Birch, Stewart, Kolasch & Birch, LLP

(57) ABSTRACT

Disclosed is an organometallic compound represented by a following Chemical Formula I, wherein the compound is a metal complex including a central coordination metal and a main ligand binding thereto, wherein the main ligand has a structure in which a fused ring is further introduced into 2-phenylquinoline. When the organometallic compound is used as dopant of a light-emitting layer of an organic electroluminescent device, rigidity is imparted to the organometallic compound molecule such that a full width at half maximum (FWHM) is narrow and thus color purity is improved. Further, a non-luminescent recombination process is reduced such that luminous efficiency and lifespan of the organic electroluminescent device are improved. Chemical Formula I is shown below:

(Continued)

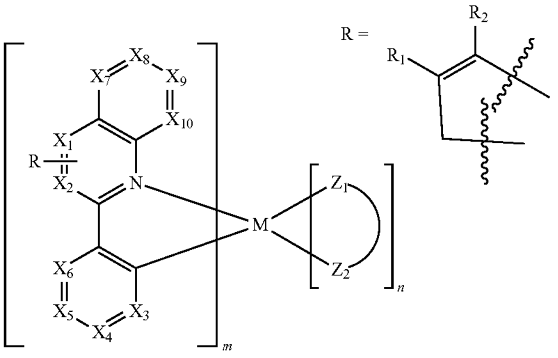

16 Claims, 3 Drawing Sheets

(51) Int. Cl.

| | |
|---|---|
| ***C07D 209/82*** | (2006.01) |
| ***C07D 235/18*** | (2006.01) |
| ***C07F 1/02*** | (2006.01) |
| ***C07F 15/00*** | (2006.01) |
| ***H10K 85/30*** | (2023.01) |
| ***H10K 85/60*** | (2023.01) |
| *H10K 50/12* | (2023.01) |
| *H10K 50/13* | (2023.01) |
| *H10K 50/16* | (2023.01) |
| *H10K 50/165* | (2023.01) |
| *H10K 50/17* | (2023.01) |
| *H10K 71/16* | (2023.01) |
| *H10K 77/10* | (2023.01) |

(52) U.S. Cl.

CPC .............. *C07D 235/18* (2013.01); *C07F 1/02* (2013.01); *H10K 85/30* (2023.02); *H10K 85/342* (2023.02); *H10K 85/631* (2023.02); *H10K 85/657* (2023.02); *H10K 50/12* (2023.02); *H10K 50/13* (2023.02); *H10K 50/16* (2023.02); *H10K 50/165* (2023.02); *H10K 50/17* (2023.02); *H10K 50/171* (2023.02); *H10K 71/164* (2023.02); *H10K 77/111* (2023.02)

(56) References Cited

U.S. PATENT DOCUMENTS

| | | | | |
|---|---|---|---|---|
| 2012/0018717 | A1* | 1/2012 | Kim ..................... | C07D 209/94 546/276.7 |
| 2013/0033172 | A1 | 2/2013 | Huang et al. | |
| 2015/0287933 | A1 | 10/2015 | Kottas et al. | |
| 2018/0013077 | A1 | 1/2018 | Boudreault et al. | |
| 2018/0151812 | A1* | 5/2018 | Peng ...................... | H10K 85/30 |
| 2019/0207123 | A1* | 7/2019 | Yoon .................... | H10K 85/611 |
| 2020/0266365 | A1 | 8/2020 | Kim et al. | |
| 2021/0151696 | A1 | 5/2021 | Lee et al. | |

FOREIGN PATENT DOCUMENTS

| | | | |
|---|---|---|---|
| CN | 108276452 | A | 7/2018 |
| CN | 110642892 | A | 1/2020 |
| CN | 110642893 | A | 1/2020 |
| CN | 110669077 | A | 1/2020 |
| CN | 112794859 | A | 5/2021 |
| KR | 10-2014-0052757 | A | 5/2014 |
| TW | 201829438 | A | 8/2018 |

OTHER PUBLICATIONS

Jiang et al., "Highly Efficient Red Iridium(III) Complexes Cyclometalated by 4-Phenylthieno[3,2-c]quinoline Ligands for Phosphorescent OLEDs with External Quantum Efficiencies over 20%," Journal of Materials Chemistry C., vol. 39, 2017, pp. 1020-1022.

Indian Office Action for Indian Application No. 202214030512, dated Jun. 5, 2025, with English translation.

* cited by examiner

ORGANOMETALLIC COMPOUND AND ORGANIC ELECTROLUMINESCENT DEVICE INCLUDING THE SAME

CROSS-REFERENCE TO RELATED APPLICATION

This application claims priority under 35 U.S.C. § 119 to Korean Patent Application Nos. 10-2021-0068619 filed on May 27, 2021 and 10-2022-0051599 filed on Apr. 26, 2022 in the Republic of Korea, the entire contents of all these applications are herein incorporated by reference into the present application.

BACKGROUND OF THE INVENTION

Field of the Invention

The present disclosure relates to an organometallic compound, and more particularly, to an organometallic compound having phosphorescent properties and an organic electroluminescent device including the same.

Discussion of Related Art

Display devices are important to several fields, and there continues to be a demand for improved performance. One example of such display device is an organic light emitting display device including an organic electroluminescent device, such as an organic light emitting diode: OLED display.

In the organic electroluminescent device, when electric charges are injected into a light-emitting layer formed between a positive electrode and a negative electrode, an electron and a hole are recombined with each other in the light-emitting layer to form an exciton and thus energy of the exciton is converted to light. Thus, the organic electroluminescent device emits the light. Compared to conventional display devices, the organic electroluminescent device can operate at a low voltage, consume relatively little power, render excellent colors, and can be used in a variety of ways because a flexible substrate can be applied thereto. Further, the size of the organic electroluminescent device can be freely adjustable.

SUMMARY OF THE INVENTION

The organic electroluminescent device (OLED) according to the invention has superior viewing angle and contrast ratio compared to a liquid crystal display (LCD), and is lightweight and is ultra-thin because the OLED does not require a backlight. The organic electroluminescent device includes a plurality of organic layers between a negative electrode (electron injection electrode; cathode) and a positive electrode (hole injection electrode; anode). The plurality of organic layers can include a hole injection layer, a hole transport layer, a hole transport auxiliary layer, an electron blocking layer, and a light-emitting layer, an electron transport layer, etc.

In this organic electroluminescent device structure, when a voltage is applied across the two electrodes, electrons and holes are injected from the negative and positive electrodes, respectively, into the light emitting layer and thus excitons are generated in the light-emitting layer and then fall to a ground state to emit light.

Organic materials used in the organic electroluminescent device can be largely classified into light-emitting materials and charge-transporting materials. The light-emitting material is an important factor determining luminous efficiency of the organic electroluminescent device. The luminescent material must have high quantum efficiency, excellent electon and hole mobility, and must exist uniformly and stably in the light-emitting layer. The light-emitting materials can be classified into light-emitting materials emitting light of blue, red, and green colors based on colors of the light. A color-generating material can include a host and dopants to increase the color purity and luminous efficiency through energy transfer.

In the organic electroluminescent device, low driving voltage, high efficiency, and long life is continuously required. In addition, in the organic electroluminescent device, demand for a light-emitting material that can render high-purity colors covering a wide CIE color coordinate range is increasing. In particular, in a white organic light-emitting diode using a color filter, there is a greater need for a light-emitting material that exhibits excellent luminous efficiency and renders high-purity color.

However, as the color purity become higher (a CIE color coordinate X value increases), visibility decreases. Thus, there is a problem that it is difficult to obtain high luminous efficiency with the same internal quantum efficiency. Thus, it is required to develop a phosphorescent light emitting material that can realize a low driving voltage, high efficiency, long lifespan, and excellent color purity.

Therefore, a purpose of the present disclosure is to provide an organometallic compound capable of realizing high color purity and high luminance of the organic electroluminescent device, and lowering driving voltage of the organic electroluminescent device, and improving luminous efficiency and lifespan of the organic electroluminescent device, and to provide the organic electroluminescent device in which an organic light-emitting layer contains the same.

Purposes of the present disclosure are not limited to the above-mentioned purpose. Other purposes and advantages of the present disclosure that are not mentioned can be understood based on following descriptions, and can be more clearly understood based on embodiments of the present disclosure. Further, it will be easily understood that the purposes and advantages of the present disclosure can be realized using means shown in the claims and combinations thereof.

In order to achieve the above purpose, the present disclosure provides an organometallic compound having a novel structure represented by a following Chemical Formula I and an organic electroluminescent device in which a light-emitting layer contains the same as dopants thereof.

Chemical Formula I:

Chemical Formula I

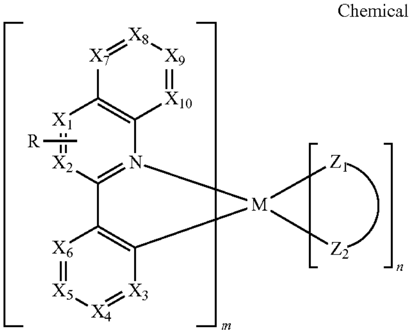

-continued

R =

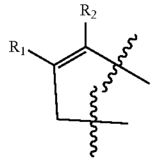

where in the Chemical Formula I,

M represents a central coordination metal, and includes one selected from a group consisting of molybdenum (Mo), tungsten (W), rhenium (Re), ruthenium (Ru), osmium (Os), rhodium (Rh), iridium (Ir), palladium (Pd), platinum (Pt) and gold (Au);

R represents a fused ring connected to $X_1$ and $X_2$;

each of $R_1$ and $R_2$ independently represents one selected from a group consisting of hydrogen, deuterium, halogen, a hydroxyl group, a cyano group, a nitro group, an amidino group, a hydrazine group, a hydrazone group, a substituted or unsubstituted C1-C20 alkyl group, a substituted or unsubstituted C3-C20 cycloalkyl group, a substituted or unsubstituted C1-C20 heteroalkyl group, a substituted or unsubstituted C7-C20 arylalkyl group, a substituted or unsubstituted C1-C20 alkenyl group, a substituted or unsubstituted C3-C20 cycloalkenyl group, a substituted or unsubstituted C1-C20 heteroalkenyl group, alkynyl group, a substitute or unsubstituted C6-C30 aryl group, a substituted or unsubstituted C3-C30 heteroaryl group, a alkoxy group, an amino group, a silyl group, an acyl group, a carbonyl group, a carboxylic acid group, an ester group, a nitrile group, an isonitrile group, a sulfanyl group, a sulfinyl group, a sulfonyl group, and a phosphino group;

Y represents one selected from a group consisting of $BR_3$, $CR_3R_4$, C═O, $CNR_3$, $SiR_3R_4$, $NR_3$, $PR_3$, $AsR_3$, $SbR_3$, $P(O)R_3$, $P(S)R_3$, $P(Se)R_3$, $As(O)R_3$, $As(S)R_3$, $As(Se)R_3$, $Sb(O)R_3$, $Sb(S)R_3$, $Sb(Se)R_3$, O, S, Se, Te, SO, $SO_2$, SeO, $SeO_2$, TeO and $TeO_2$;

each of $R_3$ and $R_4$ independently represents one selected from a group consisting of hydrogen, deuterium, halogen, a hydroxyl group, a cyano group, a nitro group, an amidino group, a hydrazine group, a hydrazone group, a substituted or unsubstituted C1-C20 alkyl group, a substituted or unsubstituted C3-C20 cycloalkyl group, a substituted or unsubstituted C1-C20 heteroalkyl group, a substituted or unsubstituted C7-C20 arylalkyl group, a substituted or unsubstituted C1-C20 alkenyl group, a substituted or unsubstituted C3-C20 cycloalkenyl group, a substituted Or an unsubstituted C1-C20 heteroalkenyl group, an alkynyl group, a substituted or unsubstituted C6-C30 aryl group, a substituted or unsubstituted C3-C30 heteroaryl group, an alkoxy group, an amino group, a silyl group, an acyl group, a carbonyl group, a carboxylic acid group, an ester group, a nitrile group, an isonitrile group, a sulfanyl group, a sulfinyl group, a sulfonyl group, and a phosphino group;

each of $X_3$ to $X_6$ independently represents one selected from $CR_5$ and N;

adjacent substituents of $X_3$ to $X_6$ fuse with each other to form a ring, and the ring includes a C5-C6 carbon ring or a heterocyclic ring;

each of $X_7$ to $X_{10}$ independently represents one selected from $CR_6$ and N;

each of $R_5$ and $R_6$ independently represents one selected from a group consisting of hydrogen, deuterium, halogen, a hydroxyl group, a cyano group, a nitro group, an amidino group, a hydrazine group, a hydrazone group, a substituted or unsubstituted C1-C20 alkyl group, a substituted or unsubstituted A cyclic C3-C20 cycloalkyl group, a substituted or unsubstituted C1-C20 heteroalkyl group, a substituted or unsubstituted C7-C20 arylalkyl group, a substituted or unsubstituted C1-C20 alkenyl group, a substituted or unsubstituted C3-C20 cycloalkenyl group, a substituted or unsubstituted C1-C20 heteroalkenyl group, an alkynyl group, a substituted or unsubstituted C6-C30 aryl group, a substituted or unsubstituted C3-C30 heteroaryl group, an alkoxy group, an amino group, a silyl group, an acyl group, a carbonyl group, a carboxylic acid group, an ester group, a nitrile group, an isonitrile group, a sulfanyl group, a sulfinyl group, a sulfonyl group and a phosphino group;

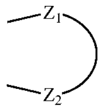

is a bidentate ligand;

m is an integer of 1, 2 or 3, n is an integer of 0, 1 or 2, and m+n is a oxidation number of the metal M.

When the organometallic compound according to the present disclosure is used as the dopant of the light-emitting layer of the organic electroluminescent device, the driving voltage of the organic electroluminescent device can be lowered and the luminous efficiency and lifespan characteristics of the organic electroluminescent device can be improved.

In addition, when the organometallic compound according to the present disclosure is used as the dopant of the light-emitting layer of the organic electroluminesce t device, the color purity of the organic electroluminescent device can be improved, and high color purity and high luminance of the device can be realized.

Effects of the present disclosure are not limited to the above-mentioned effects, and other effects as not mentioned will be clearly understood by those skilled in the art from following descriptions. All components of each light emitting display apparatus according to all embodiments of the present disclosure are operatively coupled and configured.

DETAILED DESCRIPTION OF THE EMBODIMENTS

Figure 1:
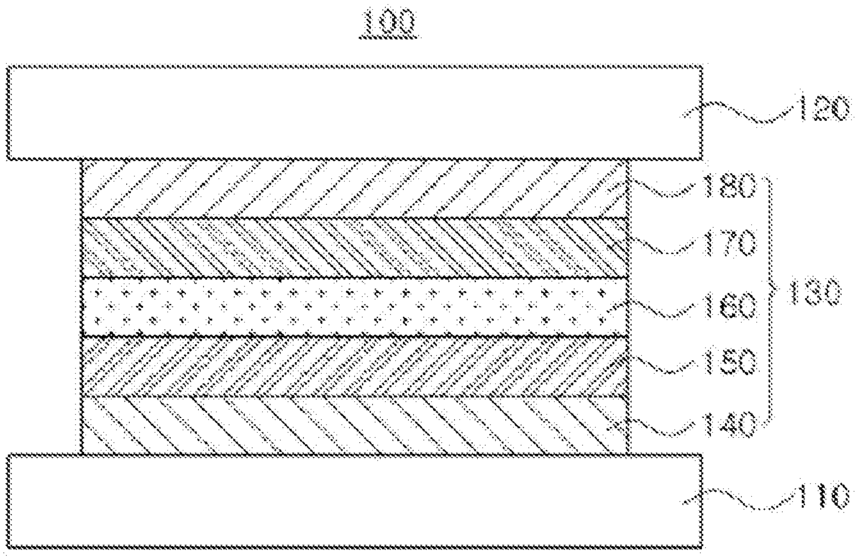
FIG. 1 is a cross-sectional view schematically showing an organic electroluminescent device to which an organometallic compound according to some embodiments of the present disclosure is applied to a light-emitting layer.

Advantages and features of the present disclosure, and the methods of achieving the advantages and features will become apparent with reference to embodiments described later in detail together with the accompanying drawings. However, the present disclosure is not limited to the embodiments as disclosed below, but can be implemented in various forms. Thus, these embodiments are set forth as examples only, and not intended to be limiting.

A shape, a size, a ratio, an angle, a number, etc. disclosed in the drawings for describing the embodiments of the present disclosure are exemplary, and the present disclosure is not limited thereto. The same reference numerals refer to the same elements herein. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure can be practiced without these specific details. In other instances, well-known methods, procedures, components, and circuits have not been described in detail so as not to unnecessarily obscure aspects of the present disclosure.

The terminology used herein is directed to the purpose of describing particular embodiments only and is not intended to be limiting of the present disclosure. As used herein, the singular constitutes "a" and "an" are intended to include the plural constitutes as well, unless the context clearly indicates otherwise. It will be further understood that the terms "comprise", "including", "include", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements can modify the entire list of elements and may not modify the individual elements of the list. In interpretation of numerical values, an error or tolerance therein can occur even when there is no explicit description thereof.

In addition, it will also be understood that when a first element or layer is referred to as being present "on" a second element or layer, the first element can be disposed directly on the second element or can be disposed indirectly on the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers can be present. In addition, it will also be understood that when an element or layer is referred to as being "between" two elements or layers, it can be the only element or layer between the two elements or layers, or one or more intervening elements or layers can also be present.

Further, as used herein, when a layer, film, region, plate, or the like is disposed "on" or "on a top" of another layer, film, region, plate, or the like, the former can directly contact the latter or still another layer, film, region, plate, or the like can be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former can directly contact the latter or still another layer, film, region, plate, or the like can be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

In descriptions of temporal relationships, for example, temporal precedent relationships between two events such as "after", "subsequent to", "before", etc., another event can occur therebetween unless "directly after", "directly subsequent" or "directly before" is not indicated.

It will be understood that, although the terms "first", "second", "third", and so on can be used herein to describe various elements, components, regions, layers and/or sections, these elements, components, regions, layers and/or sections should not be limited by these terms. These terms are used to distinguish one element, component, region, layer or section from another element, component, region, layer or section, and may not define order or sequence. Thus, a first element, component, region, layer or section described below could be termed a second element, component, region, layer or section, without departing from the spirit and scope of the present disclosure.

The features of the various embodiments of the present disclosure can be partially or entirely combined with each other, and can be technically associated with each other or operate with each other. The embodiments can be implemented independently of each other and can be implemented together in an association relationship.

In interpreting a numerical value, the value is interpreted as including an error range unless there is no separate explicit description thereof.

It will be understood that when an element or layer is referred to as being "connected to", or "coupled to" another element or layer, it can be directly on, connected to, or coupled to the other element or layer, or one or more intervening elements or layers can be present. In addition, it will also be understood that when an element or layer is referred to as being "between" two elements or layers, it can be the only element or layer between the two elements or layers, or one or more intervening elements or layers can also be present.

The features of the various embodiments of the present disclosure can be partially or entirely combined with each other, and can be technically associated with each other or operate with each other. The embodiments can be implemented independently of each other and can be implemented together in an association relationship.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, a term "hetero" means that one or more of carbon atoms constituting an aromatic or alicyclic ring, for example, 1 to 5 carbon atoms are substituted with one or more heteroatoms selected from a group consisting of N, O, S, and combinations thereof.

Hereinafter, a structure and preparation examples of an organometallic compound according to the present disclosure and an organic electroluminescent device including the same will be described.

The organometallic compound according to one implementation of the present disclosure includes a central coordination metal, and a main ligand bonded to the central coordination metal, wherein the main ligand includes a structure in which a 5-membered sed ring is additionally introduced to a basic framework structure of 2-phenylquinoline. The 5-membered fused ring additionally introduced to 2-phenylquinoline is denoted by R in the structure of Chemical Formula I of the present disclosure.

When the organometallic compound of the above structure is used as dopant of a light-emitting layer of an organic electroluminescent device, rigidity is impaired to the organometallic compound molecule such that a full width at half maximum (FWHM) is narrow and thus color purity is improved. Further, a non-luminescent recombination process is reduced such that luminous efficiency and lifespan of the organic electroluminescent device are improved.

The organometallic compound according to the present disclosure having the above characteristics can be represented by a following Chemical Formula I:

Chemical Formula I

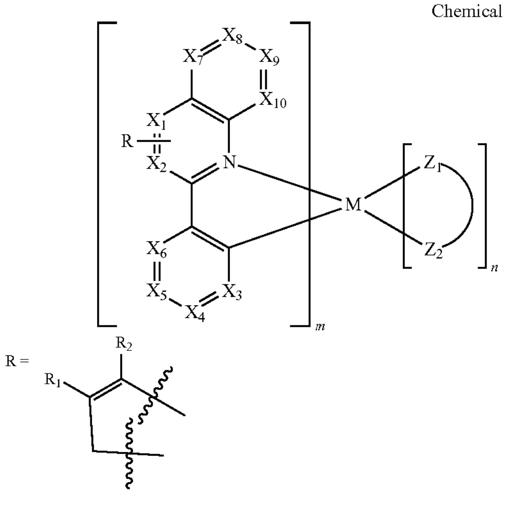

where in the Chemical Formula I,

M can represent a central coordination metal, and includes one selected from a group consisting of molybdenum (Mo), tungsten (W), rhenium (Re), ruthenium (Ru), osmium (Os), rhodium (Rh), iridium (Ir), palladium (Pd), platinum (Pt) and gold (Au);

R can represent a fused ring connected to $X_1$ and $X_2$;

each of $R_1$ and $R_2$ can independently represent one selected from a group consisting of hydrogen, deuterium, halogen, a hydroxyl group, a cyano group, a nitro group, an amidino group, a hydrazine group, a hydrazone group, a substituted or unsubstituted C1-C20 alkyl group, a substituted or unsubstituted C3-C20 cycloalkyl group, a substituted or unsubstituted C1-C20 heteroalkyl group, a substituted or unsubstituted C7-C20 arylalkyl group, a substituted or unsubstituted C1-C20 alkenyl group, a substituted or unsubstituted C3-C20 cycloalkenyl group, a substituted or unsubstituted C1-C20 heteroalkenyl group, alkynyl group, a substituted or unsubstituted C6-C30 aryl group, a substituted or unsubstituted C3-C30 heteroaryl group, an alkoxy group, an amino group, a silyl group, an acyl group, a carbonyl group, a carboxylic acid group, an ester group, a nitrile group, an isonitrile group, a sulfanyl group, a sulfinyl group, a sulfonyl group, and a phosphino group;

Y can represent one selected from a group consisting of $BR_3$, $CR_3R_4$, C═O, $CNR_3$, $SiR_3R_4$, $NR_3$, $PR_3$, $AsR_3$, $SbR_3$, $P(O)R_3$, $P(S)R_3$, $P(Se)R_3$, $As(O)R_3$, $As(S)R_3$, $As(Se)R_3$, $Sb(O)R_3$, $Sb(S)R_3$, $Sb(Se)R_3$, O, S, Se, Te, SO, $SO_2$, SeO, $SeO_2$, TeO and $TeO_2$;

each of $R_3$ and $R_4$ can independently represent one selected from a group consisting of hydrogen, deuterium, halogen, a hydroxyl group, a cyano group, a nitro group, an amidino group, a hydrazine group, a hydrazone group, a substituted or unsubstituted C1-C20 alkyl group, a substituted or unsubstituted C3-C20 cycloalkyl group, a substituted or unsubstituted C1-C20 heteroalkyl group, a substituted or unsubstituted C7-C20 arylalkyl group, a substituted or unsubstituted C1-C20 alkenyl group, a substituted or unsubstituted C3-C20 cycloalkenyl group, a substituted Or an unsubstituted C1-C20 heteroalkenyl group, an alkynyl group, a substituted or unsubstituted C6-C30 aryl group, a substituted or unsubstituted C3-C30 heteroaryl group, an alkoxy group, an amino group, a silyl group, an acyl group, a carbonyl group, a carboxylic acid group, an ester group, a nitrile group, an isonitrile group, a sulfanyl group, a sulfinyl group, a sulfonyl group, and a phosphino group;

each of $X_3$ to $X_6$ can independently represent one selected from $CR_5$ an N; adjacent substituents of $X_3$ to $X_6$ can fuse with each other to form a ring, and the ring can include a C5-C6 carbon ring or a heterocyclic ring;

each of $X_7$ to $X_{10}$ can independently represent one selected from $CR_6$ and N;

each of $R_5$ and $R_6$ can independently represent one selected from a group consisting of hydrogen, deuterium, halogen, a hydroxyl group, a cyano group, a nitro group, an amidino group, a hydrazine group, a hydrazone group, a substituted or unsubstituted C1-C20 alkyl group, a substituted or unsubstituted A cyclic C3-C20 cycloalkyl group, a substituted or unsubstituted C1-C20 heteroalkyl group, a substituted or unsubstituted C7-C20 arylalkyl group, a substituted or unsubstituted C1-C20 alkenyl group, a substituted or unsubstituted C3-C20 cycloalkenyl group, a substituted or unsubstituted C1-C20 heteroalkenyl group, an alkynyl group, a substituted or unsubstituted C6-C30 aryl group, a substituted or unsubstituted C3-C30 heteroaryl group, an alkoxy group, an amino group, a silyl group, an acyl group, a carbonyl group, a carboxylic acid group, an ester group, a nitrile group, an isonitrile group, a sulfanyl group, a sulfinyl group, a sulfonyl group and a phosphino group;

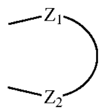

can be a bidentate ligand;

m can be an integer of 1, 2 or 3, n can be an integer of 0, 1 or 2, and m+n can be an oxidation number of the metal M.

The organometallic compound according to one implementation of the present disclosure can include a compound represented by one selected from a group consisting of following Chemical Formula II-1 and Chemical Formula II-2, based on a direction in which R (5-membered fused ring) is bonded to $X_1$ and $X_2$ in the main ligand in Chemical Formula I:

Chemical Formula II-1

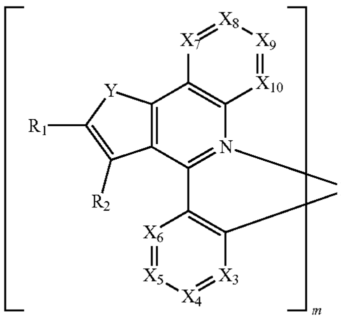

Chemical Formula II-2

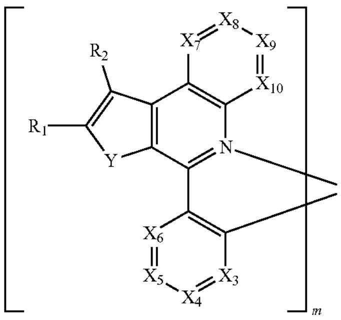

where in each of the Chemical Formula II-1 and Chemical Formula II-2, definitions of Y, $R_1$ to $R_2$, $X_3$ to $X_{10}$,

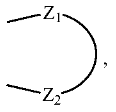

m and n are respectively the same as the definitions as described above.

In the Chemical Formula I representing the organometallic compound according to one implementation of the present disclosure, it is more preferable that the additional fused ring is introduced to a phenyl group in the 2-phenylquinoline of the Chemical Formula I. Due to the introduction of the additional fused ring, rigidity can be imparted to the organometallic compound molecule such that the full width at half maximum (FWHM) is narrow and thus color purity is improved. Specifically, the compound represented by the Chemical Formula I can include a compound represented by one selected from a group consisting of following Chemical Formula III-1 and Chemical Formula III-2:

Chemical Formula III-1

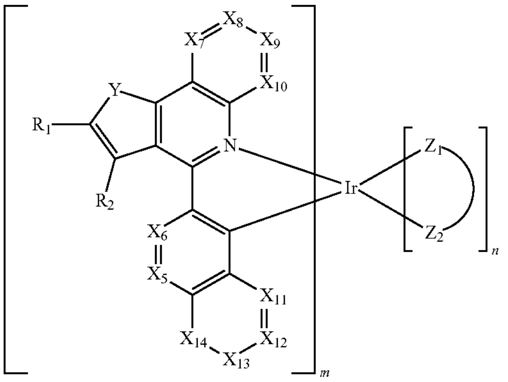

Chemical Formula III-2

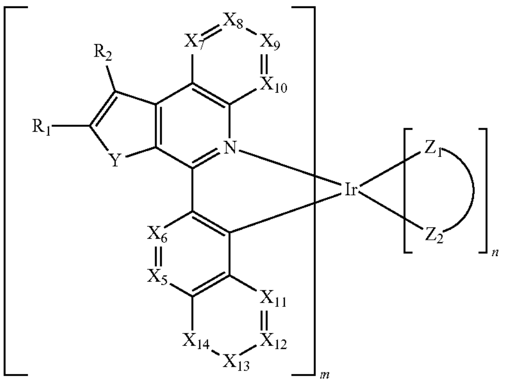

where in each of the Chemical Formula III-1 and Chemical Formula III-2, each of $X_{11}$ to $X_{14}$ can independently represent one selected from $CR_7$ and N;

$R_7$ can represent one selected from a group consisting of hydrogen, deuterium, halogen, a hydroxyl group, a cyano group, a nitro group, an amidino group, a hydrazine group, a hydrazone group, a substituted or unsubstituted C1-C20 alkyl group, a substituted or unsubstituted A cyclic C3-C20 cycloalkyl group, a substituted or unsubstituted C1-C20 heteroalkyl group, a substituted or unsubstituted C7-C20 arylalkyl group, a substituted or unsubstituted C1-C20 alkenyl group, a substituted or unsubstituted C3-C20 cycloalkenyl group, a substituted or unsubstituted C1-C20 heteroalkenyl group, an alkynyl group, a substituted or unsubstituted C6-C30 aryl group, a substituted or unsubstituted C3-C30 heteroaryl group, an alkoxy group an amino group, a silyl group, an acyl group, a carbonyl group, a carboxylic acid group, an ester group, a nitrile group, an isonitrile group, a sulfanyl group, a sulfinyl group, a sulfonyl group and a phosphino group; definitions of Y, $R_1$ to $R_2$, $X_5$ to $X_{10}$,

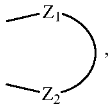, m and n are respectively the same as the definitions as described above.

In the organometallic compound according to one implementation of the present disclosure, a bidentate ligand as an auxiliary ligand can bind to the central coordination metal. The bidentate ligand according to the present disclosure include an electron donor, which increases the electron density of the central coordination metal, thereby reducing energy of metal to ligand charge transfer (MLCT) and increasing contribution of $^3$MLCT to a $T_1$ state. As a result, an organic electroluminescent device including the organometallic compound according to one implementation of the present disclosure can implement improved luminescent properties such as high luminous efficiency and high external quantum efficiency.

Phosphorescence can be efficiently obtained at room temperature using an iridium (Ir) or platinum (Pt) metal complex with a large atomic number. Thus, in the organometallic compound according to one implementation of the present disclosure, the central coordination metal (M) can be preferably iridium (Ir) or platinum (Pt), more preferably, iridium (Ir). However, the disclosure is not limited thereto.

A specific example of the compound represented by the Chemical Formula I of the present disclosure can include one selected from a group consisting of following compounds 1 to 291. However, the disclosure is not limited thereto as long as the compound falls within the definition of the Chemical Formula I.

1

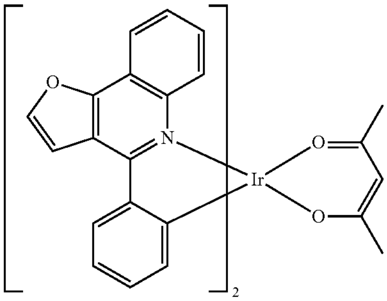

2

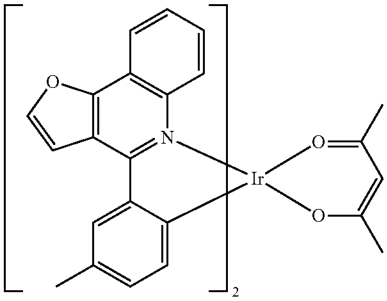

-continued

3

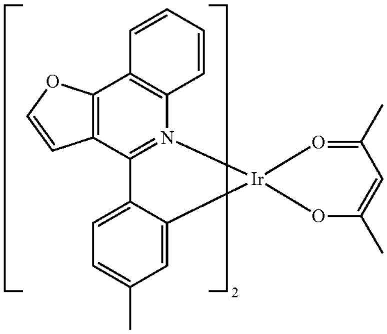

4

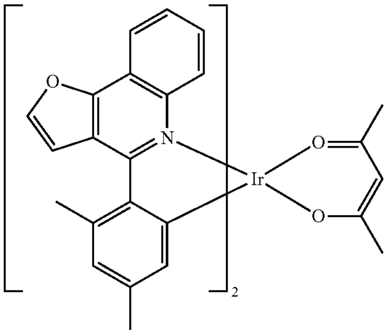

5

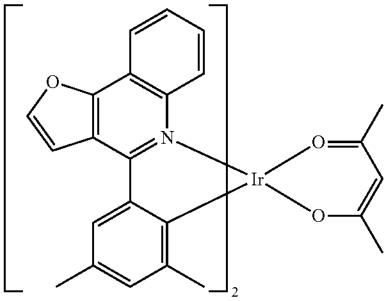

6

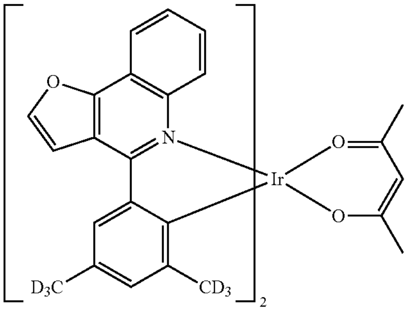

7

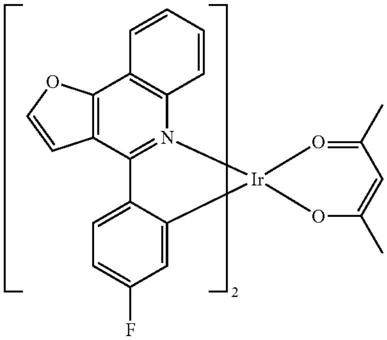

-continued
8
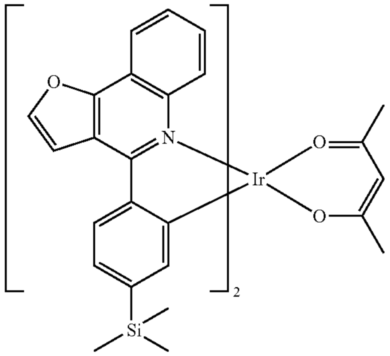
9
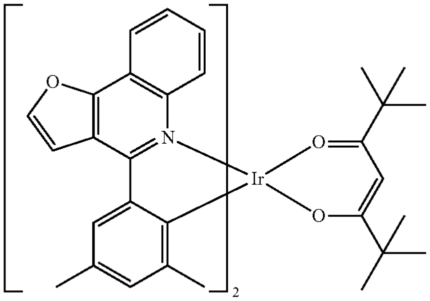
10
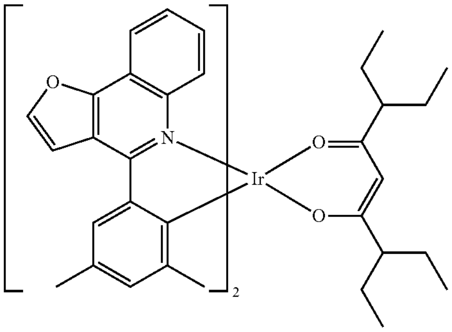
11
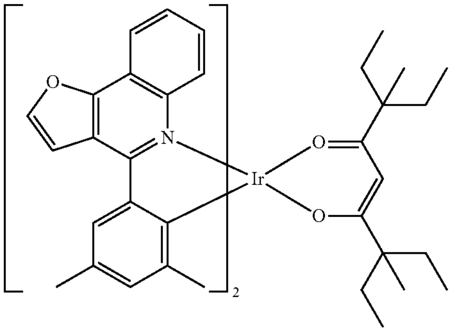
-continued
12
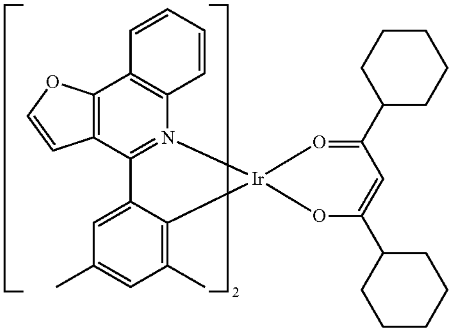
13
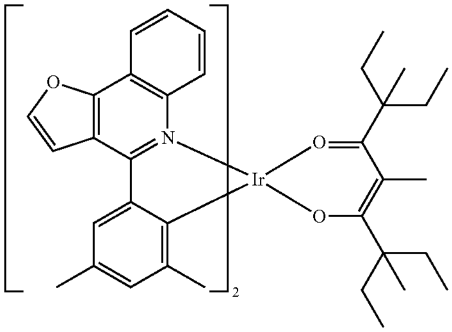
14
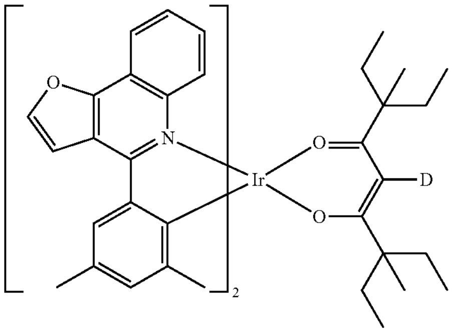
15
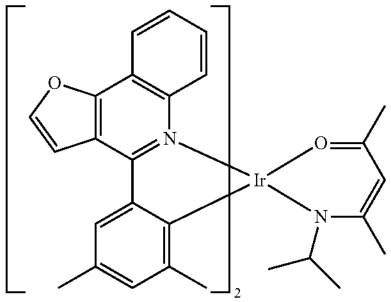
16
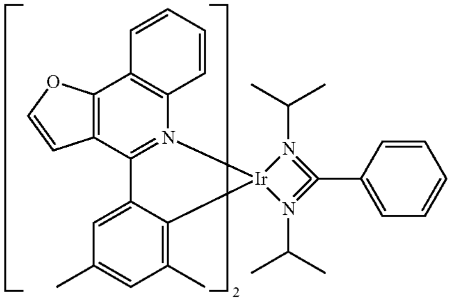

-continued
17
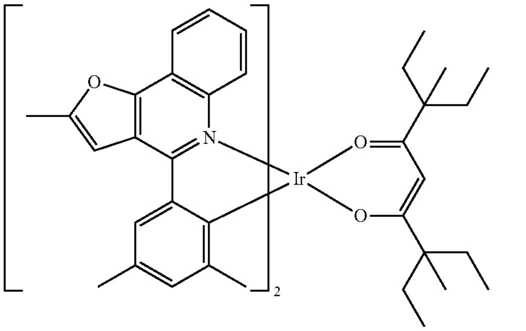
18
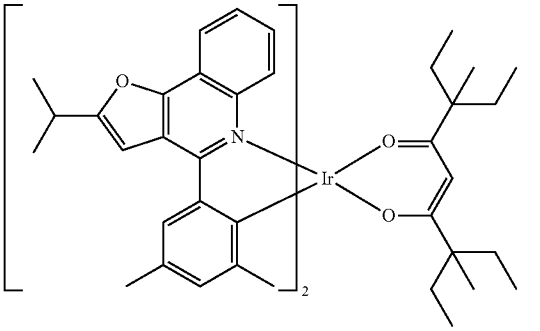
19
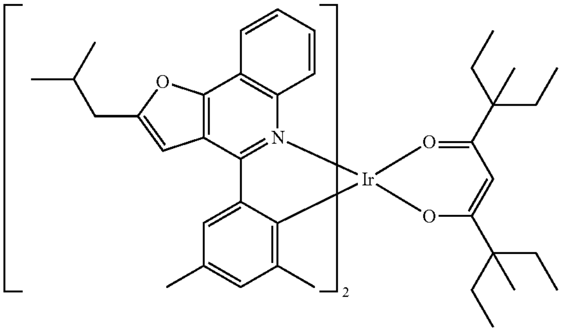
20
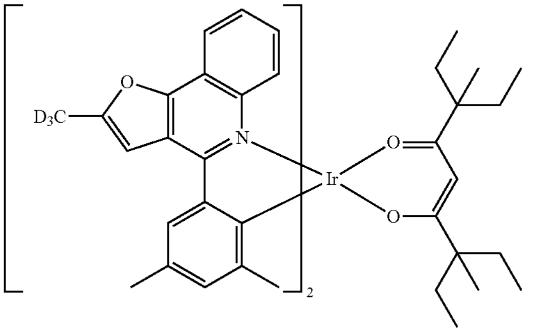
-continued
21
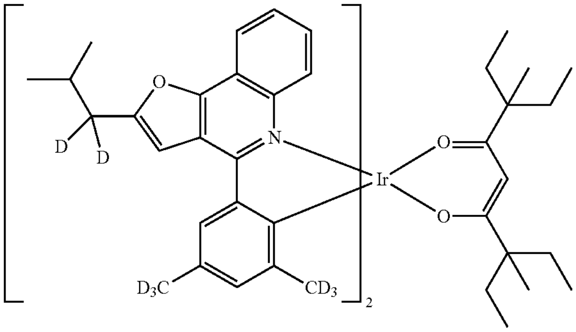
22
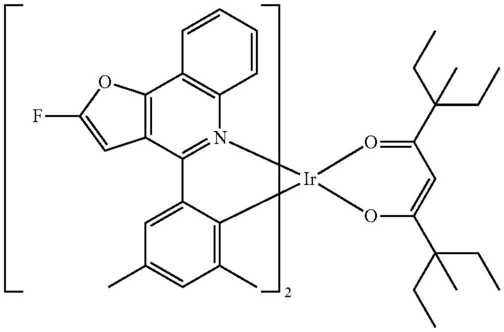
23
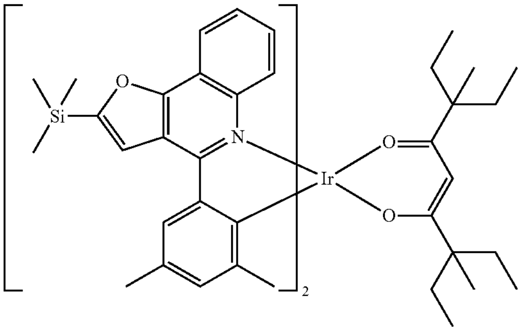
24
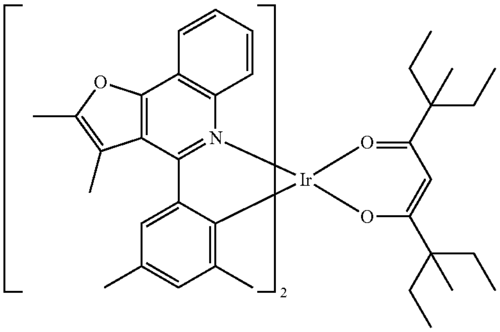

-continued
25
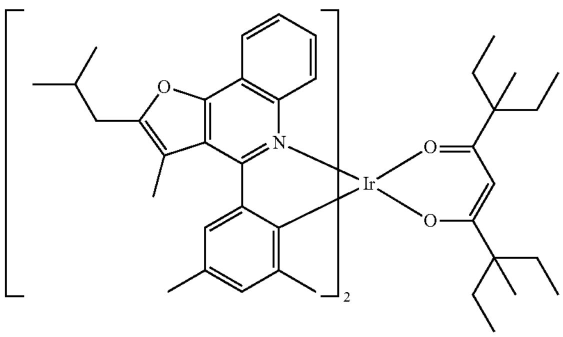
26
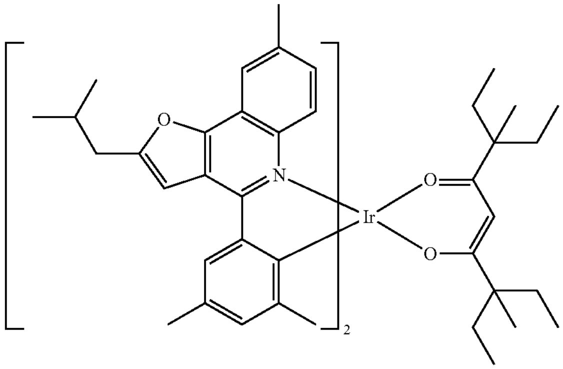
27
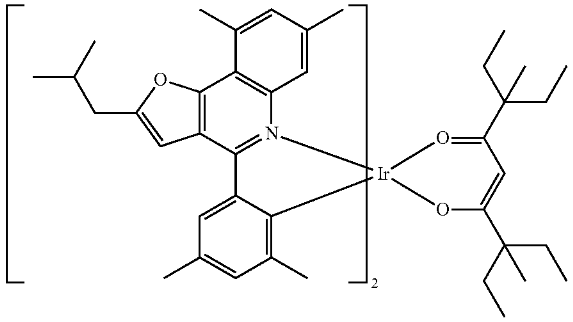
28
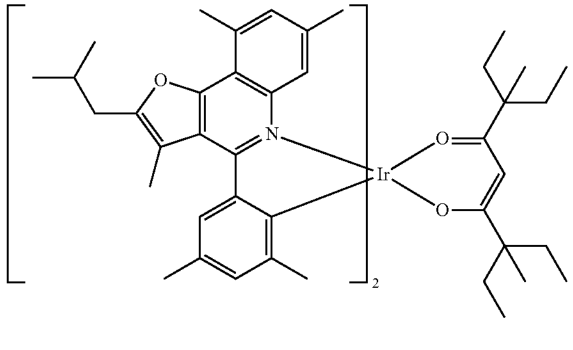
-continued
29
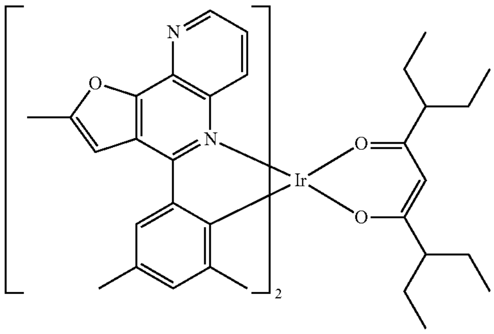
30
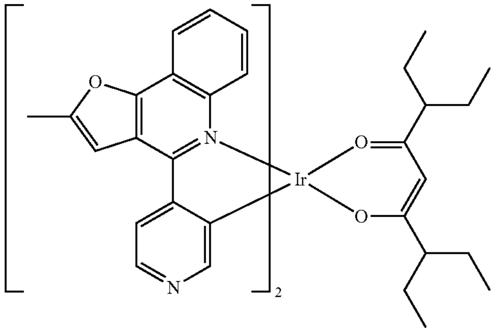
31
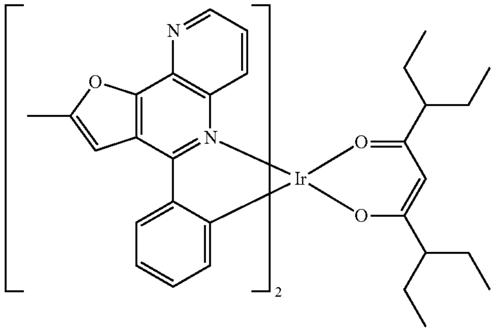
32
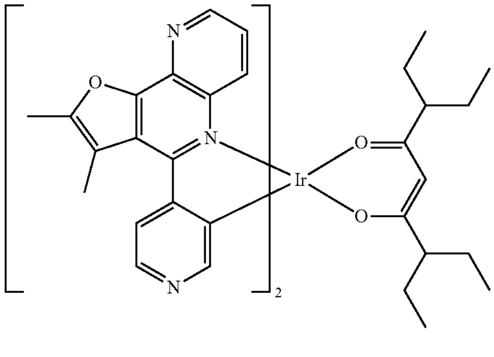

-continued
33
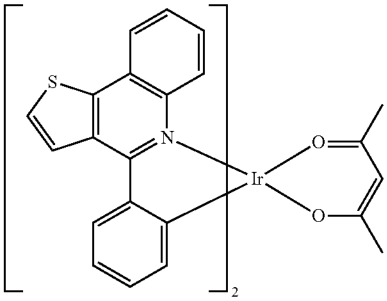
34
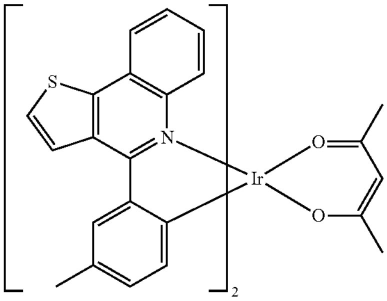
35
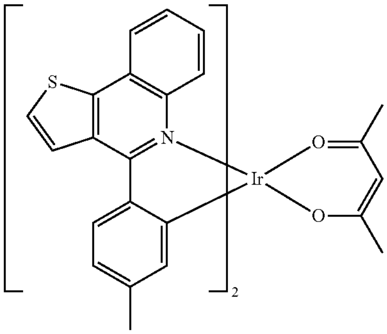
36
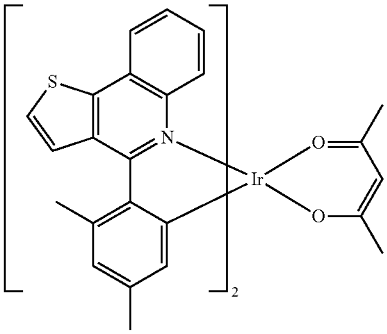
37
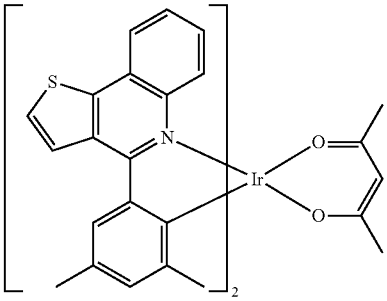
-continued
38
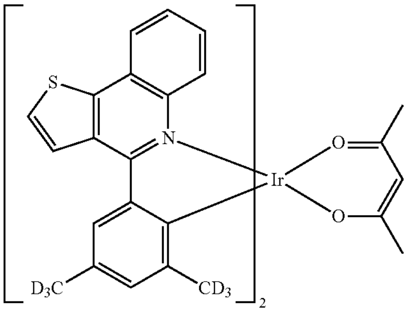
39
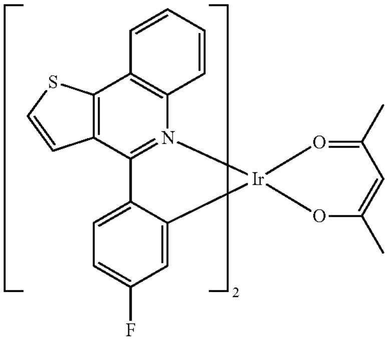
40
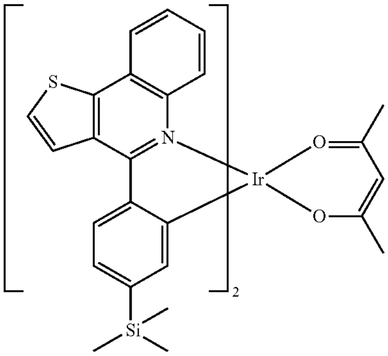
41
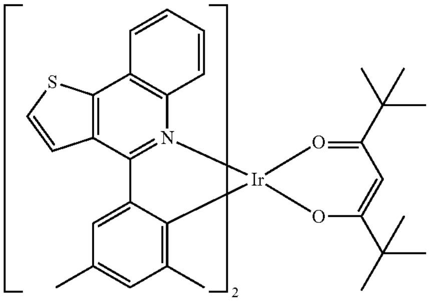

-continued
42
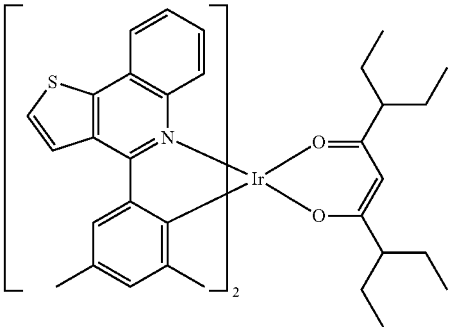
43
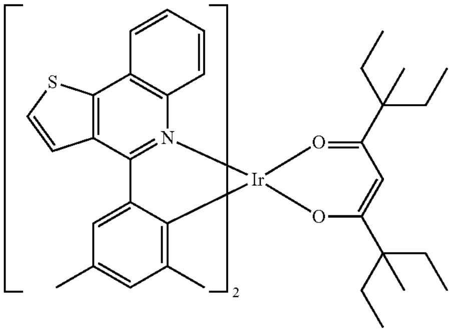
44
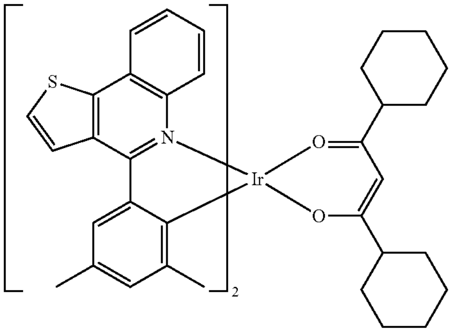
45
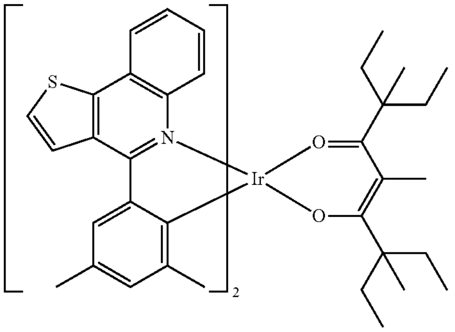
-continued
46
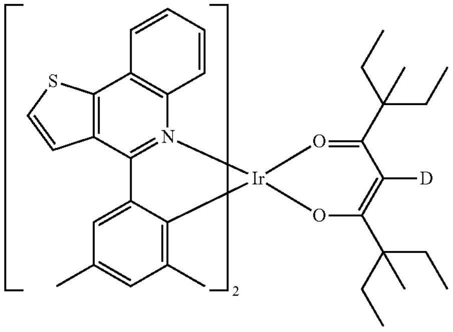
47
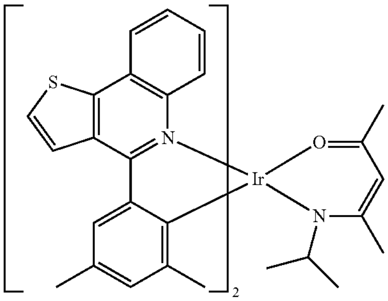
48
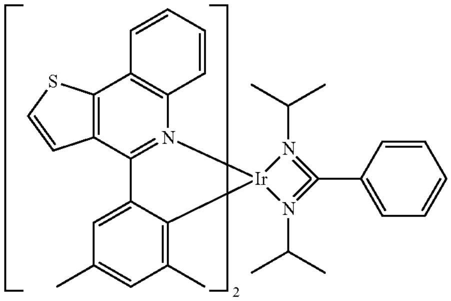
49
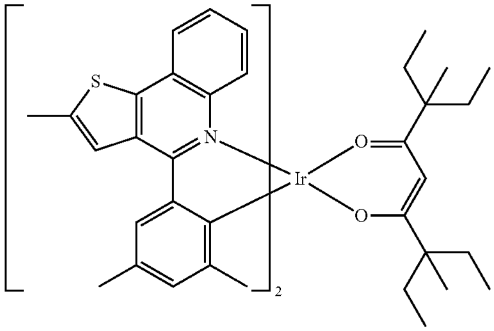
50
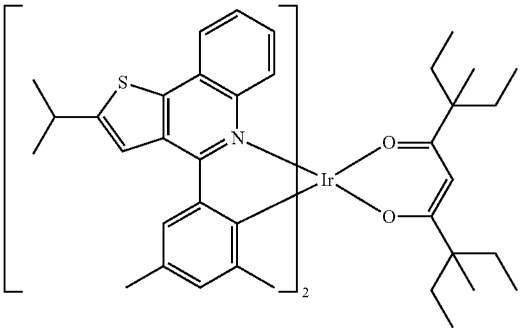

-continued
51
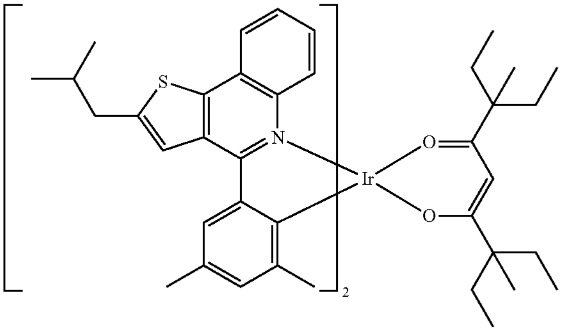
52
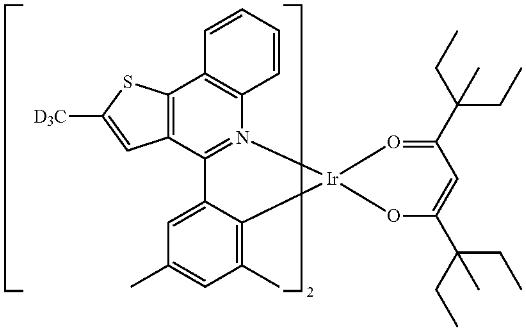
53
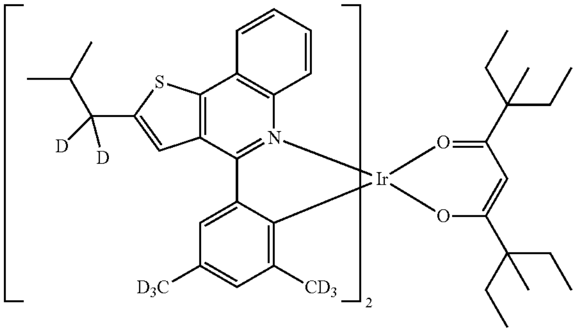
54
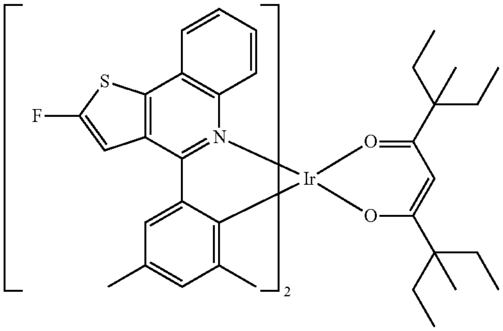
-continued
55
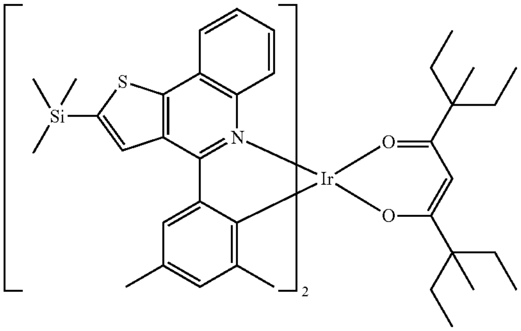
56
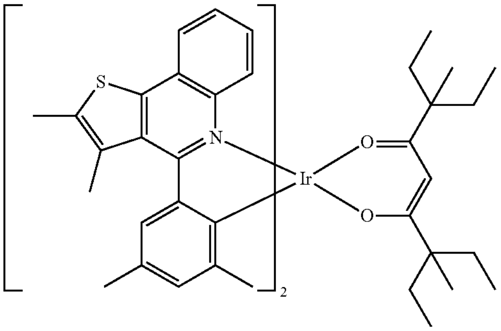
57
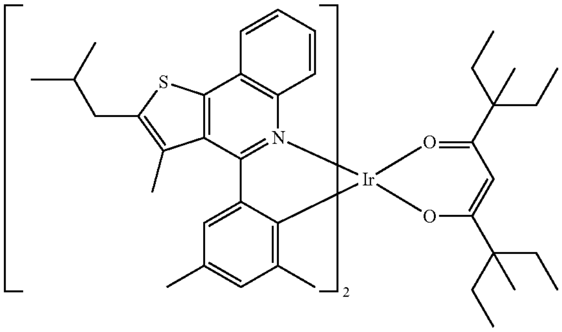
58
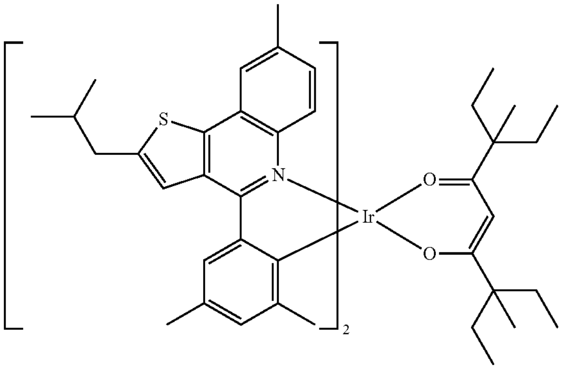

-continued
59
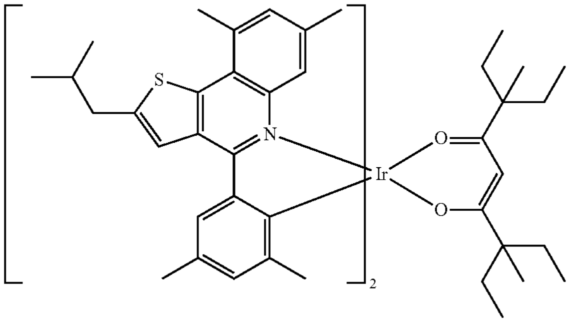
60
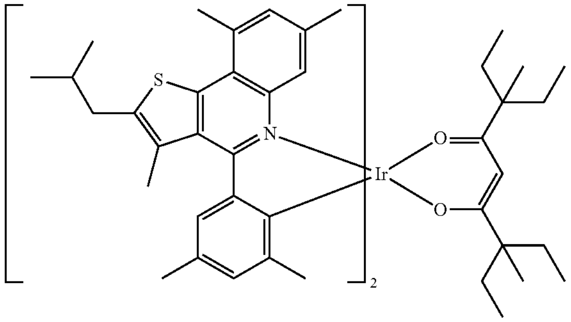
61
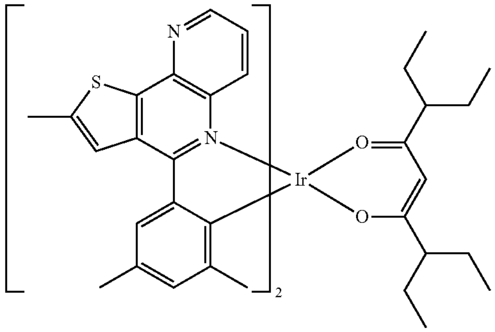
62
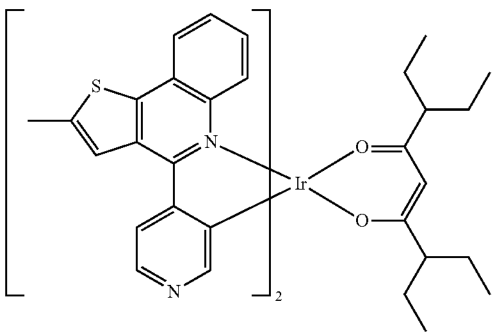
-continued
63
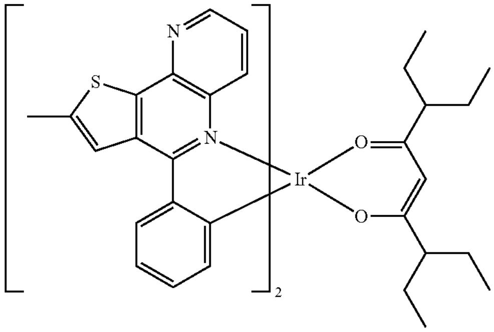
64
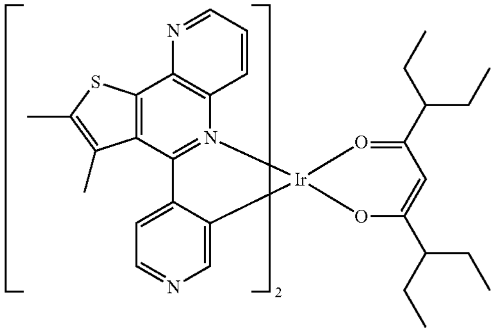
65
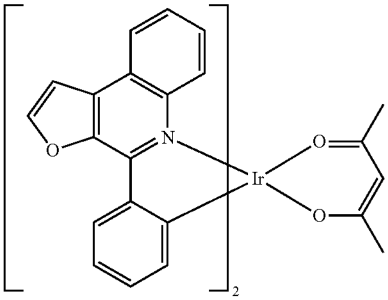
66
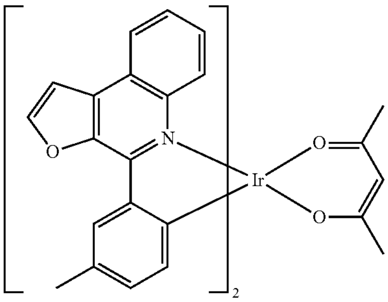
67
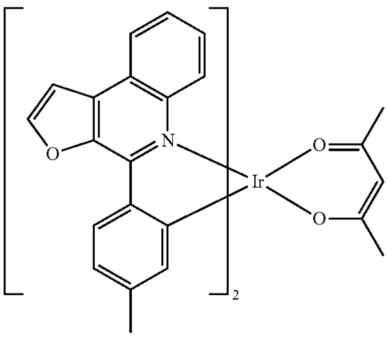

-continued
68
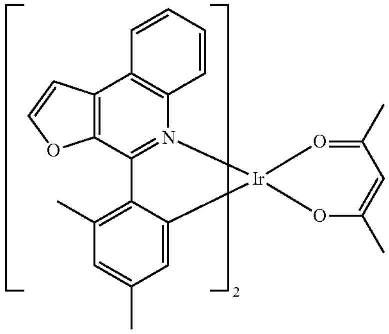
69
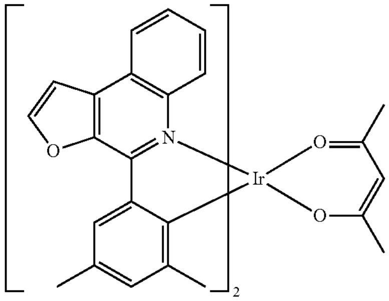
70
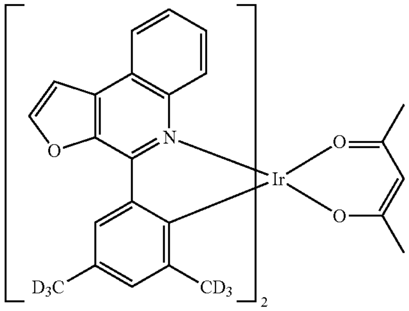
71
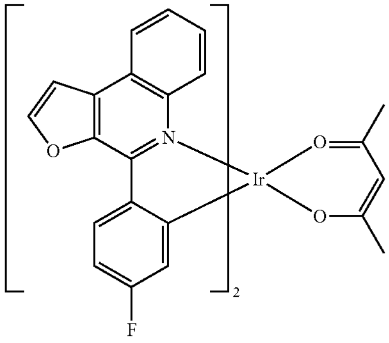
-continued
72
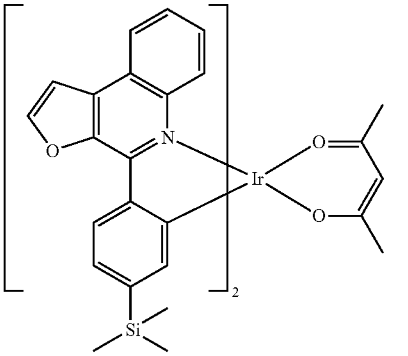
73
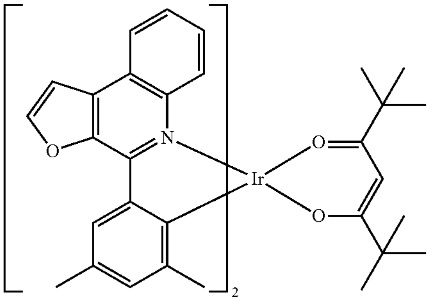
74
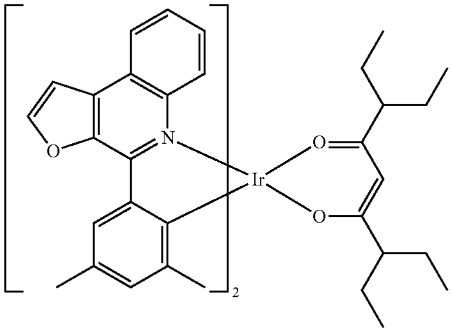
75
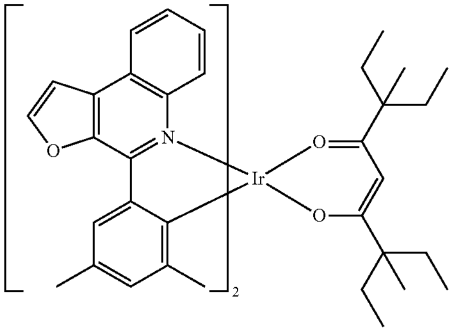

-continued
76
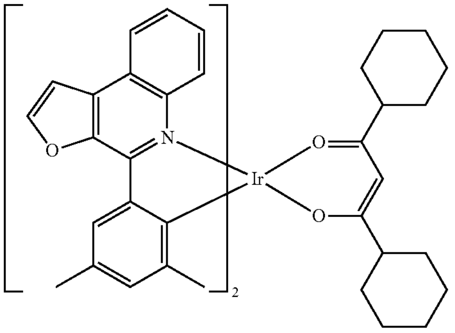
77
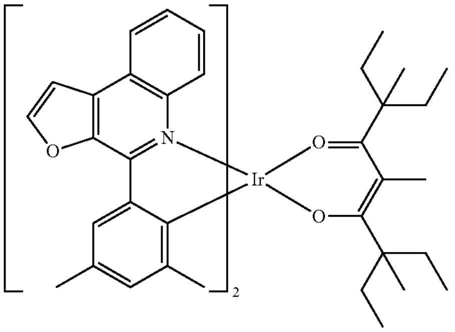
78
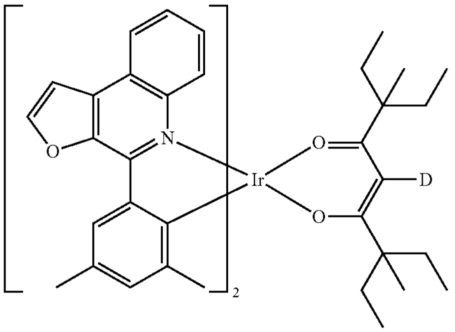
79
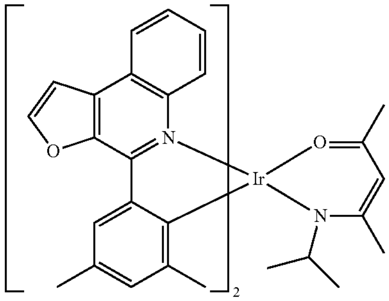
80
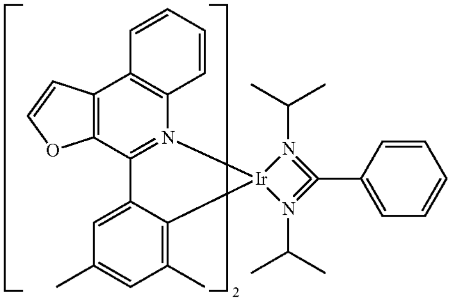
-continued
81
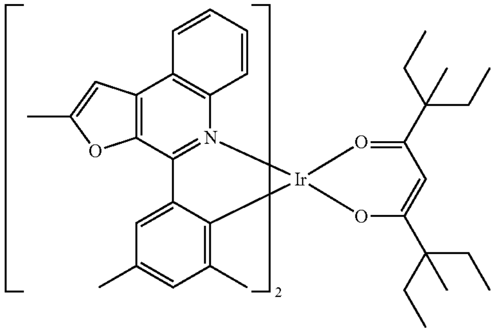
82
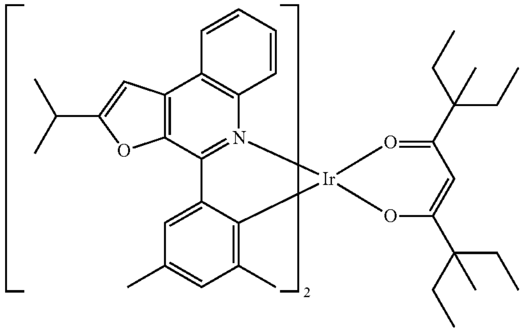
83
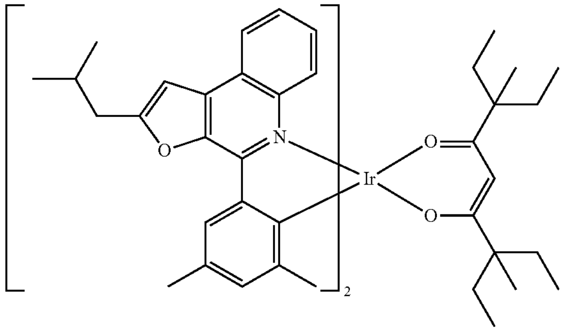
84
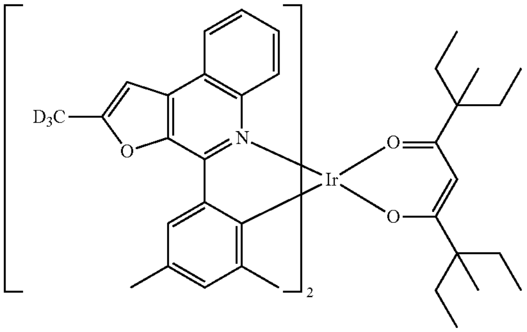

85
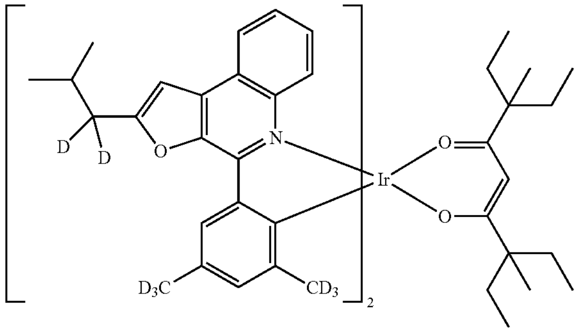
86
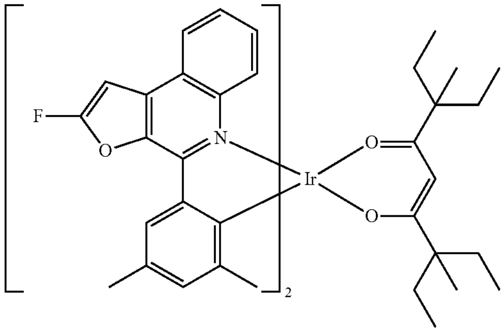
87
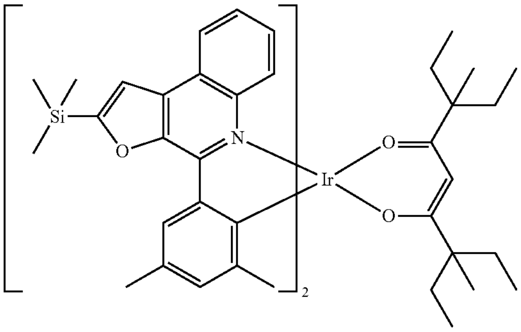
88
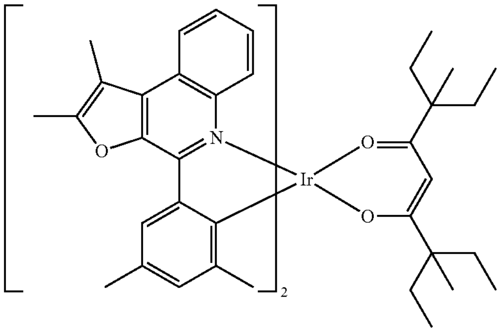
89
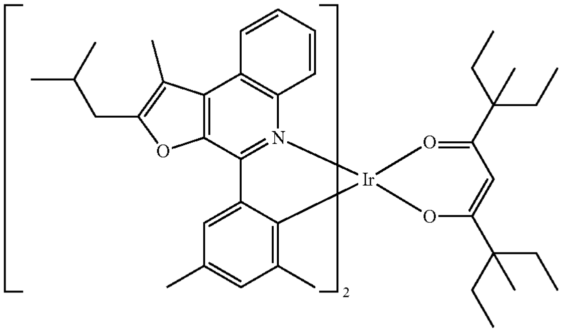
90
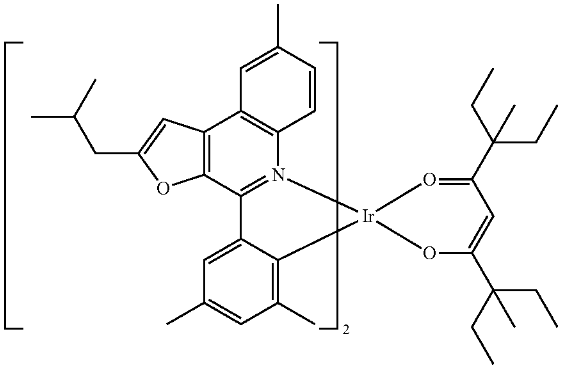
91
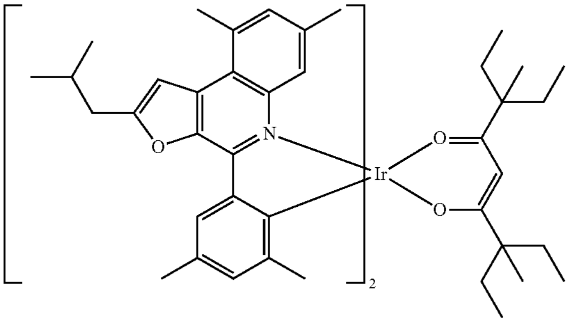
92
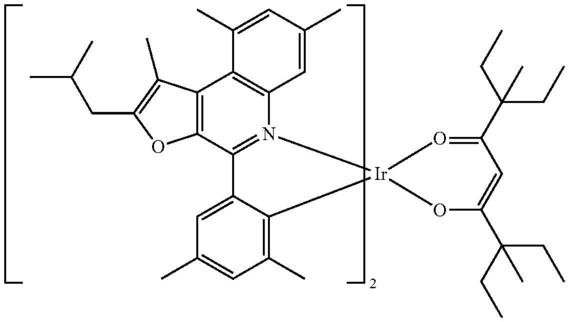

-continued
93
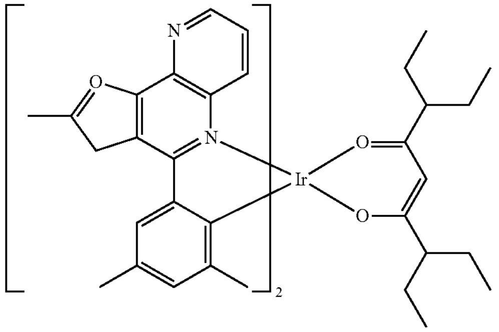
94
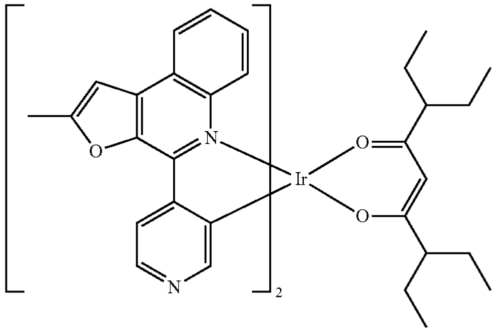
95
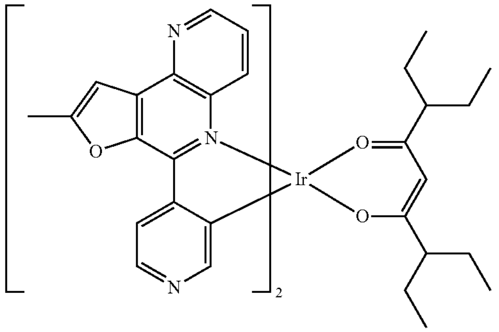
96
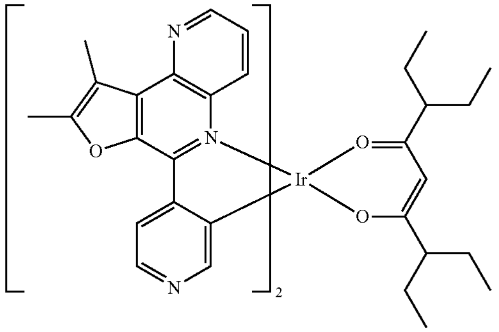
97
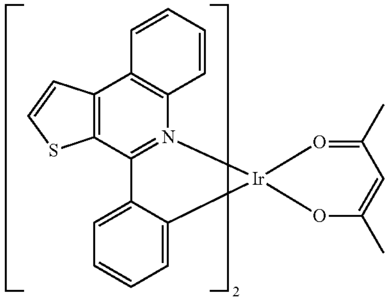
-continued
98
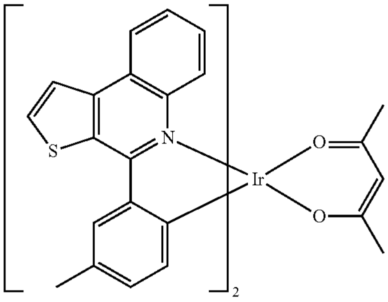
99
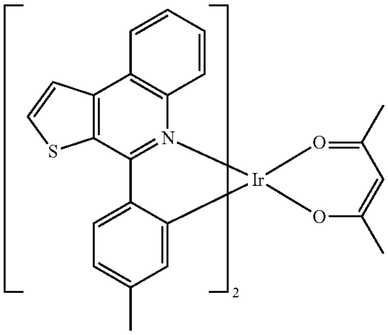
100
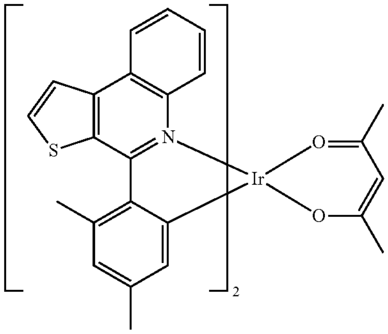
101
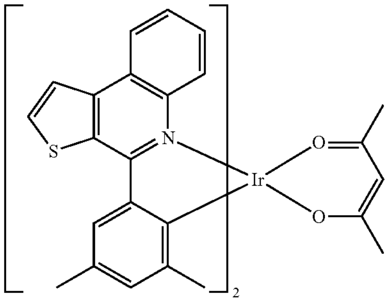
102
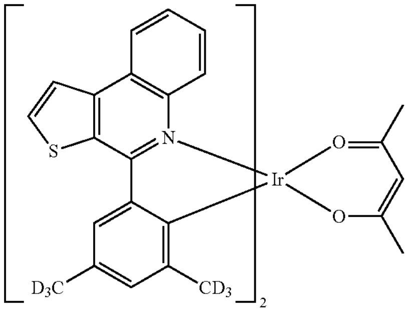

-continued
103
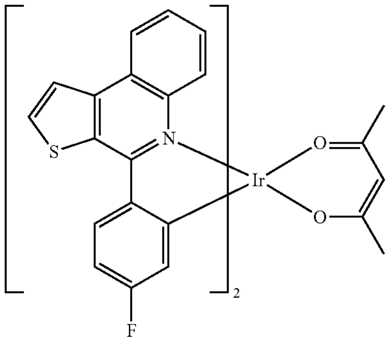
104
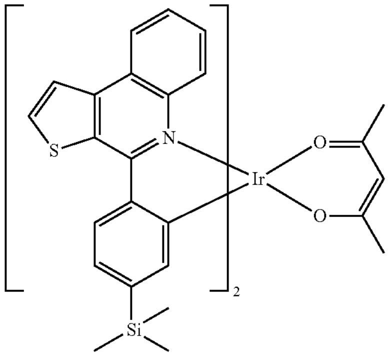
105
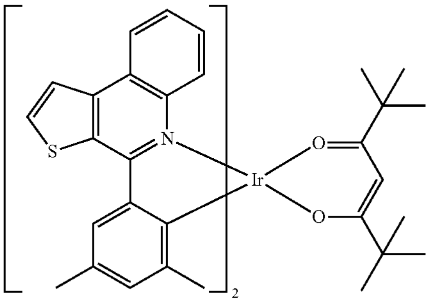
106
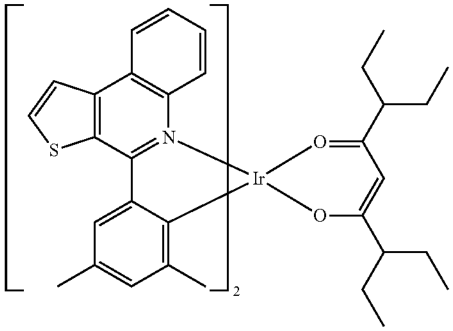
-continued
107
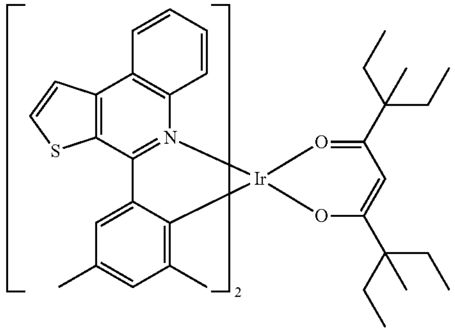
108
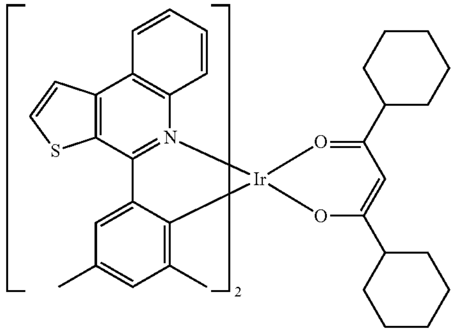
109
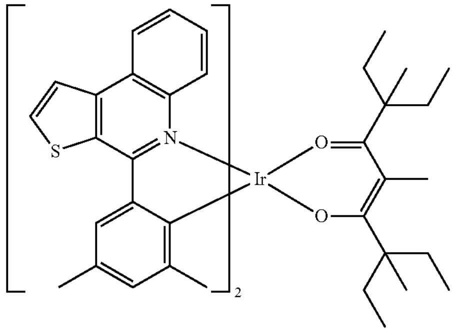
110
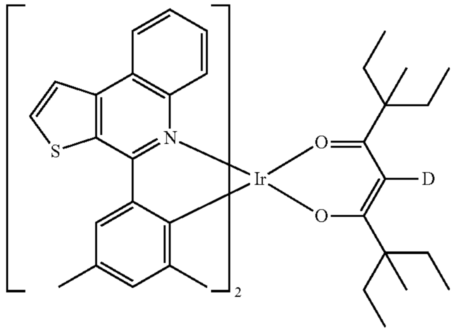

-continued
111
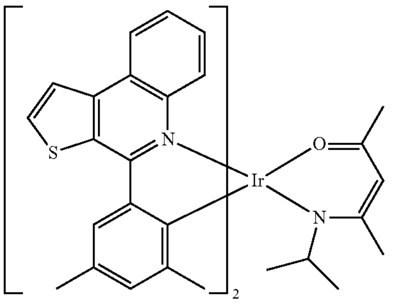
112
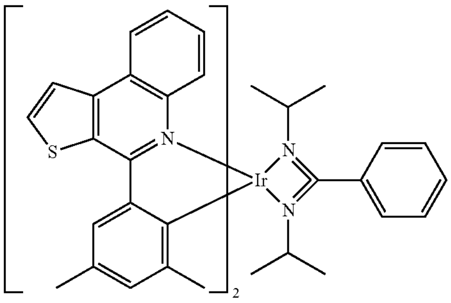
113
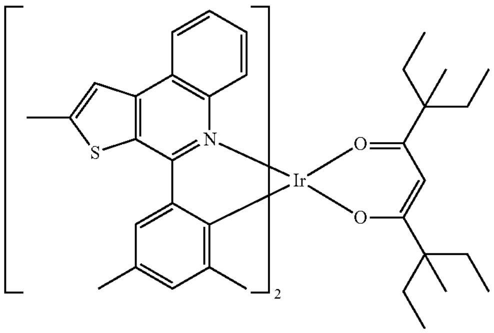
114
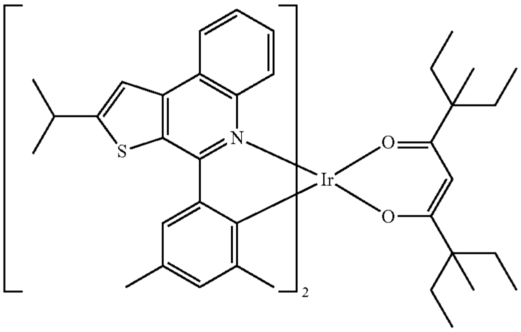
-continued
115
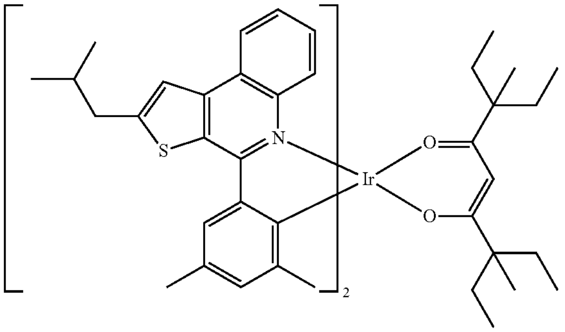
116
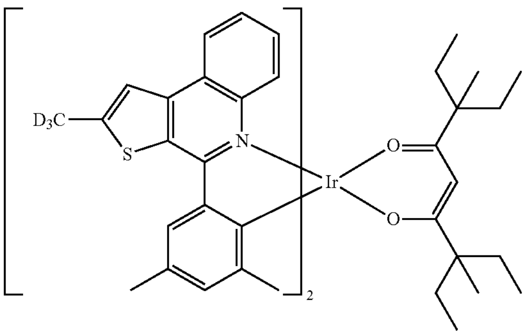
117
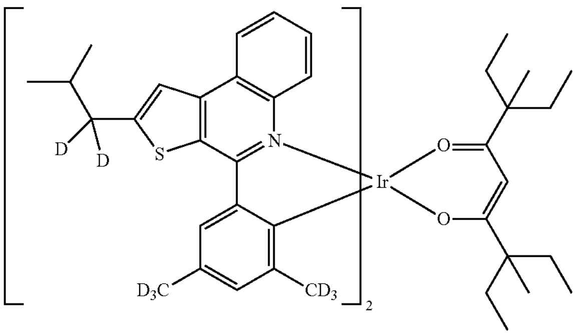
118
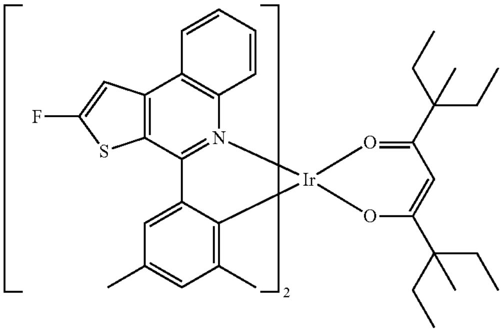

-continued
119
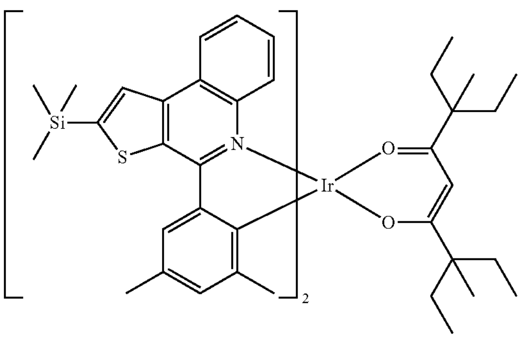
120
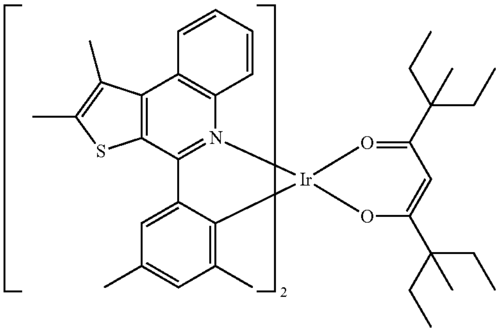
121
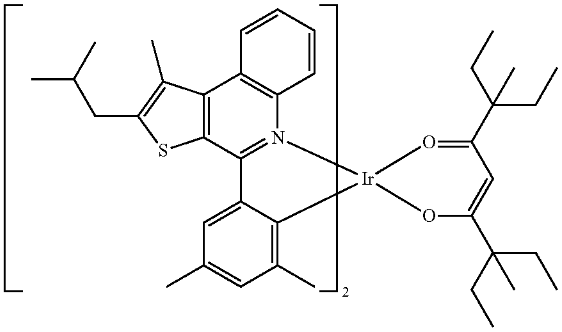
122
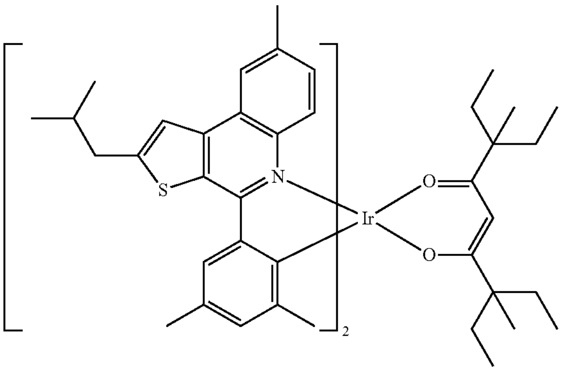
-continued
123
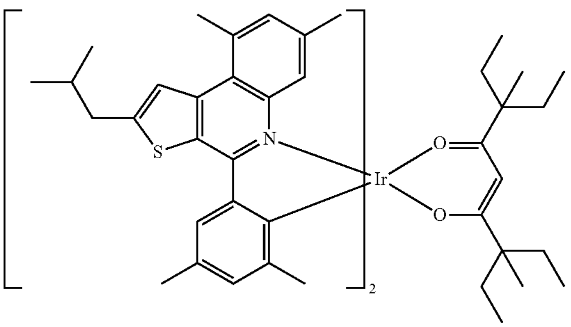
124
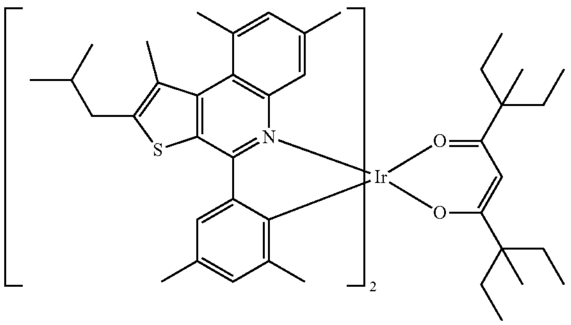
125
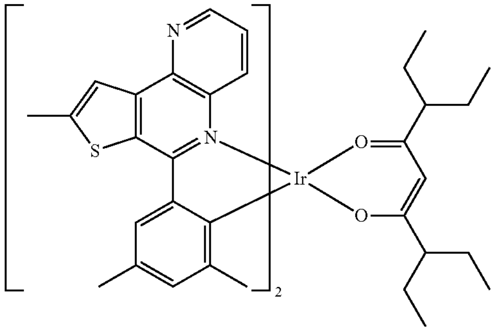
126
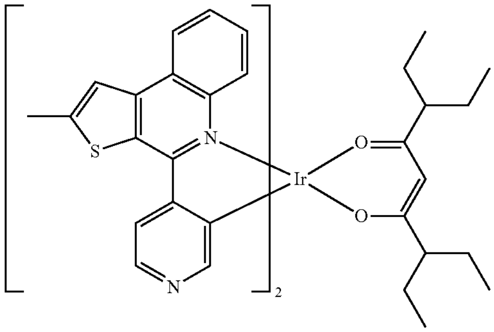

-continued
127
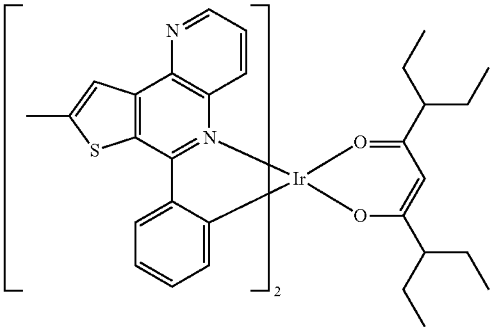
128
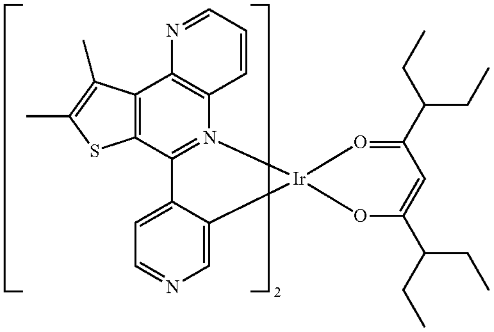
129
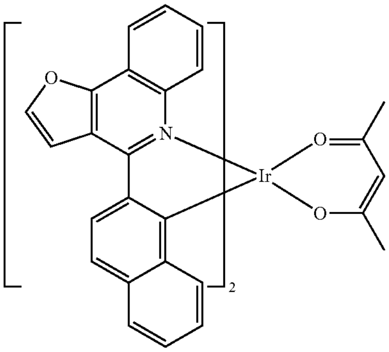
130
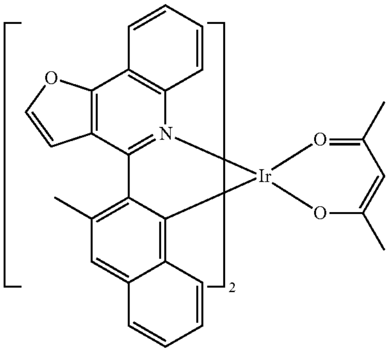
-continued
131
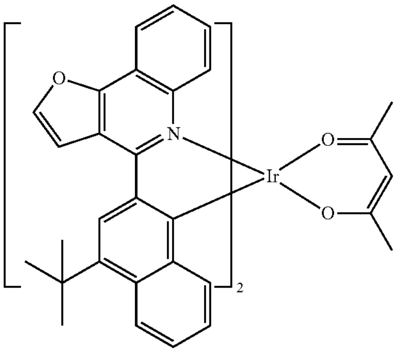
132
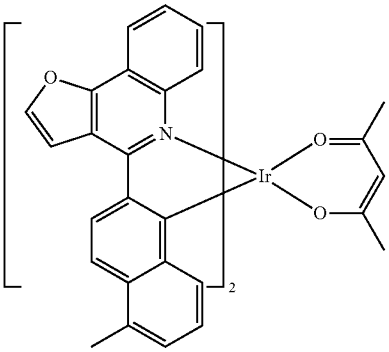
133
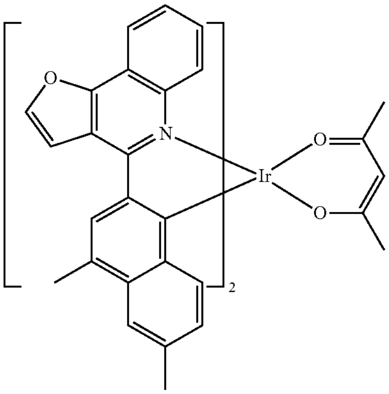
134
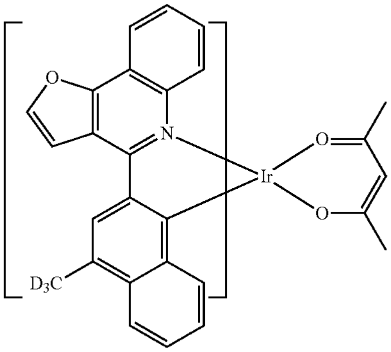

-continued
135
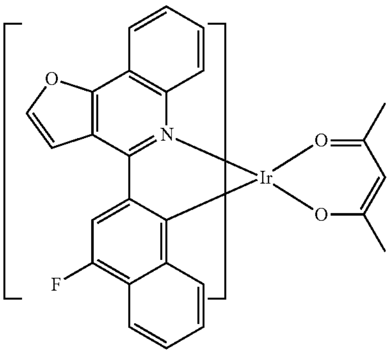
136
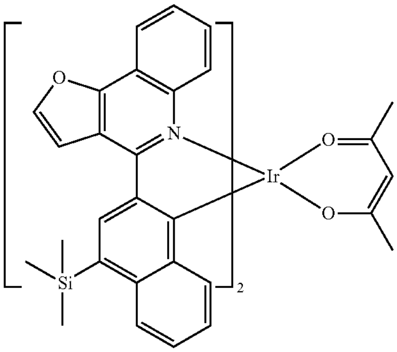
137
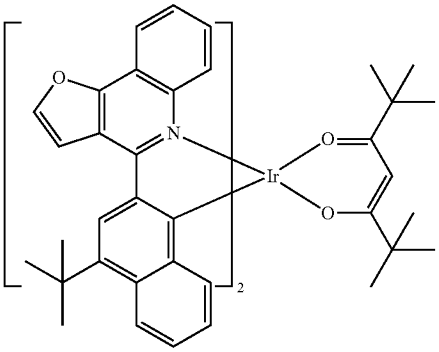
138
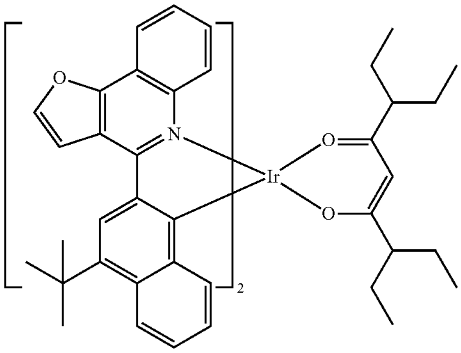
-continued
139
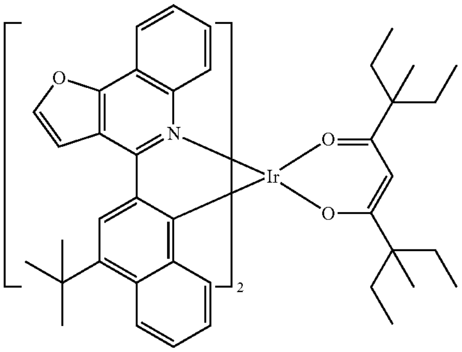
140
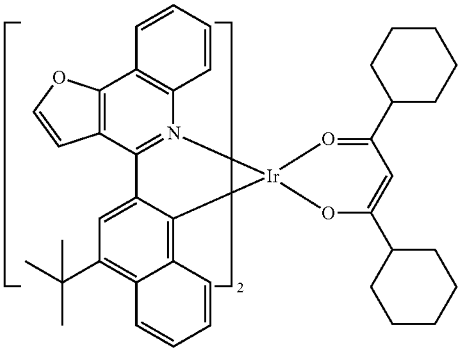
141
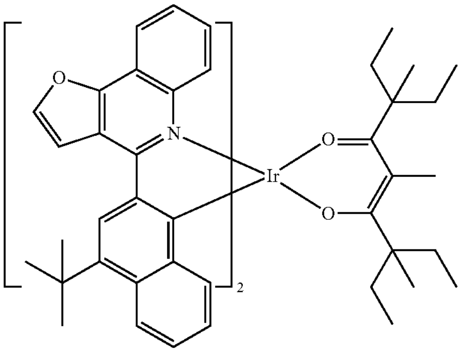
142
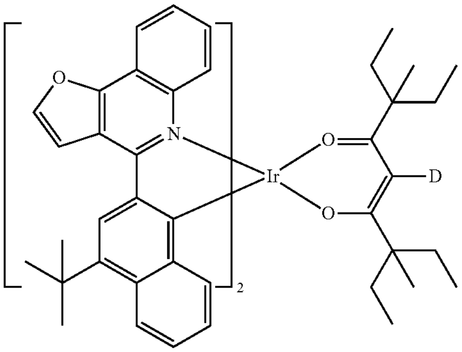

-continued
143
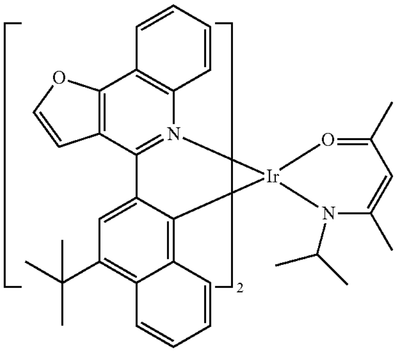
144
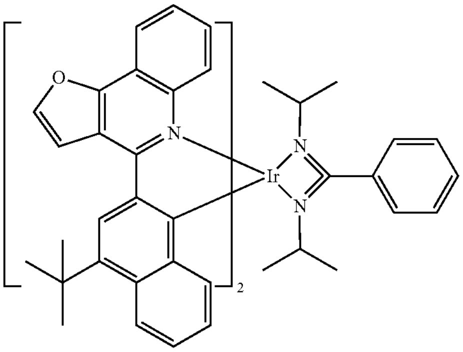
145
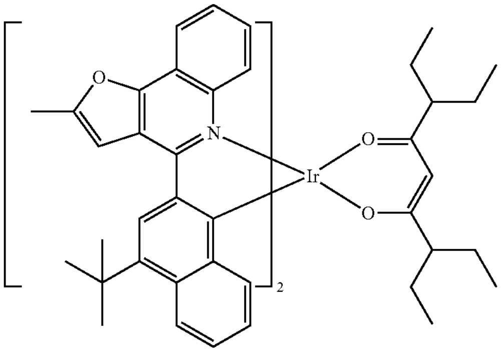
146
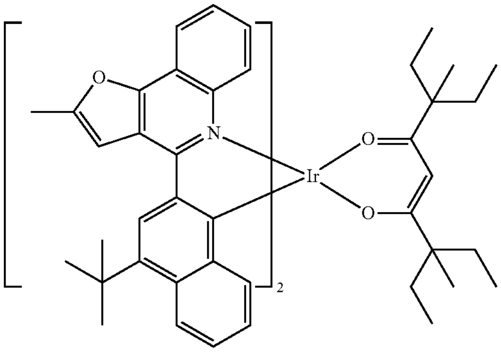
-continued
147
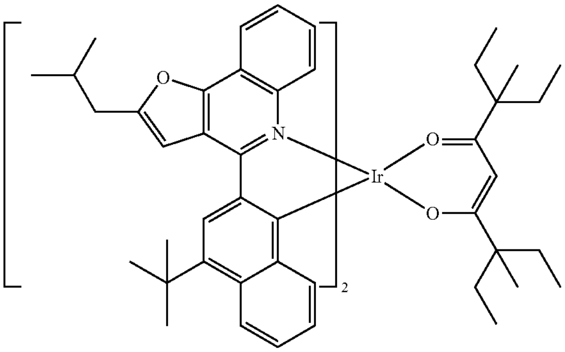
148
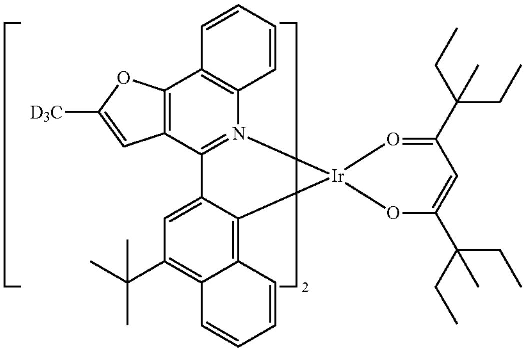
149
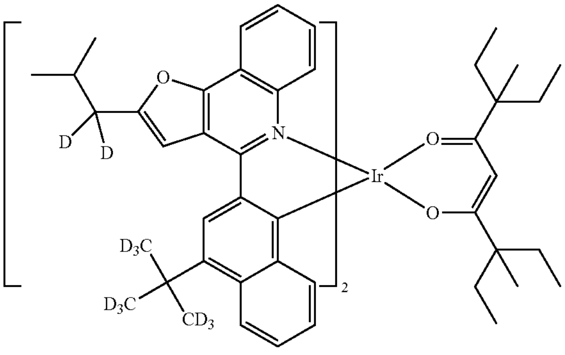
150
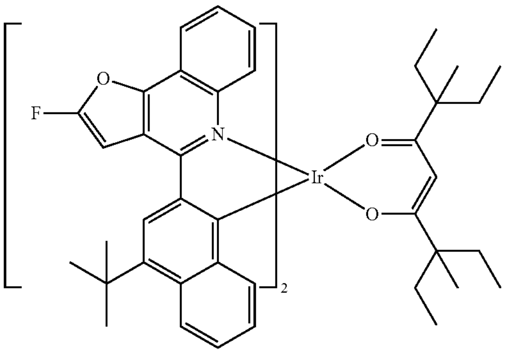

-continued
151
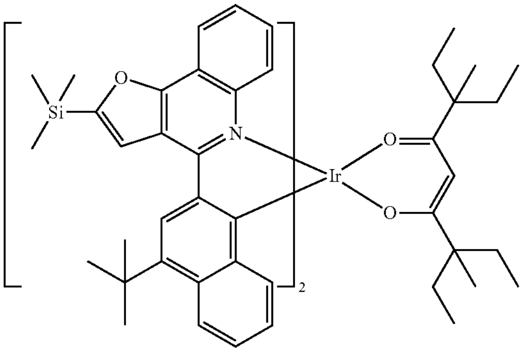
152
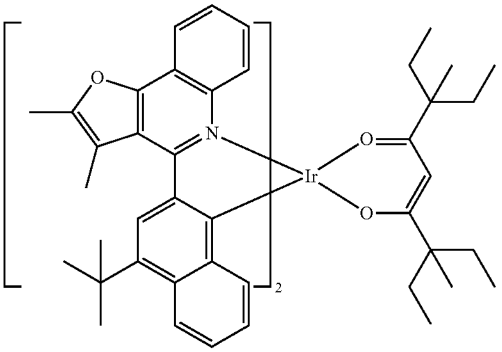
153
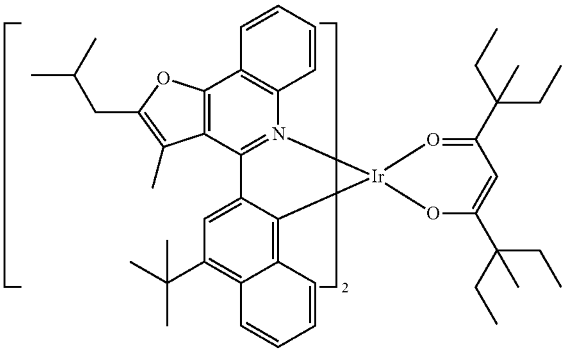
154
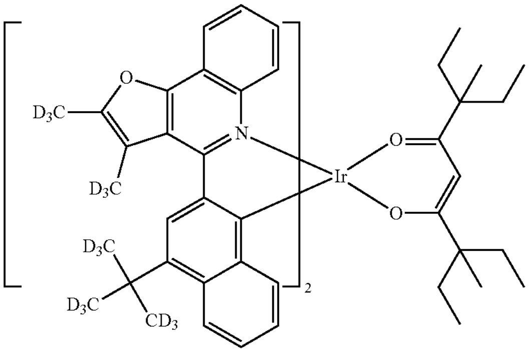
-continued
155
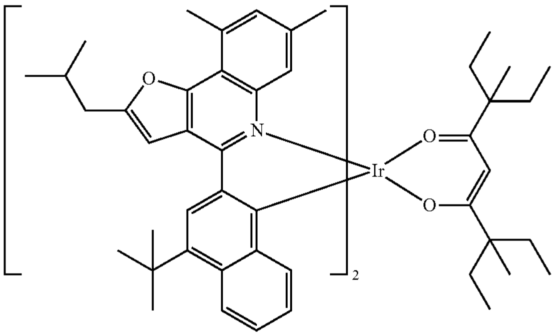
156
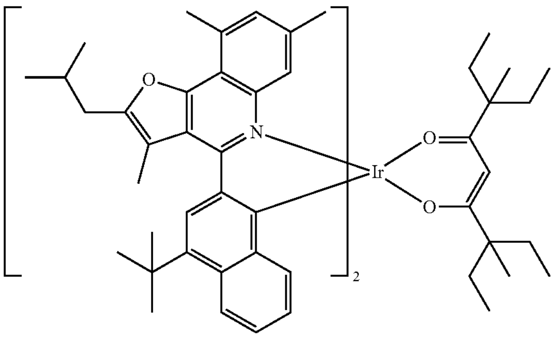
157
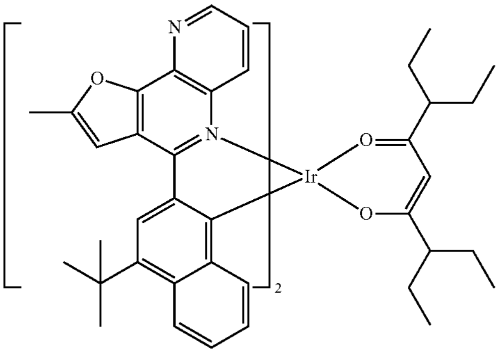
158
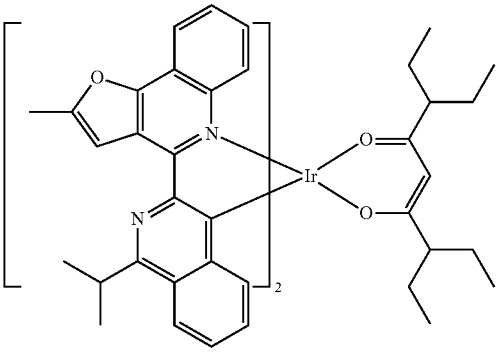

-continued
159
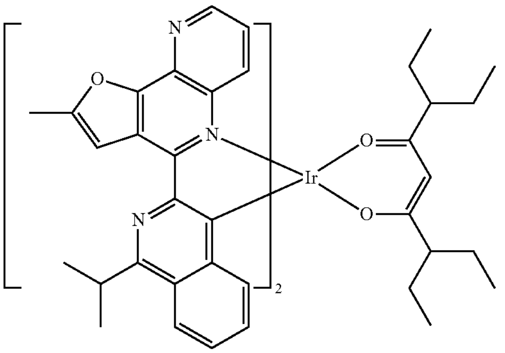
160
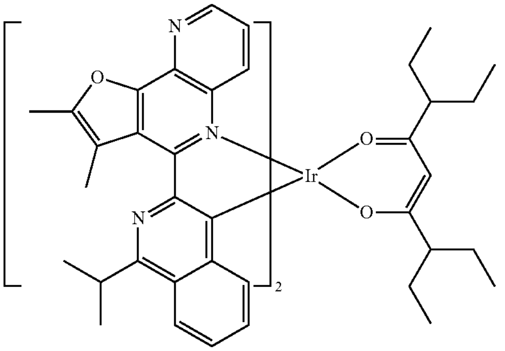
161
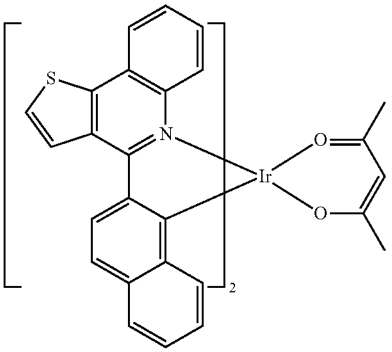
162
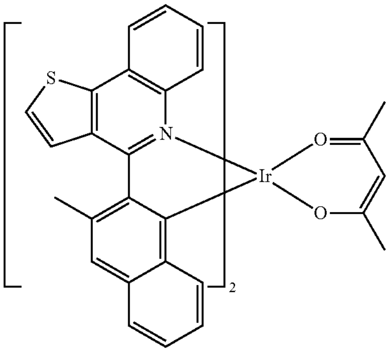
-continued
163
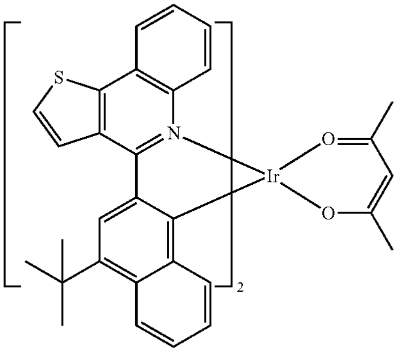
164
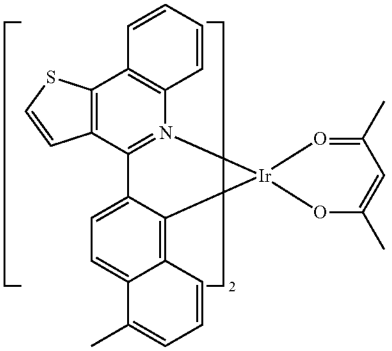
165
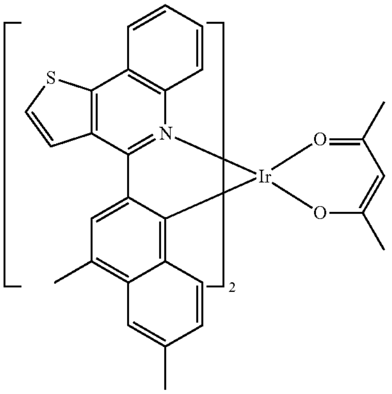
166
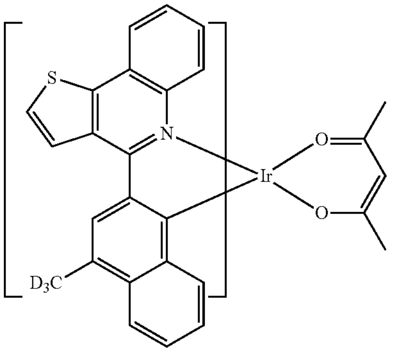

-continued
167
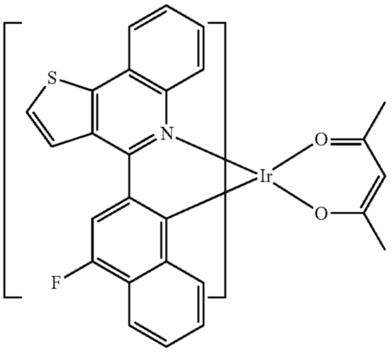
168
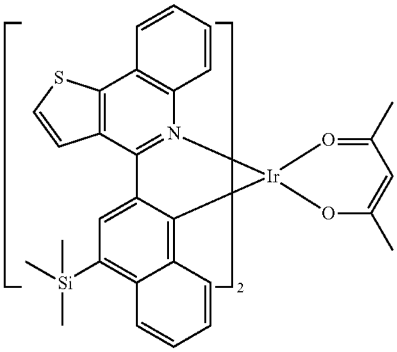
169
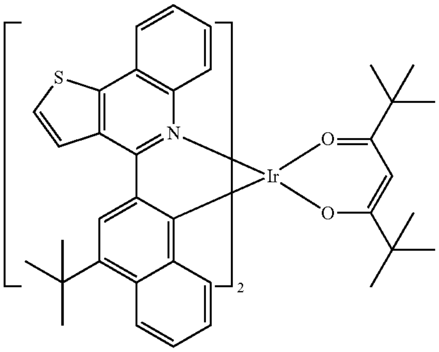
170
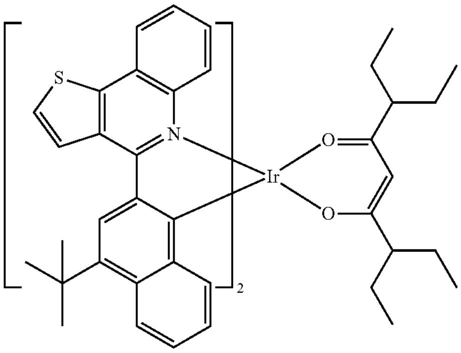
-continued
171
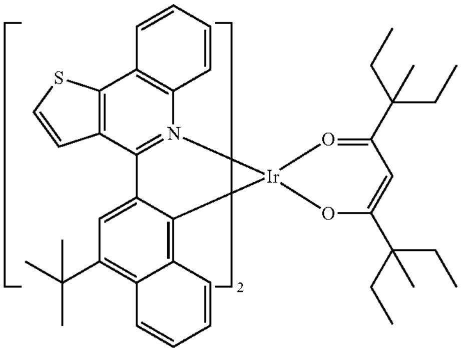
172
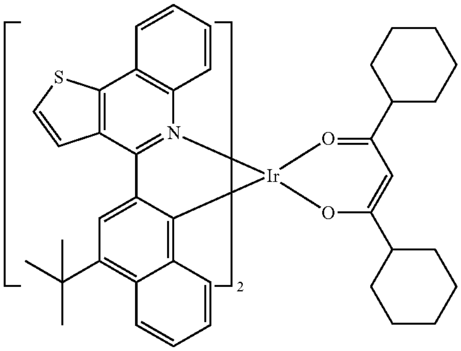
173
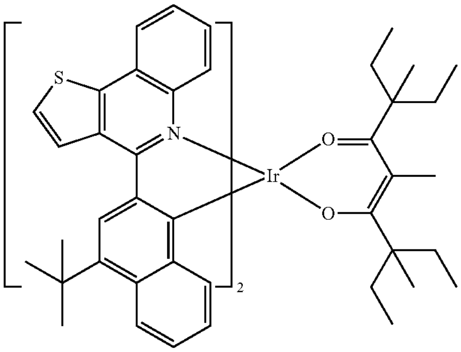
174
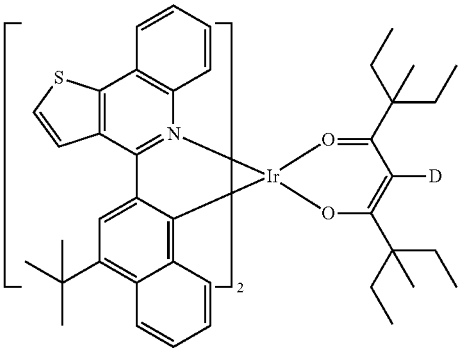

-continued
175
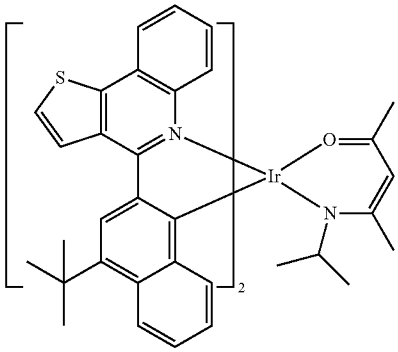
176
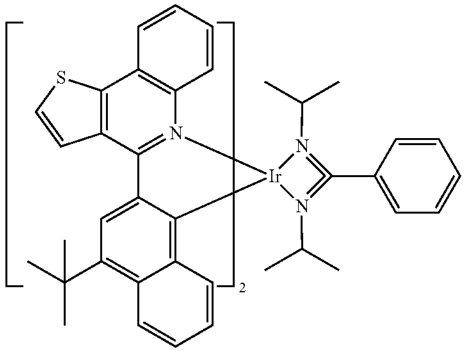
177
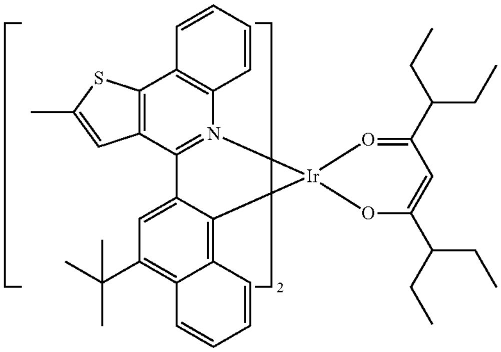
178
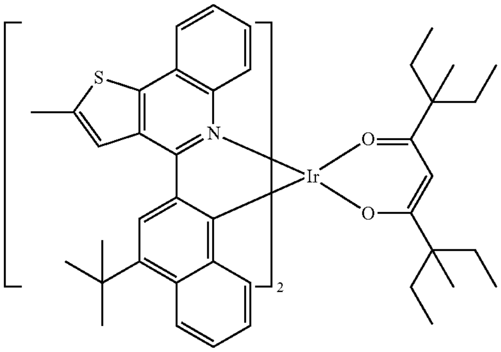
-continued
179
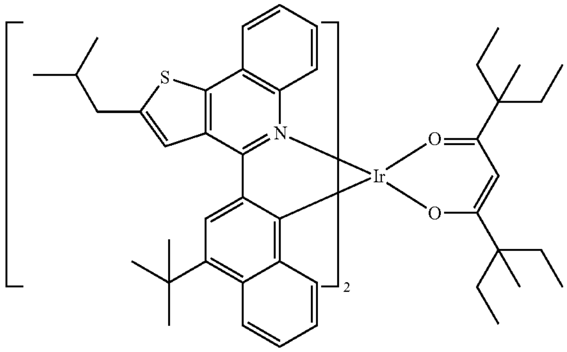
180
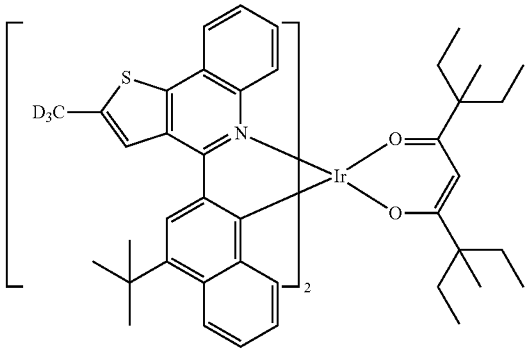
181
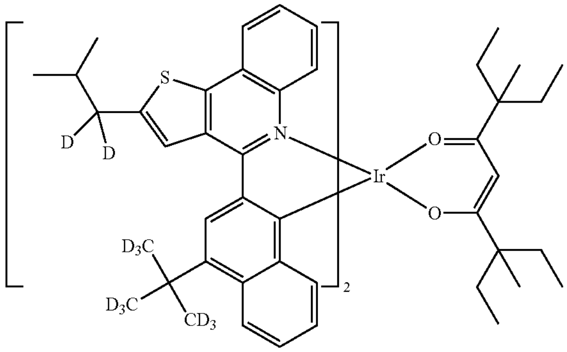
182
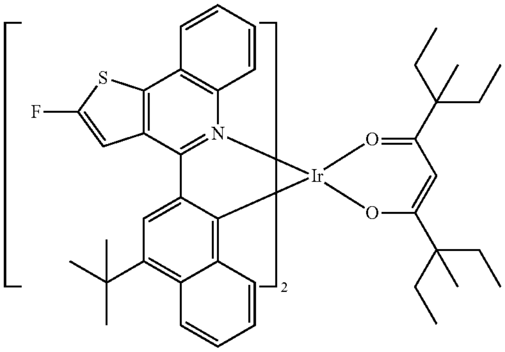

-continued
183
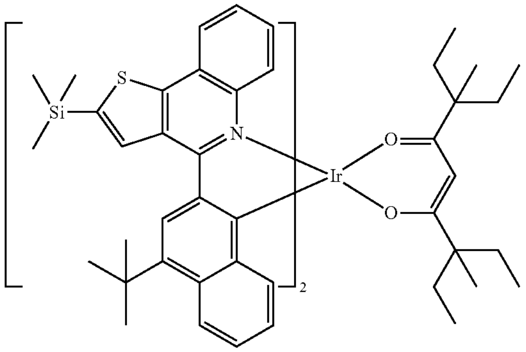
184
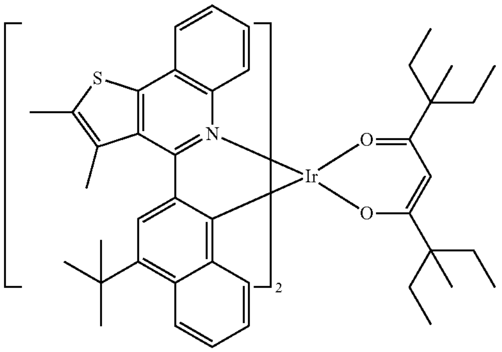
185
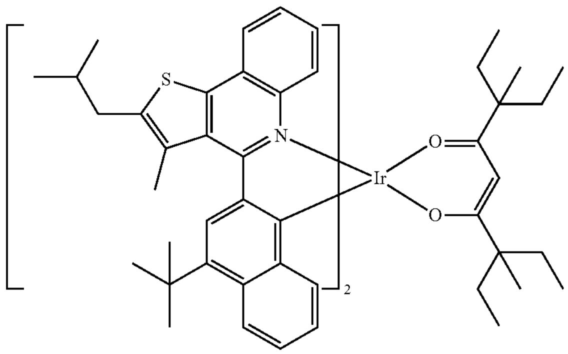
186
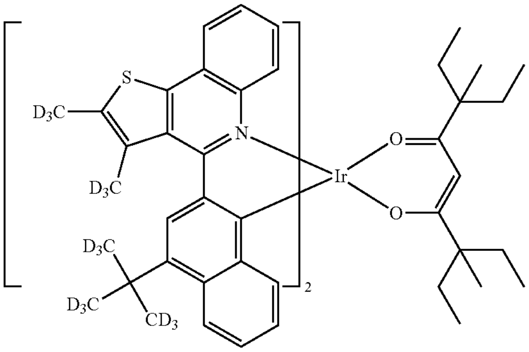
-continued
187
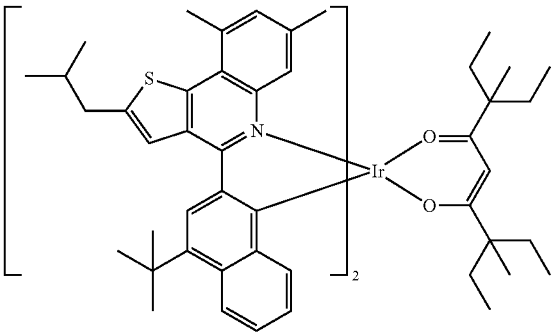
188
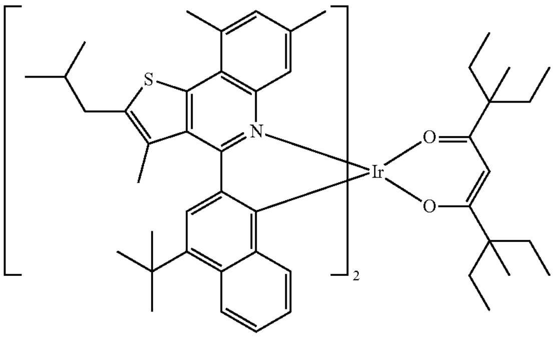
189
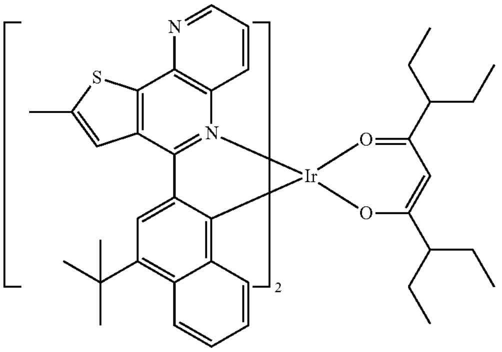
190
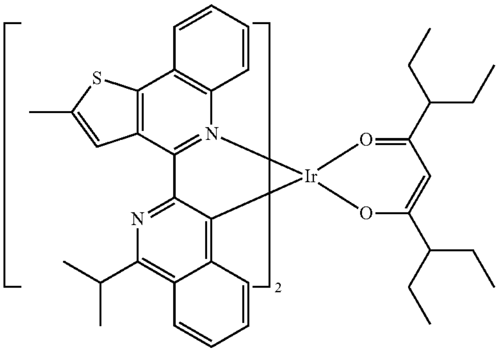

-continued
191
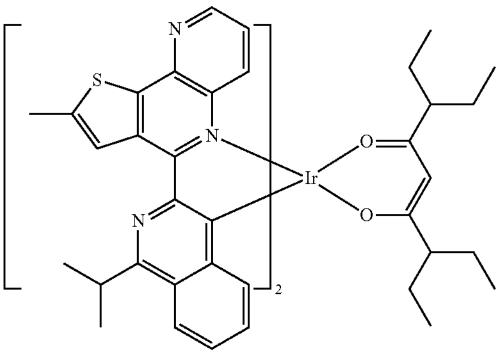
192
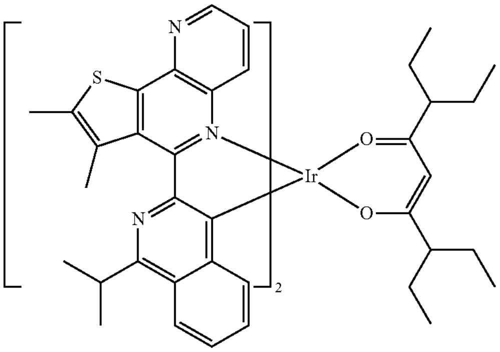
193
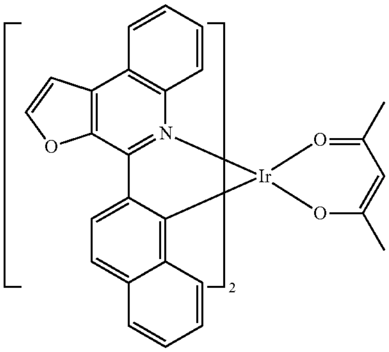
194
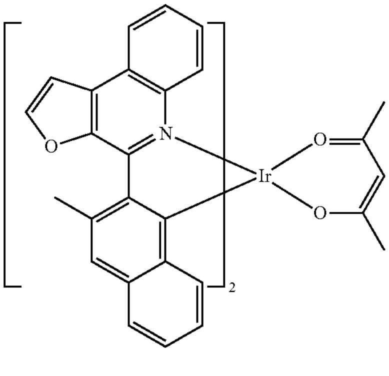
-continued
195
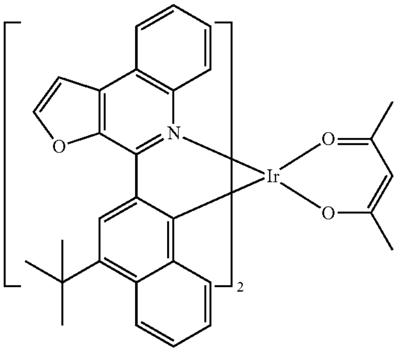
196
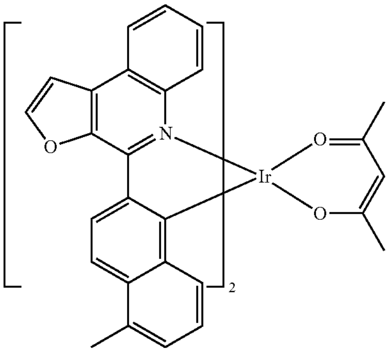
197
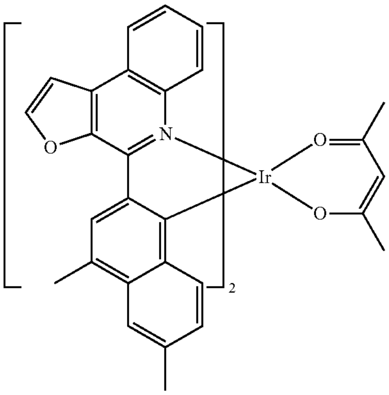
198
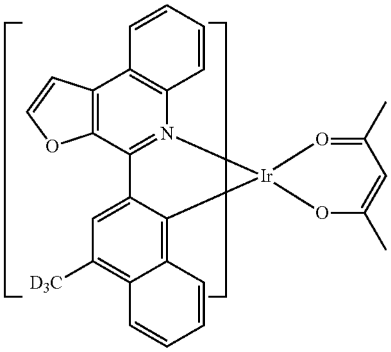

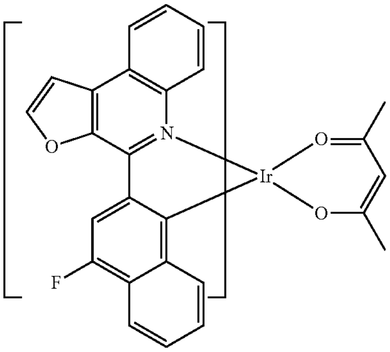
199
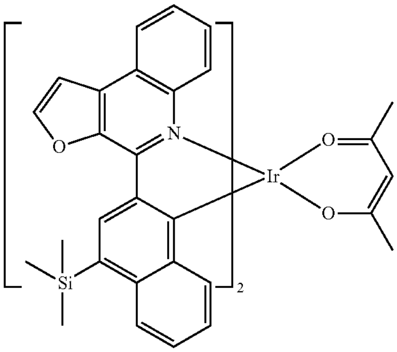
200
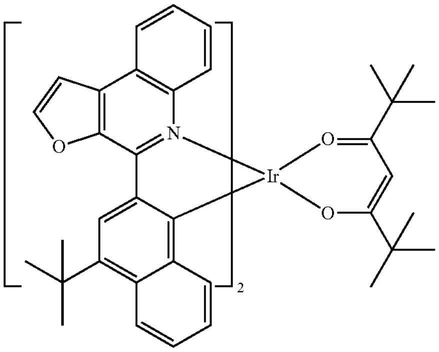
201
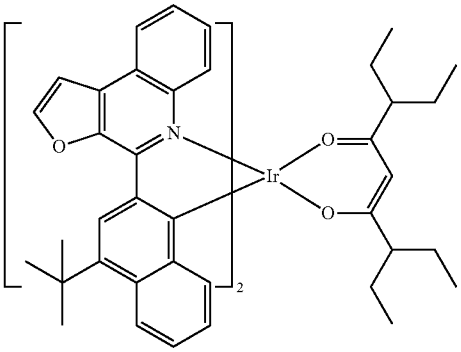
202
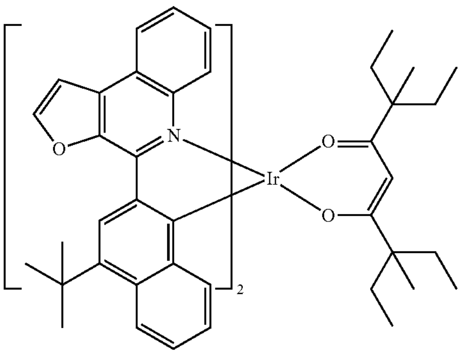
203
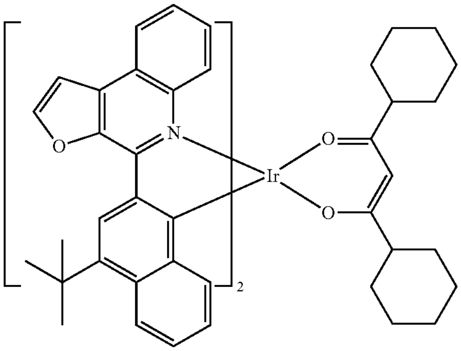
204
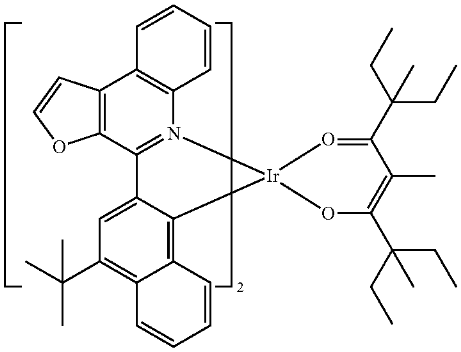
205
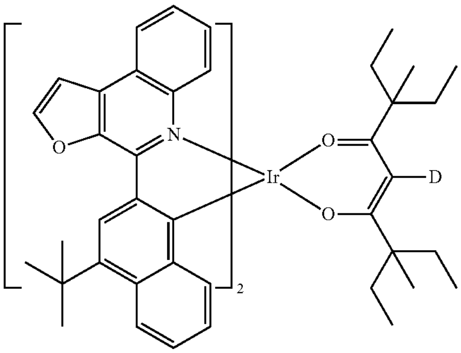
206

-continued
207
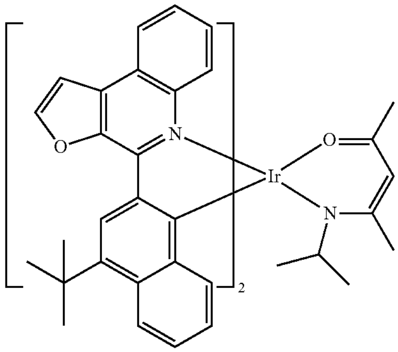
208
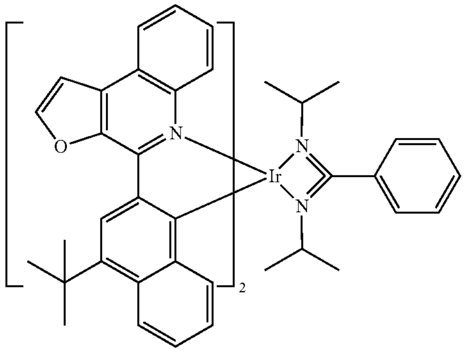
209
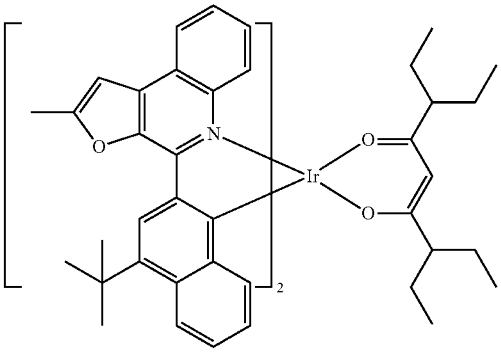
210
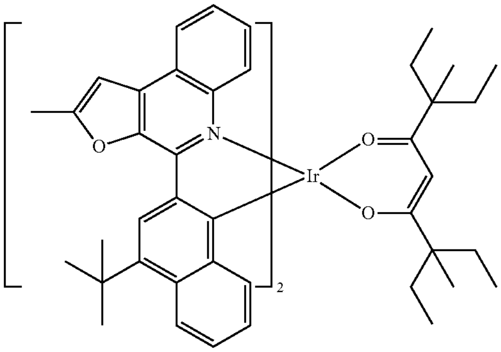
-continued
211
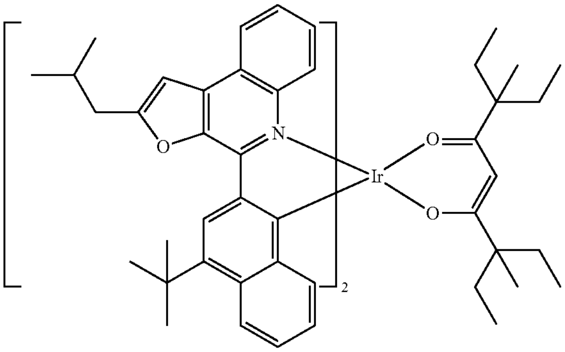
212
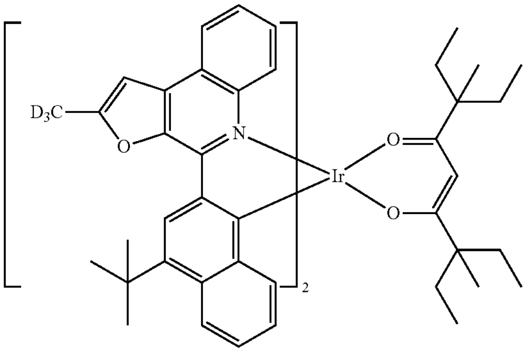
213
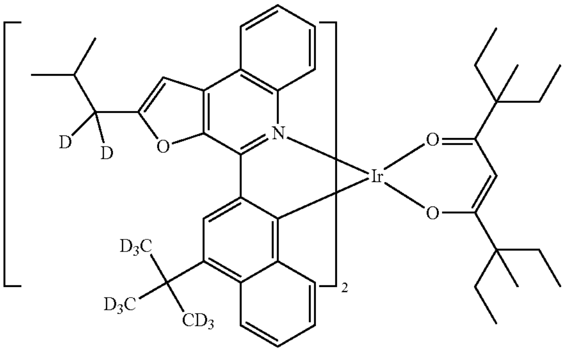
214
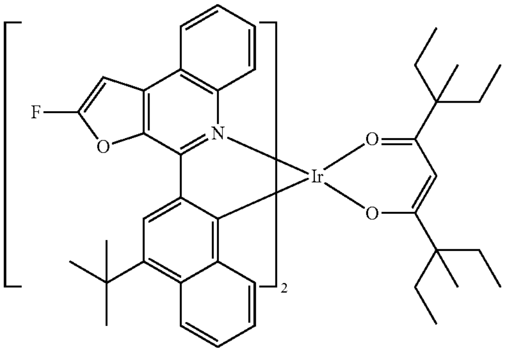

-continued
215
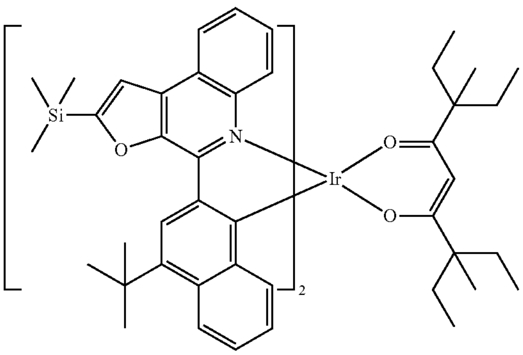
216
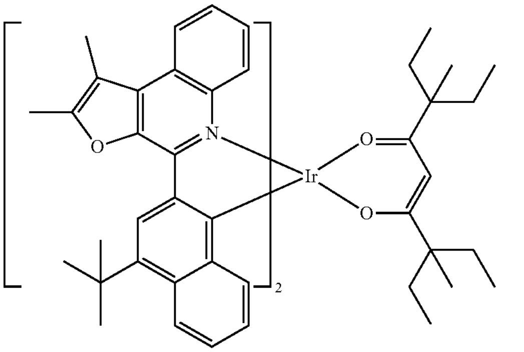
217
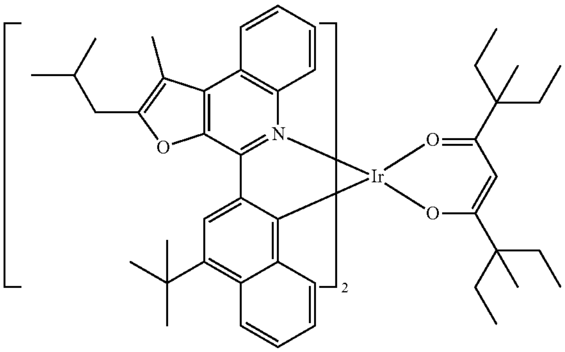
218
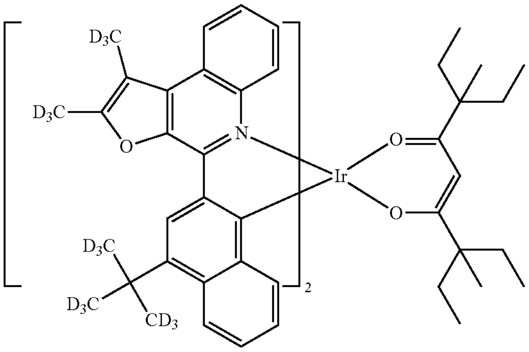
-continued
219
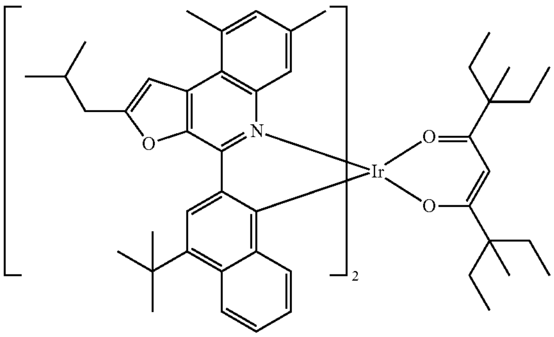
220
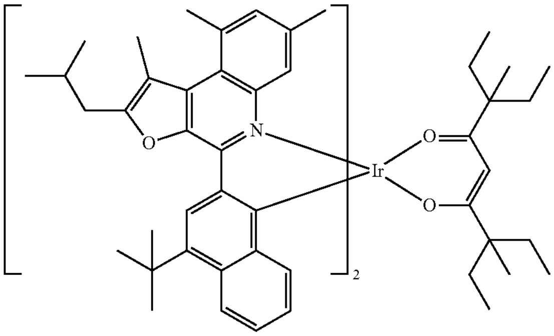
221
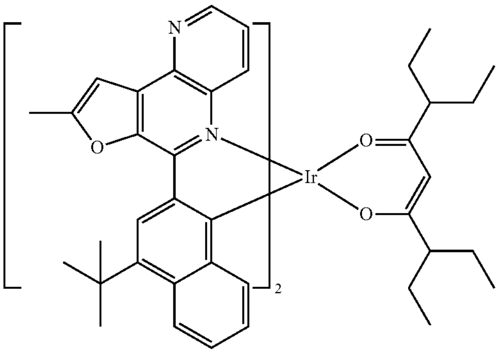
222
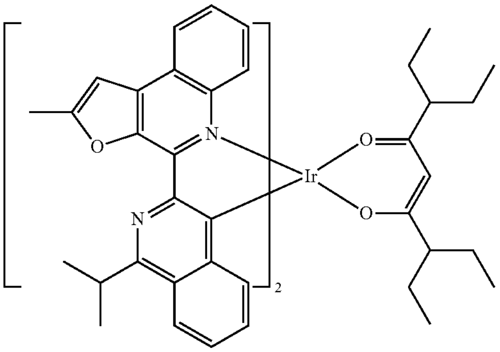

-continued
223
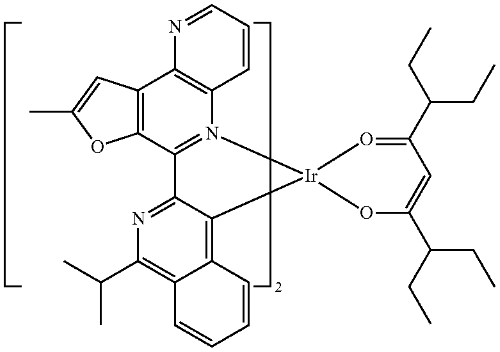
224
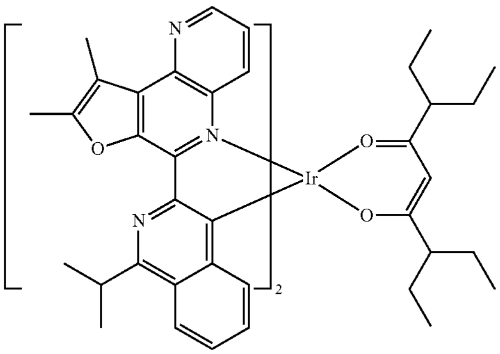
225
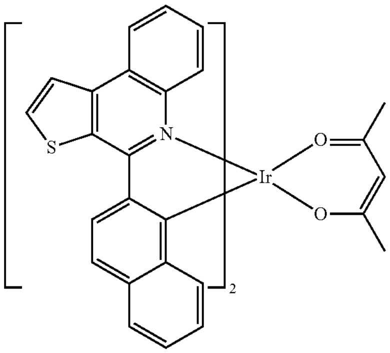
226
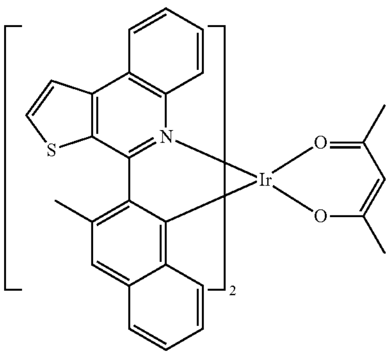
-continued
227
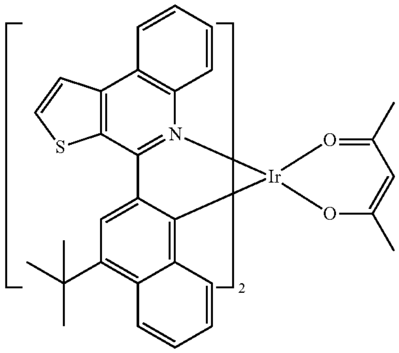
228
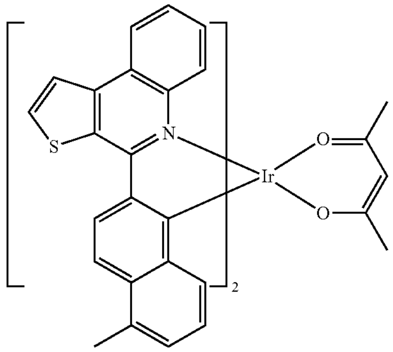
229
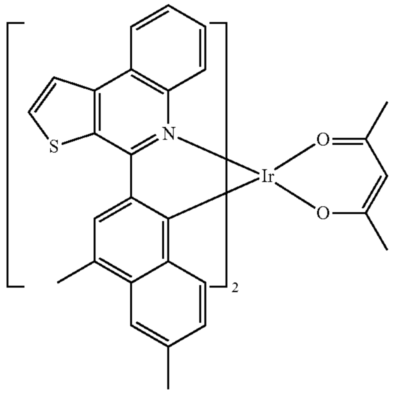
230
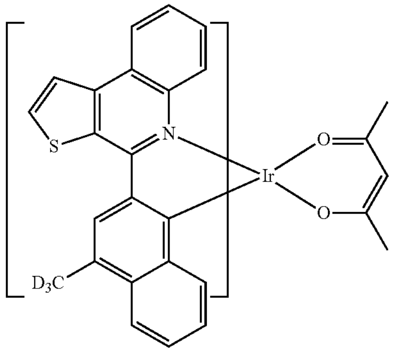

-continued
231
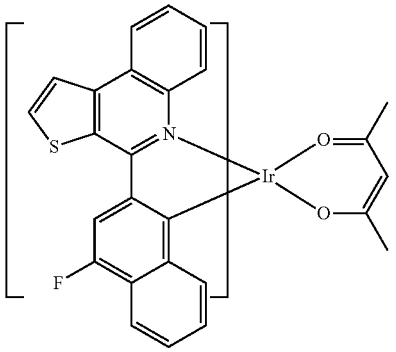
232
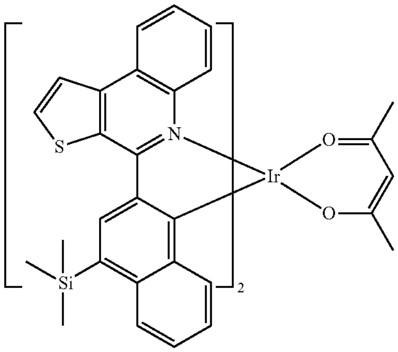
233
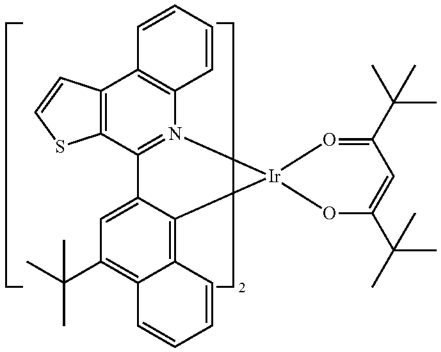
234
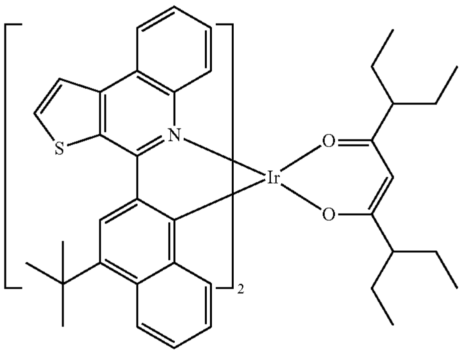
-continued
235
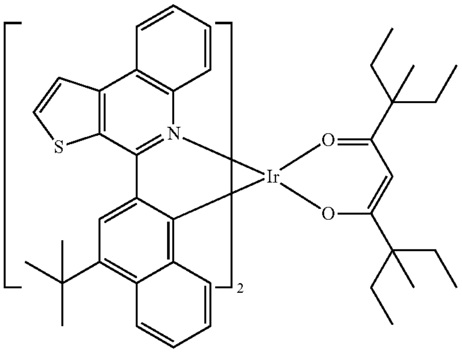
236
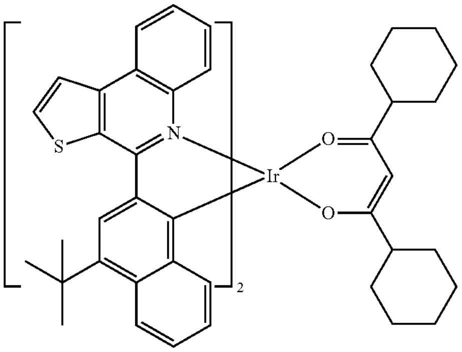
237
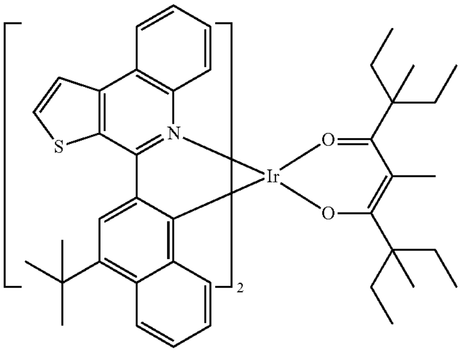
238
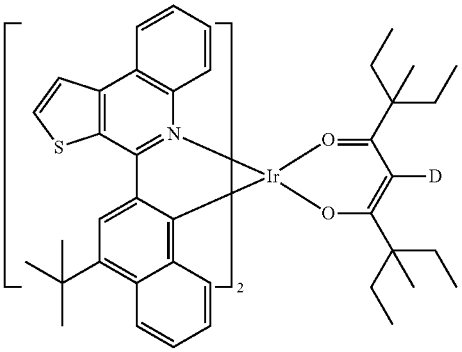

-continued
239
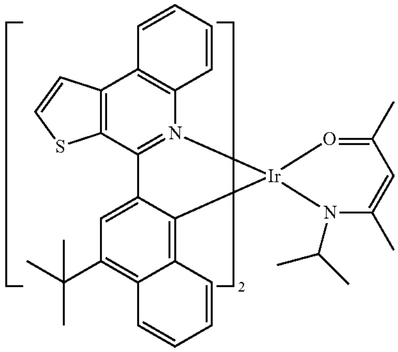
240
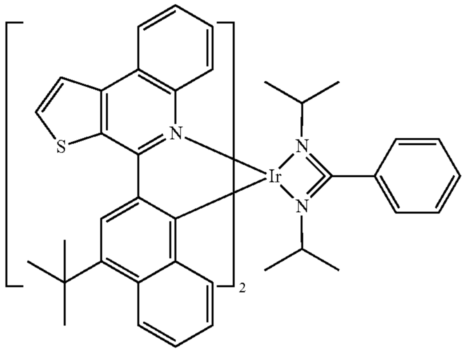
241
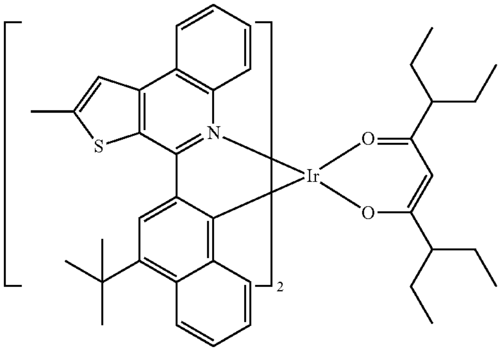
242
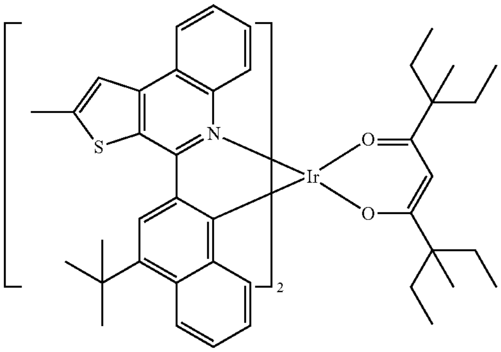
-continued
243
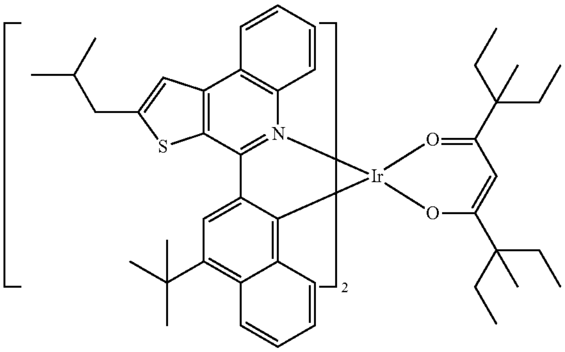
244
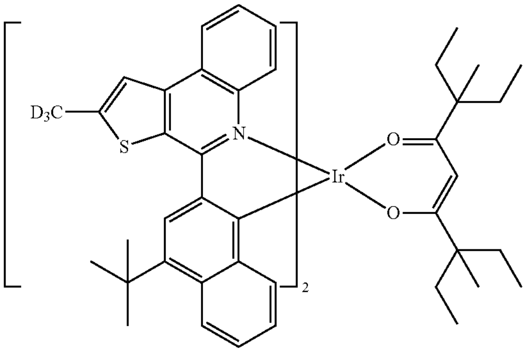
245
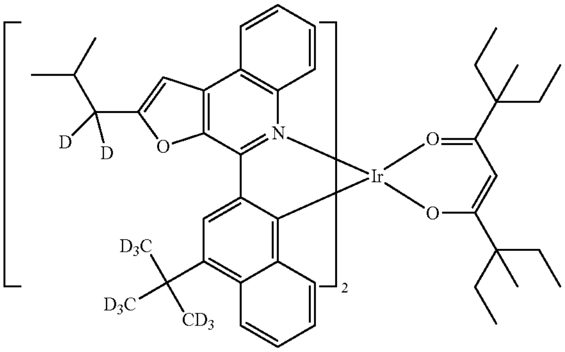
246
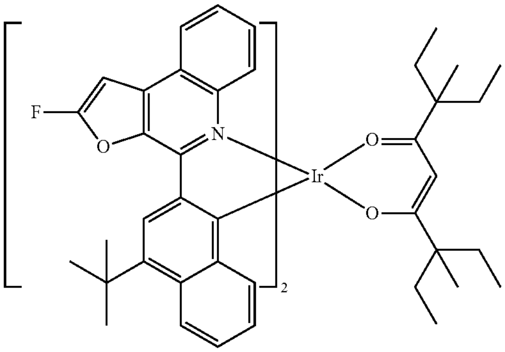

-continued
247
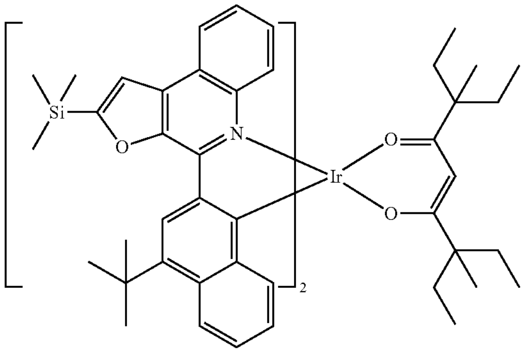
248
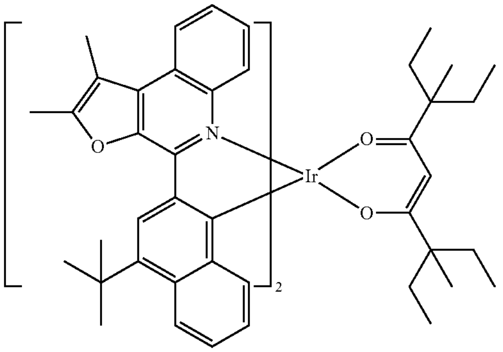
249
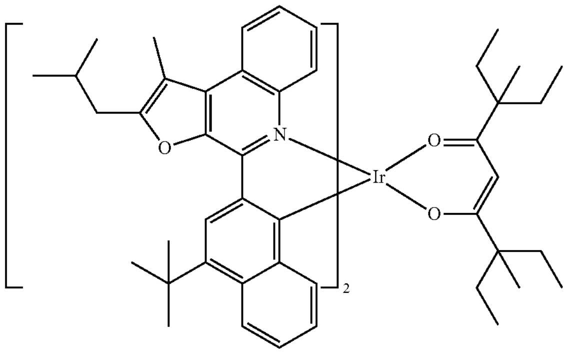
250
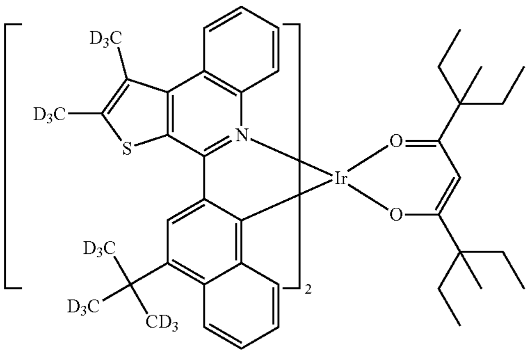
-continued
251
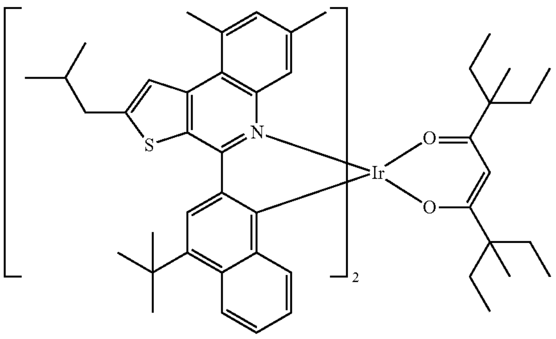
252
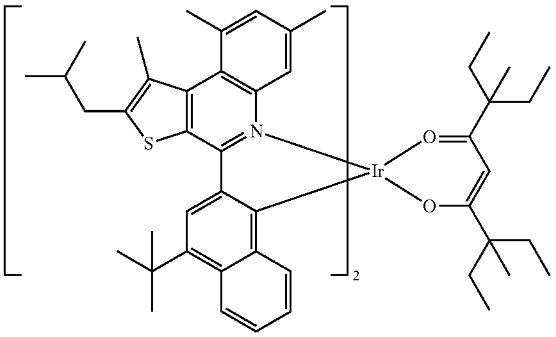
253
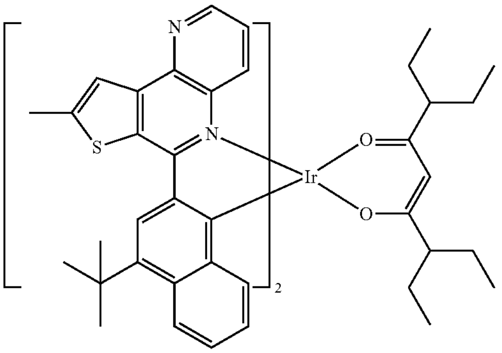
254
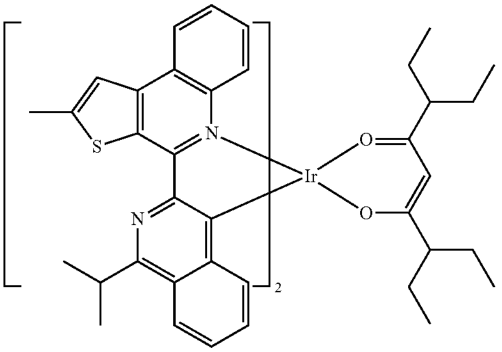

-continued
255
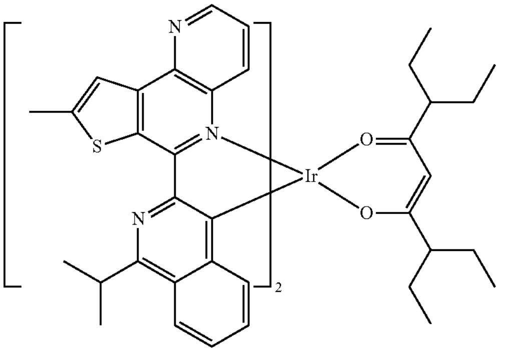
256
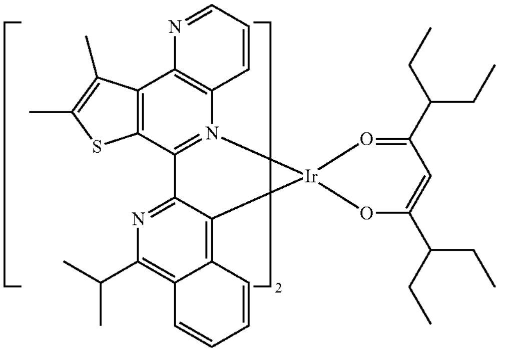
257
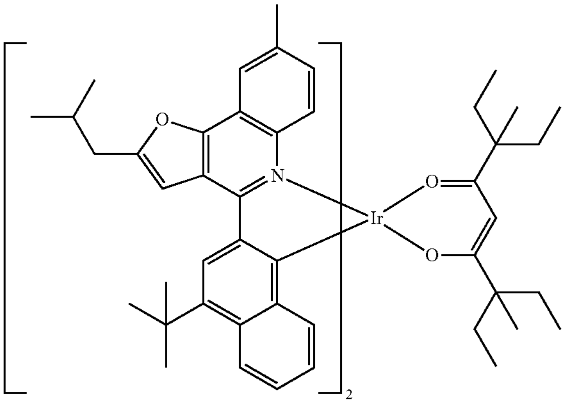
258
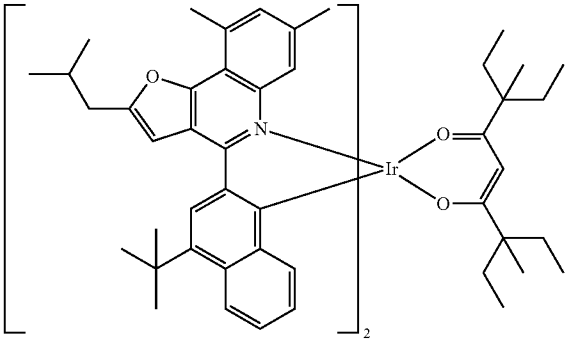
-continued
259
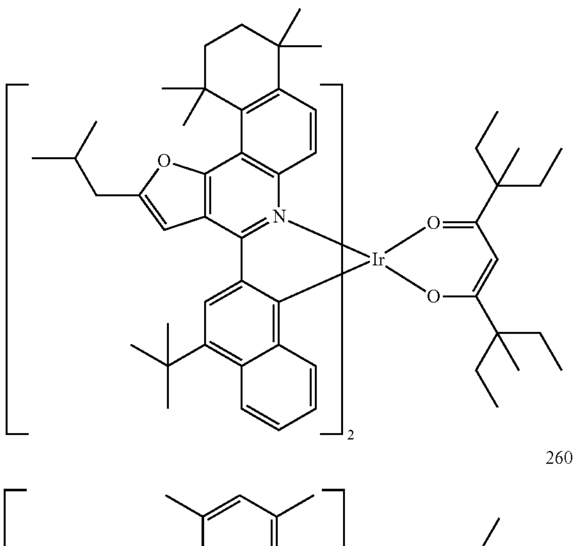
260
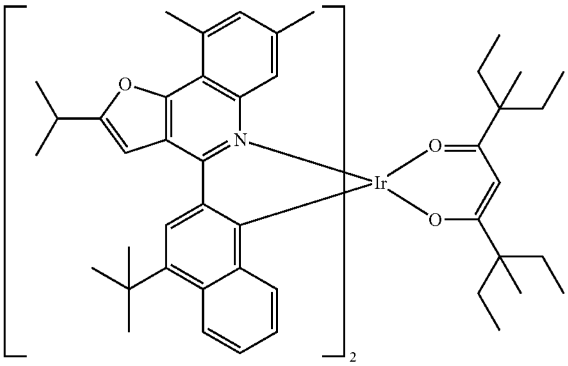
261
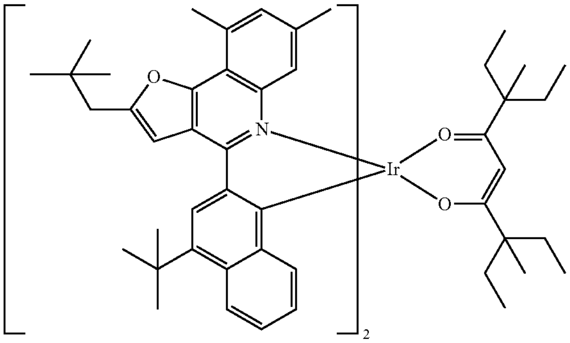
262
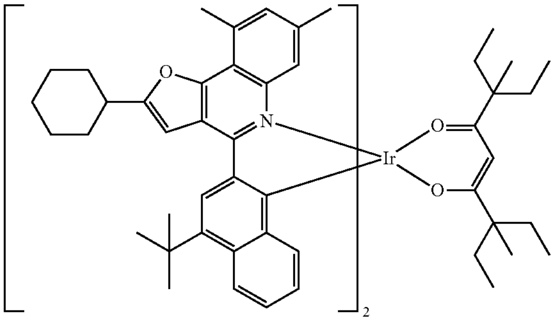

263
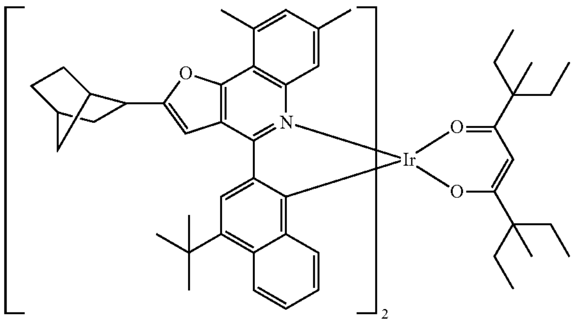
264
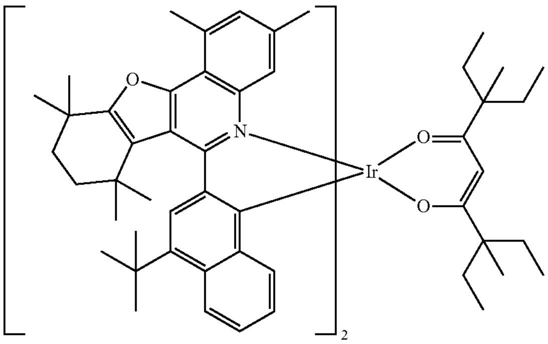
265
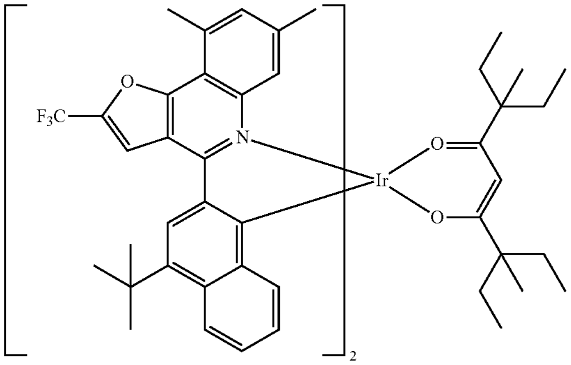
266
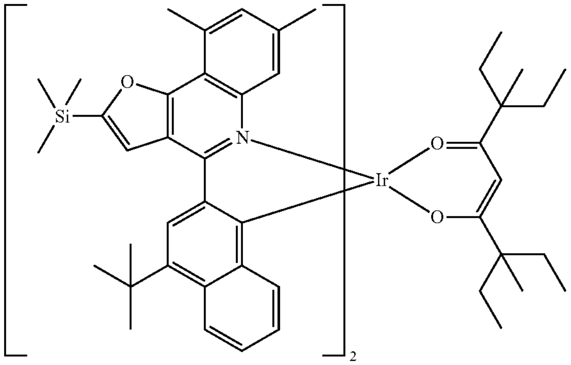
267
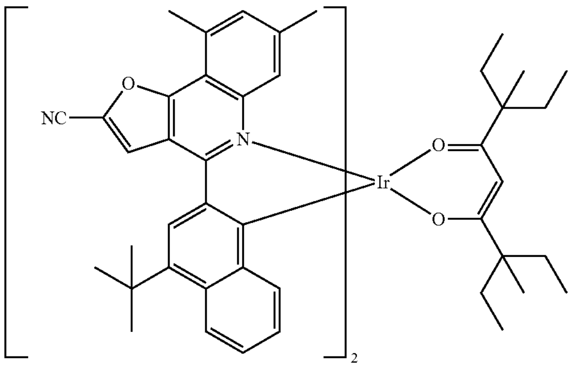
268
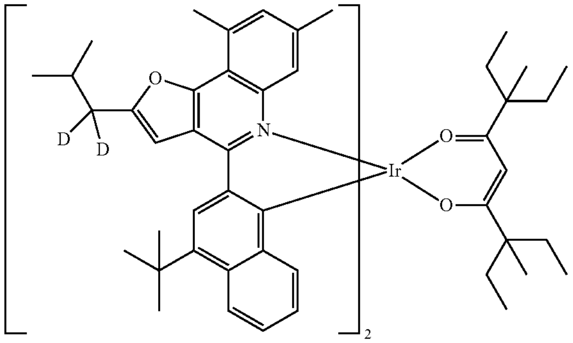
269
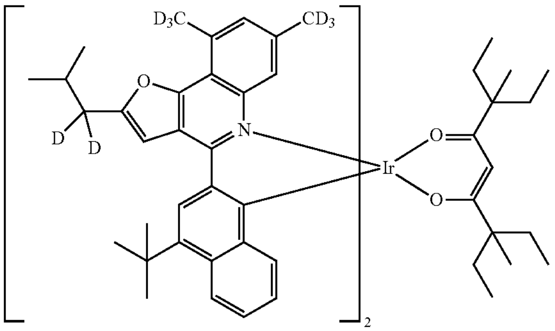
270
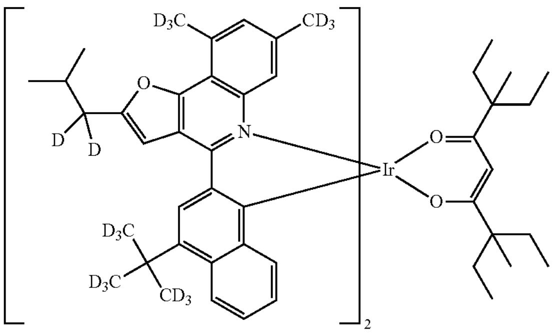

271
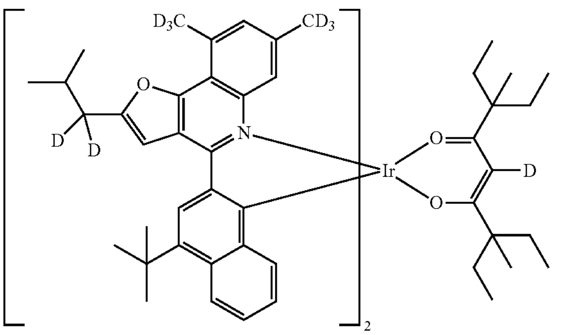
272
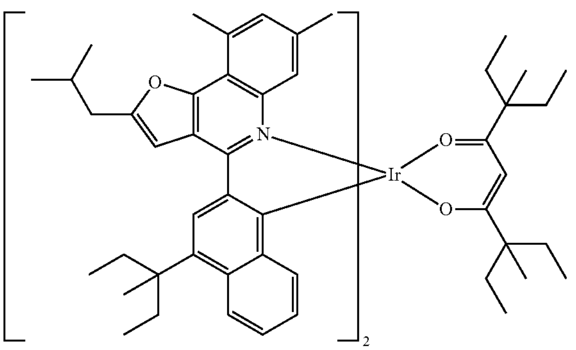
273
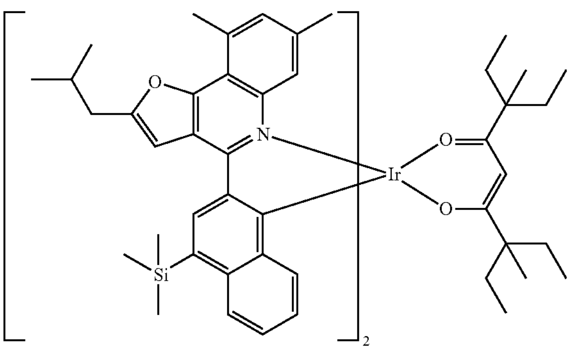
274
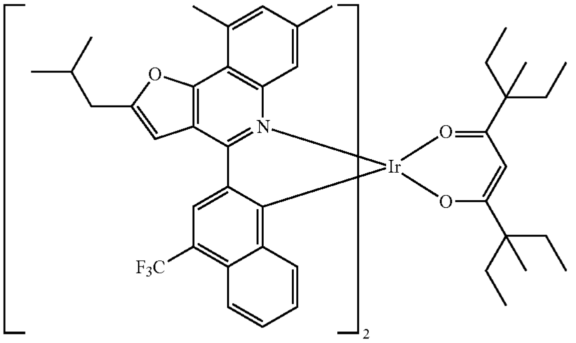
275
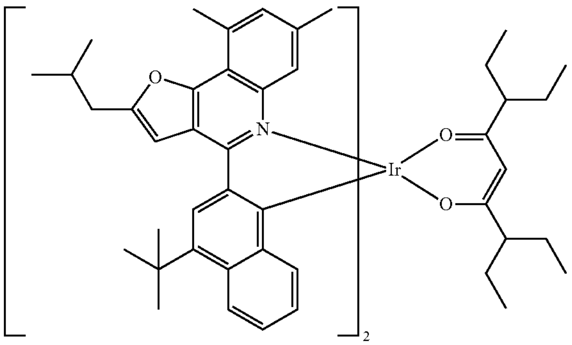
276
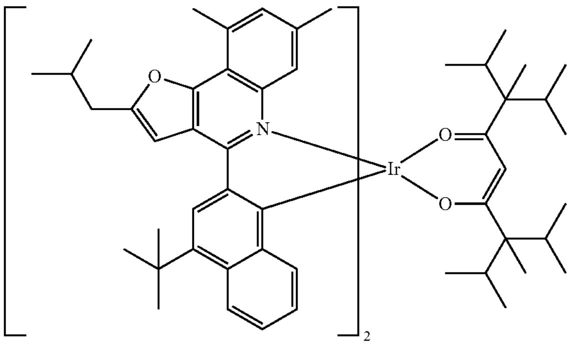
277
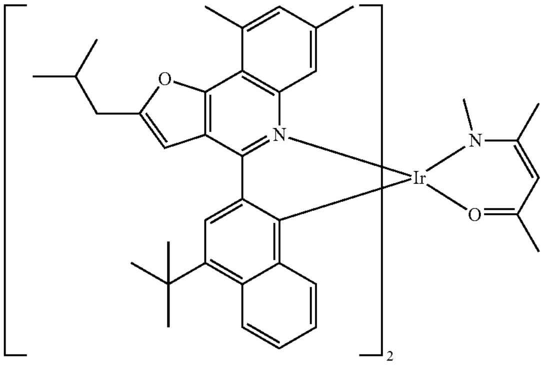
278
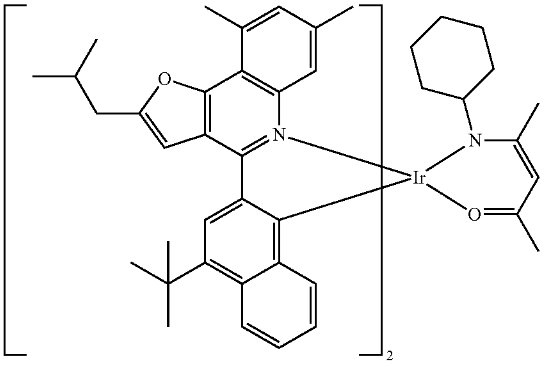

-continued
279
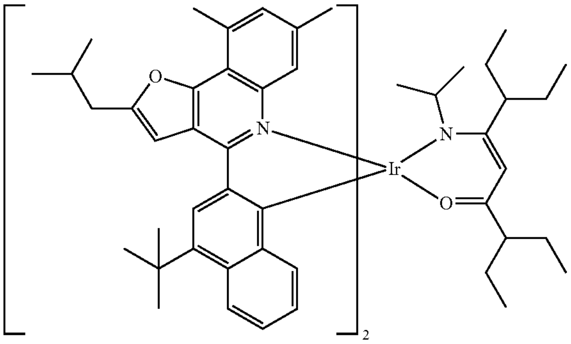
280
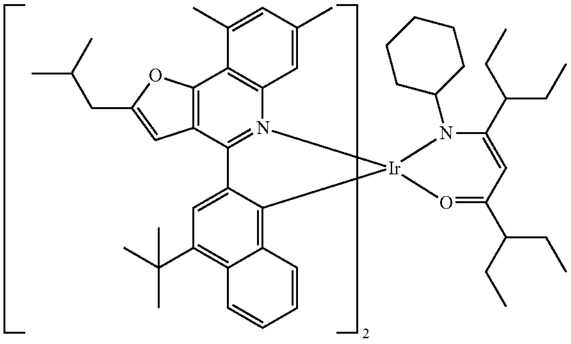
281
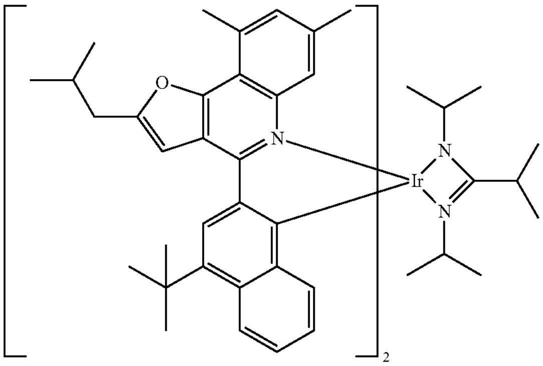
282
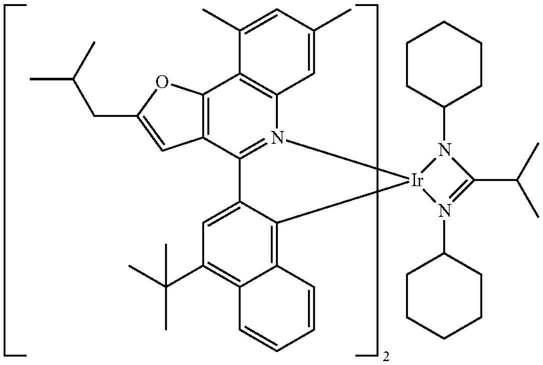
-continued
283
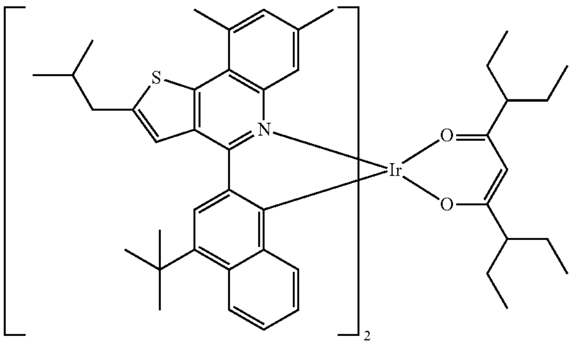
284
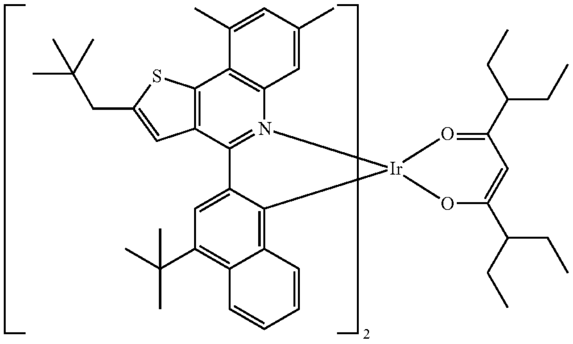
285
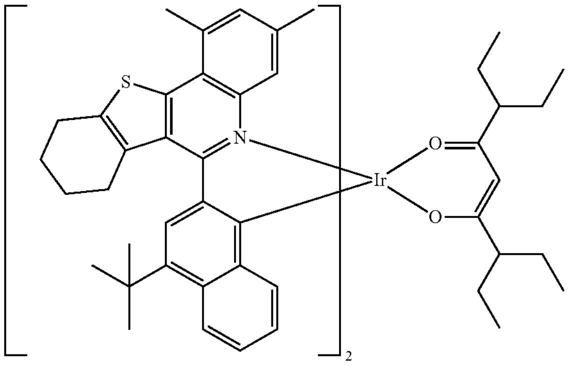
286
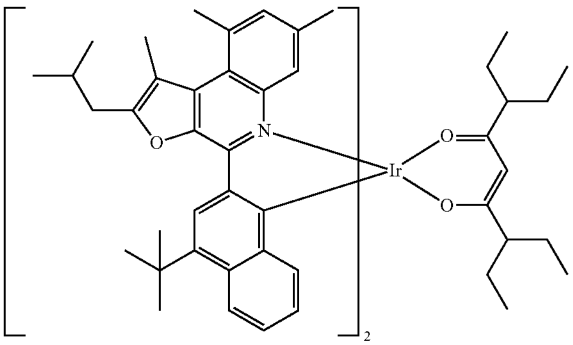

-continued

287

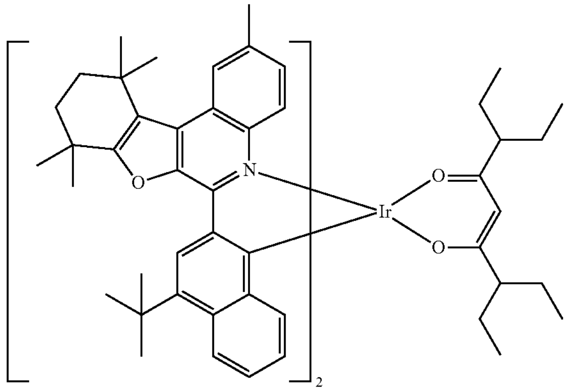

288

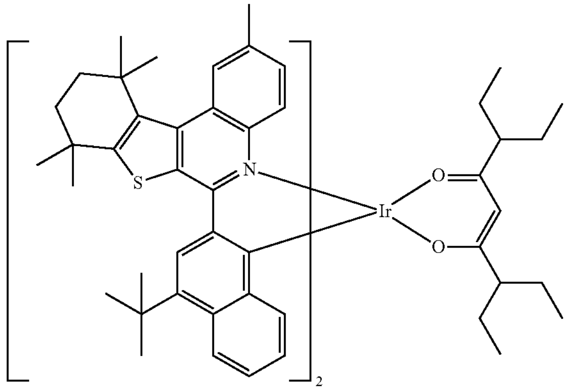

289

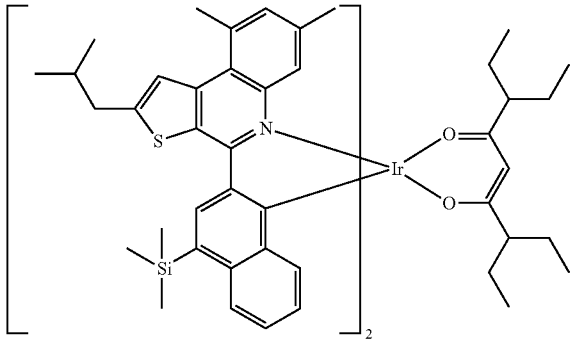

290

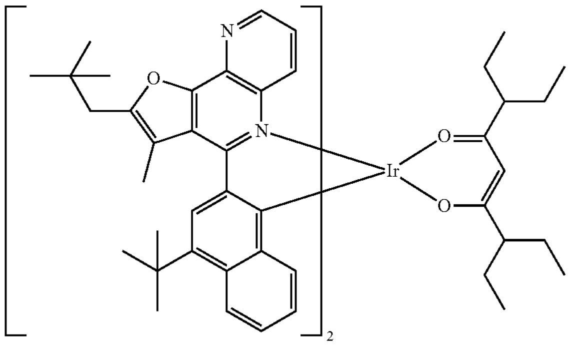

-continued

291

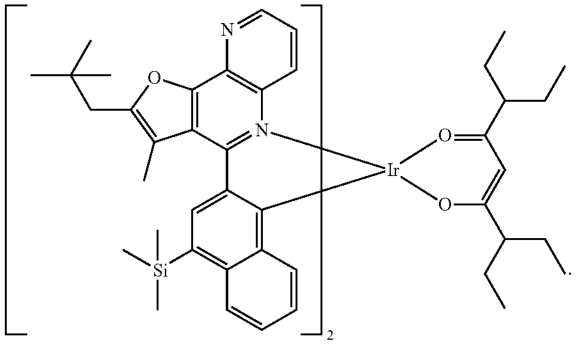

According to one implementation of the present disclosure, the organometallic compound represented by the Chemical Formula I of the present disclosure can be used as a red phosphorescent material or a green phosphorescent material.

Referring to FIG. 1 according to one implementation of the present disclosure, an organic electroluminescent device can be provided which includes a first electrode 110; a second electrode 120 facing the first electrode 110; and an organic layer 130 disposed between the first electrode 110 and the second electrode 120. The organic layer 130 can include a light-emitting layer 160, and the light-emitting layer 160 can include the organometallic compound represented by the Chemical Formula I. In addition, in the organic electroluminescent device, the organic layer 130 disposed between the first electrode 110 and the second electrode 120 can be formed by sequentially stacking a hole injection layer 140 (HIL), a hole transport layer 150, (HTL), a light emission layer 160 (EML), an electron transport layer 170 (ETL) and an electron injection layer 180 (EIL) on the first electrode 110. The second electrode 120 can be formed on the electron injection layer 180, and a protective layer can be formed thereon.

The first electrode 110 can act as a positive electrode, and can be made of ITO, IZO, tin-oxide, or zinc-oxide as a conductive material having a relatively large work function value. However, the present disclosure is not limited thereto.

The second electrode 120 can act as a negative electrode, and can include Al, Mg, Ca, Ag or the combination thereof as a conductive material having a relatively small work function value, or an alloy or combination thereof. However, the present disclosure is not limited thereto.

The hole injection layer 140 can be positioned between the first electrode 110 and the hole transport layer 150. A material of the hole injection layer 140 can include a compound selected from a group consisting of MTDATA, CuPc, TCTA, NPB(NPD), HATCN, TDAPB, PEDOT/PSS, N-(biphenyl-4-yl)-9,9-dimethyl-N-(4-(9-phenyl-9H-carbazol-3-yl)phenyl)-9H-fluoren-2-amine, NPNPB (N,N'-diphenyl-N,N'-di[4-(N,N-diphenyl-amino)phenyl]benzidine) and preferably can include NPNPB. However, the present disclosure is not limited thereto.

The hole transport layer 150 can be positioned adjacent to the light-emitting layer and between the first electrode 110 and the light-emitting layer 160. A material of the hole transport layer 150 can include a compound selected from a group consisting of TPD, NPD, CBP, N-(biphenyl-4-yl)-9,9-dimethyl-N-(4-(9-phenyl-9H-carbazol-3-yl)phenyl)-9H-fluoren-2-amine, N-(biphenyl-4-yl)-N-(4-(9-phenyl-9H-carbazol-3-yl)phenyl)biphenyl)-4-amine, etc. However, the present disclosure is not limited thereto.

According to the present disclosure, the light-emitting layer 160 can include a host and the organometallic compound represented by the Chemical Formula I as dopant doped into the host in order to improve luminous efficiency of the host and the organic electroluminescent device. The light-emitting layer 160 can be formed by adding about 1 to 30% by weight of the organometallic compound of the Chemical Formula I of the present disclosure to the host material, and can emit light of a green or red color.

For example, the light-emitting layer 160 can include the host material including one selected from a group consisting of CBP (carbazole biphenyl), mCP (1,3-bis(carbazol-9-yl), etc. However, the present disclosure is not limited thereto.

The electron transport layer 170 and the electron injection layer 180 can be sequentially stacked between the light-emitting layer 160 and the second electrode 120. A material of the electron transport layer 170 requires high electron mobility such that electrons can be stably supplied to the light-emitting layer under smooth electron transport.

For example, the material of the electron transport layer 170 can include a compound selected from a group consisting of Alq3 (tris(8-hydroxyquinolino)aluminum), Liq (8-hydroxyquinolinolatolithium), PBD (2-(4-biphenylyl)-5-(4-tert-butylphenyl)-1,3,4oxadiazole), TAZ (3-(4-biphenyl)4-phenyl-5-tert-butylphenyl-1,2,4-triazole), spiro-PBD, BAlq (bis(2-methyl-8-quinolinolate)-4-(phenylphenolato)aluminium), SAlq, TPBi (2,2',2-(1,3,5-benzinetriyl)-tris(1-phenyl-1-H-benzimidazole), oxadiazole, triazole, phenanthroline, benzoxazole, benzthiazole, ZADN (2-[4-(9,10-Di-naphthalen-2-yl-anthracen-2-yl)-phenyl]-1-phenyl-1H-benzoimidazole), and preferably can include ZADN. However, the present disclosure is not limited thereto.

The electron injection layer 180 serves to facilitate electron injection, and a material of the electron injection layer can include a compound selected from a group consisting of Alq3 (tris(8-hydroxyquinolino)aluminum), PBD, TAZ, spiro-PBD, BAlq, SAlq, etc. However, the present disclosure is not limited thereto. Alternatively, the electron injection layer 180 can be made of a metal compound. The metal compound can include, for example, one or more selected from a group consisting of Liq, LiF, NaF, KF, RbF, CsF, FrF, $BeF_2$, $MgF_2$, $CaF_2$, $SrF_2$, $BaF_2$ and $RaF_2$. However, the present disclosure is not limited thereto.

The organic electroluminescent device according to the present disclosure can be used as an organic light-emitting element of each of an organic light-emitting display device and a lighting device. In one implementation, FIG. 2 is a cross-sectional view schematically illustrating an organic light-emitting display device including the organic electroluminescent device according to some embodiments of the present disclosure as the organic light-emitting element thereof.

Figure 2:
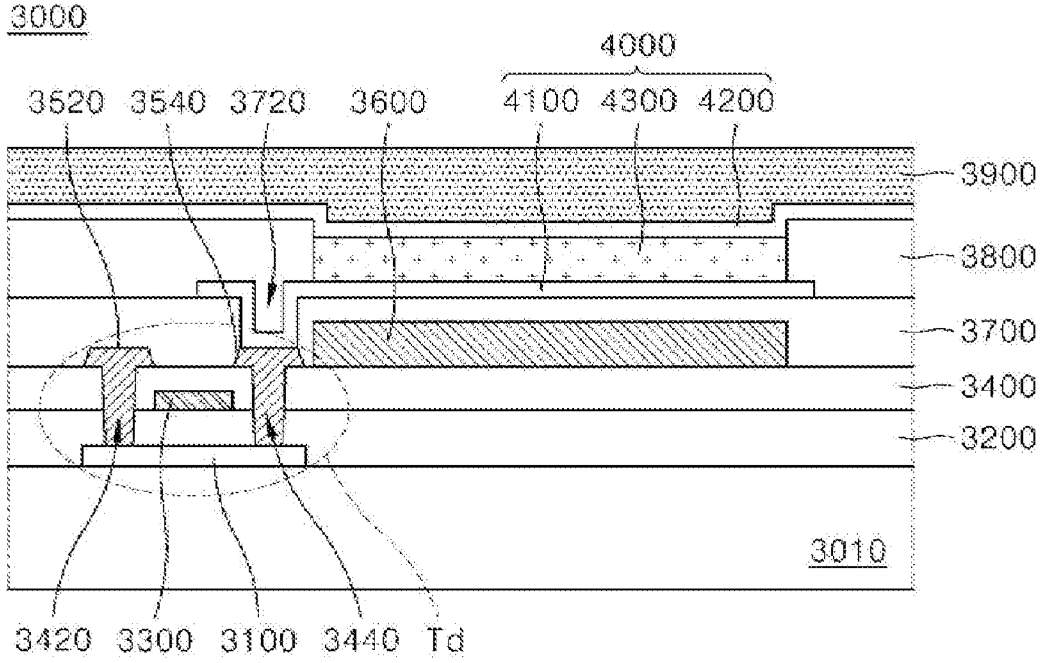
FIG. 2 is a cross-sectional view schematically illustrating an organic light-emitting display device including an organic electroluminescent device according to some embodiments of the present disclosure as an organic light-emitting element.

As shown in FIG. 2, an organic light-emitting display device 3000 includes a substrate 3010, an organic electroluminescent element 4000, and an encapsulation film 3900 covering the organic electroluminescent device 4000. A driving thin-film transistor Td as a driving element, and the organic electroluminescent element 4000 connected to the driving thin-film transistor Td are positioned on the substrate 3010.

Optionally, a gate line and a data line that intersect each other to define a pixel area, a power line extending parallel to and spaced from one of the gate line and the data line, a switching thin film transistor connected to the gate line and the data line, and a storage capacitor connected to one electrode of the thin film transistor and the power line are further formed on the substrate 3010.

The driving thin-film transistor Td is connected to the switching thin film transistor, and includes a semiconductor layer 3100, a gate electrode 3300, a source electrode 3520, and a drain electrode 3540.

The semiconductor layer 3100 can be formed on the substrate 3010 and can be made of an oxide semiconductor material or polycrystalline silicon. When the semiconductor layer 3100 is made of an oxide semiconductor material, a light-shielding pattern can be formed under the semiconductor layer 3100. The light-shielding pattern prevents light from being incident into the semiconductor layer 3100 to prevent the semiconductor layer 3010 from being deteriorated due to the light. Alternatively, the semiconductor layer 3100 can be made of polycrystalline silicon. In this case, both edges of the semiconductor layer 3100 can be doped with impurities.

The gate insulating layer 3200 made of an insulating material is formed over an entirety of a surface of the substrate 3010 and on the semiconductor layer 3100. The gate insulating layer 3200 can be made of an inorganic insulating material such as silicon oxide or silicon nitride.

The gate electrode 3300 made of a conductive material such as a metal is formed on the gate insulating layer 3200 and corresponds to a center of the semiconductor layer 3100. The gate electrode 3300 is connected to the switching thin film transistor.

The interlayer insulating layer 3400 made of an insulating material is formed over the entirety of the surface of the substrate 3010 and on the gate electrode 3300. The interlayer insulating layer 3400 can be made of an inorganic insulating material such as silicon oxide or silicon nitride, or an organic insulating material such as benzocyclobutene or photo-acryl.

The interlayer insulating layer 3400 has first and second semiconductor layer contact holes 3420 and 3440 defined therein respectively exposing both opposing sides of the semiconductor layer 3100. The first and second semiconductor layer contact holes 3420 and 3440 are respectively positioned on both opposing sides of the gate electrode 3300 and are spaced apart from the gate electrode 3300.

The source electrode 3520 and the drain electrode 3540 made of a conductive material such as metal are formed on the interlayer insulating layer 3400. The source electrode 3520 and the drain electrode 3540 are positioned around the gate electrode 3300, and are spaced apart from each other, and respectively contact both opposing sides of the semiconductor layer 3100 via the first and second semiconductor layer contact holes 3420 and 3440, respectively. The source electrode 3520 is connected to a power line.

The semiconductor layer 3100, the gate electrode 3300, the source electrode 3520, and the drain electrode 3540 constitute the driving thin-film transistor Td. The driving thin-film transistor Td has a coplanar structure in which the gate electrode 3300, the source electrode 3520, and the drain electrode 3540 are positioned on top of the semiconductor layer 3100.

Alternatively, the driving thin-film transistor Td can have an inverted staggered structure in which the gate electrode is disposed under the semiconductor layer while the source electrode and the drain electrode are disposed above the semiconductor layer. In this case, the semiconductor layer can be made of amorphous silicon. In one example, the switching thin-film transistor can have substantially the same structure as that of the driving thin-film transistor (Td).

In one example, the organic light-emitting display device 3000 can include a color filter 3600 absorbing the light generated from the electroluminescent element (light-emitting diode) 4000. For example, the color filter 3600 can absorb red (R), green (G), blue (B), and white (W) light. In this case, red, green, and blue color filter patterns that absorb light can be formed separately in different pixel areas. Each of these color filter patterns can be disposed to overlap each organic layer 4300 of the organic electroluminescent element 4000 to emit light of a wavelength band corresponding to each color filter. Adopting the color filter 3600 can allow the organic light-emitting display device 3000 to realize full-color.

For example, when the organic light-emitting display device 3000 is of a bottom emission type, the color filter 3600 absorbing light can be positioned on a portion of the interlayer insulating layer 3400 corresponding to the organic electroluminescent element 4000. In an optional embodiment, when the organic light-emitting display device 3000 is of a top emission type, the color filter can be positioned on top of the organic electroluminescent element 4000, that is, on top of a second electrode 4200. For example, the color filter 3600 can be formed to have a thickness of 2 to 5 μm.

In one example, a protective layer 3700 having a drain contact hole 3720 defined therein exposing the drain electrode 3540 of the driving thin-film transistor Td is formed to cover the driving thin-film transistor Td.

On the protective layer 3700, each first electrode 4100 connected to the drain electrode 3540 of the driving thin-film transistor Td via the drain contact hole 3720 is formed individually in each pixel area.

The first electrode 4100 can act as a positive electrode (anode), and can be made of a conductive material having a relatively large work function value. For example, the first electrode 410 can be made of a transparent conductive material such as ITO, IZO or ZnO.

In one example, when the organic light-emitting display device 3000 is of a top-emission type, a reflective electrode or a reflective layer can be further formed under the first electrode 4100. For example, the reflective electrode or the reflective layer can be made of one of aluminum (Al), silver (Ag), nickel (Ni), and an aluminum-palladium-copper (APC) alloy.

A bank layer 3800 covering an edge of the first electrode 4100 is formed on the protective layer 3700. The bank layer 3800 exposes a center of the first electrode 4100 corresponding to the pixel area.

An organic layer 4300 is formed on the first electrode 4100. If necessary, the organic electroluminescent element 4000 can have a tandem structure.

The second electrode 4200 is formed on the substrate 3010 on which the organic layer 4300 has been formed. The second electrode 4200 is disposed over the entirety of the surface of the display area and is made of a conductive material having a relatively small work function value and can be used as a cathode. For example, the second electrode 4200 can be made of one of aluminum (Al), magnesium (Mg), and an aluminum-magnesium alloy (AlMg).

The first electrode 4100, the organic layer 4300, and the second electrode 4200 constitute the organic electroluminescent element 4000.

An encapsulation film 3900 is formed on the second electrode 4200 to prevent external moisture from penetrating into the organic electroluminescent element 4000. Optionally, the encapsulation film 3900 can have a triple-layer structure in which a first inorganic layer, an organic layer, and an inorganic layer are sequentially stacked. However, the present disclosure is not limited thereto.

The organic electroluminescent device according to the present disclosure can act as a white light emitting diode having a tandem structure. The organic electroluminescent element having the tandem structure according to one implementation of the present disclosure can have a structure in which at least two unit light emitting elements are connected to each other via a charge generation layer (CGL). The organic electroluminescent element includes first and second electrodes facing each other and disposed on a substrate, and two or more light-emitting stacks vertically arranged between the first and second electrodes to emit light beams in specific wavelength bands, respectively. In this regard, the light-emitting layer can contain the organometallic compound represented by the Chemical Formula I according to the present disclosure as the dopant thereof. Adjacent ones of the plurality of light-emitting stacks in the tandem structure can be connected to each other via the charge generation layer (CGL) including an N-type charge generation layer and a P-type charge generation layer.

Figure 5:
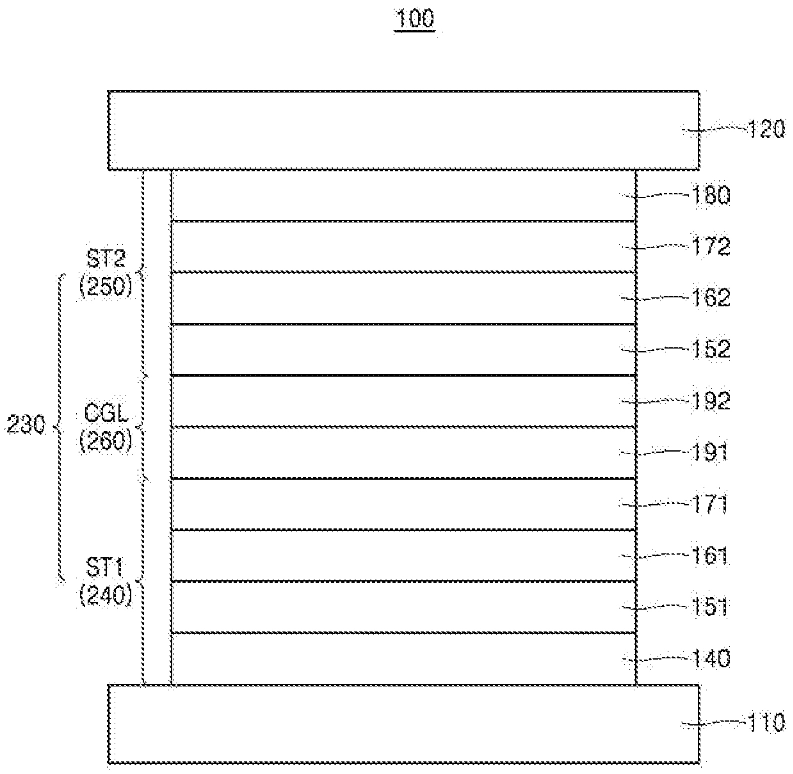
FIG. 5 is a cross-sectional view schematically illustrating an organic electroluminescent device having a tandem structure having two light-emitting stacks and including the organometallic compound represented by the Chemical Formula I according to some embodiments of the present disclosure.

FIG. 5 is a schematic cross-sectional view of an organic electroluminescent element in a tandem structure having two light-emitting stacks according to one implementation of the present disclosure. As shown in FIG. 5, the organic electroluminescent element 100 according to the present disclosure can include a first electrode 110 and a second electrode 120 facing each other, and an organic layer 230 positioned between the first electrode 110 and the second electrode 120. The organic layer 230 includes a first light-emitting stack (ST1) 240 positioned between the first electrode 110 and the second electrode 120 and including a first light-emitting layer 161; a second light-emitting stack (ST2) 250 positioned between the first light-emitting stack 240 and the second electrode 120 and including a second light-emitting layer 162; and a charge generation layer (CGL) 260) disposed between the first and second light-emitting stacks 240 and 250. The charge generation layer can include an N-type charge generation layer 191 and a P-type charge generation layer 192.

Further, the organic electroluminescent element according to one implementation of the present disclosure can have a tandem structure having three light-emitting stacks. Alternatively, four or more light-emitting stacks and three or more charge generating layers can be disposed between the first electrode and the second electrode.

Hereinafter, Synthesis Example and Present Example of the present disclosure will be described. However, following Present Example is only one example of the present disclosure.

The present disclosure is not limited thereto.

Synthesis Example

<Preparation of Compound A1>

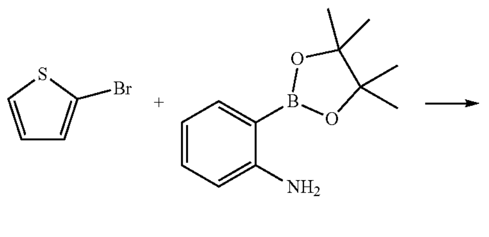

-continued

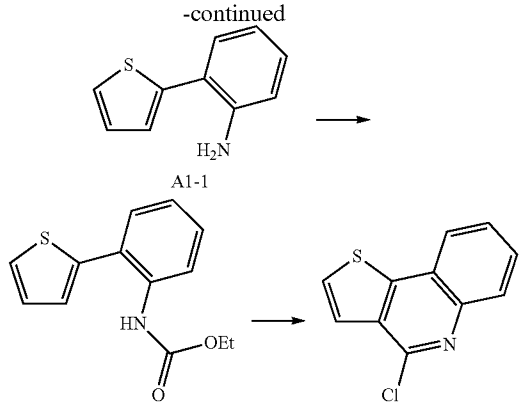

A1-1

A1-2

A1

Step 1) Preparation of Compound A1-1

In a reaction vessel, 2-bromothiophene (25.6 g, 157.14 mmol), 2-(4,4,5,5-tetramethyl-1,3,2-dioxaborolan-2-yl)aniline (41.6 g, 190.01 mmol), $Pd(PPh_3)_4$ (9.2 g, 7.92 mmol) and $NaHCO_3$ (39.9 g, 288.76 mmol) were dissolved in 1,4-dioxane (500 ml) and distilled water (100 ml) and the mixture was refluxed for 15 hours. After completion of the reaction, the mixture was cooled down to room temperature and extraction was performed using MC (methylene chloride) and distilled water. $MgSO_4$ was added to an organic layer to remove moisture, and then the solvent was removed via filtration under reduced pressure. Column chromatography was performed with hexane and MC Thus, the compound A1-1 (26.8 g, yield 96%) was obtained.

MS (m/z): 175.25

Step 2) Preparation of Compound A1-2

A1-1 (26.8 g, 152.64 mmol), ethyl chloroformate (5.16 ml, 53.92 mmol) and $K_2CO_3$ (40.6 g, 305.28 mmol) were dissolved in chloroform (500 ml) in a reaction vessel and the mixture was refluxed for 18 hours. After completion of the reaction, the mixture was cooled down to room temperature and then extraction was performed using MC and distilled water. $MgSO_4$ was added to an organic layer to remove moisture, and then the solvent was removed via filtration under reduced pressure. Column chromatography was performed with hexane and MC. Thus, the compound A1-2 (36.71 g, yield 97%) was obtained.

MS (m/z): 247.31

Step 3) Preparation of Compound A1

A1-2 (33.3 g, 134.9 mmol), $POCl_3$ (126 ml, 1346.89 mmol) and 30 ml of TEA were added to the reaction vessel and the mixture was refluxed for 16 hours. The reaction solution was cooled down to room temperature, and extraction was performed using MC and distilled water. $MgSO_4$ was added to an organic layer to remove moisture, and then the solvent was removed via filtration under reduced pressure. The mixture was dissolved in EA, was filtered through silica gel, and then was filtered under reduced pressure to remove the solvent. The obtained solid was treated with hexane to obtain the compound A1 (11.2 g, yield 38%) in a form of an ivory solid.

MS (m/z): 219.69

<Preparation of Compound A2>

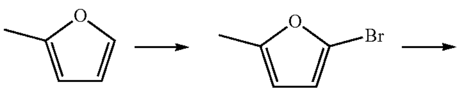

A2-1

-continued

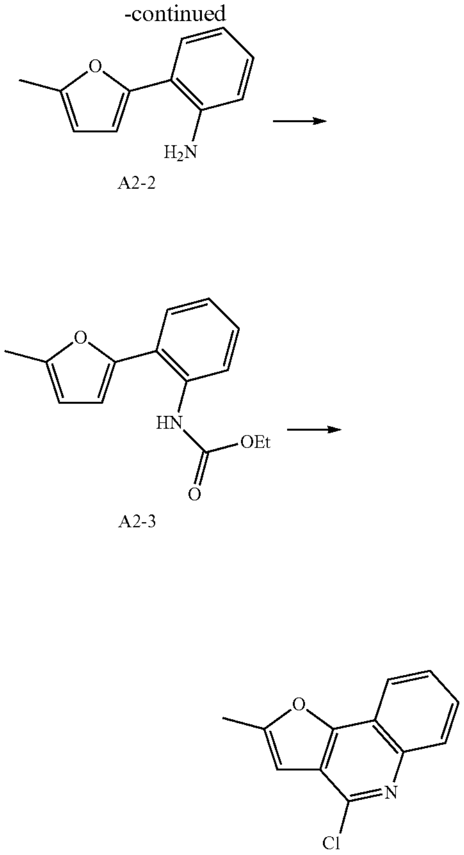

A2-2

A2-3

A2

Step 1) Preparation of Compound A2-1

In a reaction vessel, 2-methylfuran (30.1 g, 366.626 mol) was dissolved in chloroform, the temperature was lowered to −20° C., and NBS (65.3 g, 366.626 mmol) was slowly added thereto dropwise. A temperature of the reaction solution was raised up to room temperature, and the reaction solution was stirred for 30 minutes. After completion of the reaction, extraction was performed using MC and distilled water. $MgSO_4$ was added to an organic layer to remove moisture, and then the solvent was removed via filtration under reduced pressure. The mixture was dissolved in hexane and was filtered through silica gel to obtain the compound A2-1 (39 g, yield 66%) in a transparent liquid form.

MS (m/z): 161.00

Step 2) Preparation of Compound A2-2

A2-1 (33.2 g, 206.40 mmol), 2-(4,4,5,5-tetramethyl-1,3,2-dioxaborolan-2-yl)aniline (54.3 g, 247.68 mmol), $Pd(PPh_3)_4$ (11.9 g, 10.32 mmol) and $NaHCO_3$ (85.6 g, 619.19 mmol) were dissolved in 1,4-dioxane (500 ml) and distilled water (100 ml) and the mixture was refluxed for 15 hours. After completion of the reaction, the mixture was cooled down to room temperature and then extraction was performed using MC and distilled water. $MgSO_4$ was added to an organic layer to remove moisture, and then the solvent was removed via filtration under reduced pressure. Column chromatography was performed with hexane and MC. Thus, the compound A2-2 (17.7 g, yield 49%) was obtained.

MS (m/z): 173.21

Step 3) Preparation of Compound A2-3

A2-2 (17.7 g, 102.02 mmol), ethyl chloroformate (11.7 ml, 122.42 mmol) and $K_2CO_3$ (28.2 g, 204.03 mmol) were dissolved in chloroform (300 ml) in a reaction vessel and the mixture was refluxed for 18 hours. After completion of the reaction, the mixture was cooled down to room temperature and then extraction was performed using MC and distilled water. $MgSO_4$ was added to an organic layer to remove moisture, and then the solvent was removed via filtration under reduced pressure. Column chromatography was performed with hexane and MC. Thus, the compound A2-3 (20.6 g, yield 82%) was obtained.

MS (m/z): 245.27

Step 4) Preparation of Compound A2

A2-3 (20.6 g, 83.99 mmol), $POCl_3$ (78.5 ml, 839.89 mmol) and 20 ml of TEA were added to the reaction vessel and the mixture was refluxed for 16 hours. The reaction solution was cooled down to room temperature, and extraction was performed using MC and distilled water. $MgSO_4$ was added to an organic layer to remove moisture, and then the solvent was removed via filtration under reduced pressure. The mixture was dissolved in EA, filtered through silica gel, and filtered under reduced pressure to remove the solvent. The obtained solid was treated with hexane to obtain the compound A2 (8.4 g, yield 46%) in a form of an ivory solid.

MS (m/z): 217.65

<Preparation of Compound B1>

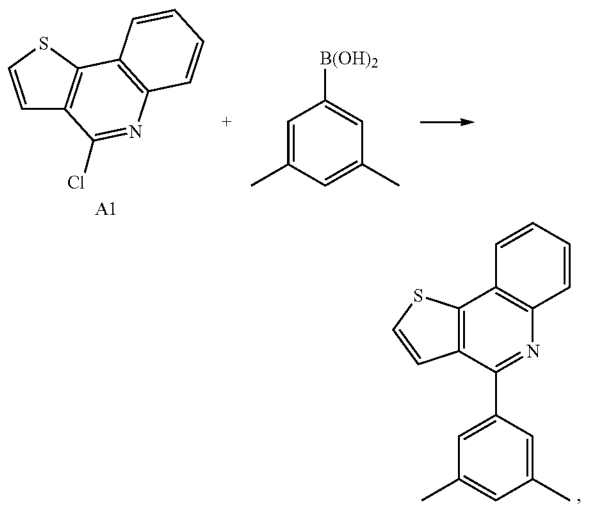

A1

B1

In a reaction vessel, A1 (11 g, 50.07 mmol), (3,5-dimethylphenyl)boronic acid (8.3 g, 55.08 mmol), $Pd(PPh_3)_4$ (5.7 g, 5.01 mmol) and $K_2CO_3$ (13.8 g, 100.14 mmol) were dissolved in 1,4-dioxane (150 ml) and distilled water (30 ml) and the mixture was refluxed for 16 hours. After completion of the reaction, the mixture was cooled down to room temperature and then extraction was performed using MC and distilled water. $MgSO_4$ was added to an organic layer to remove moisture, and then the solvent was removed via filtration under reduced pressure. Column chromatography was performed with hexane and MC. Thus, the compound B1 (10.6 g, yield 73%) was obtained.

MS (m/z): 289.39

<Preparation of Compound B2>

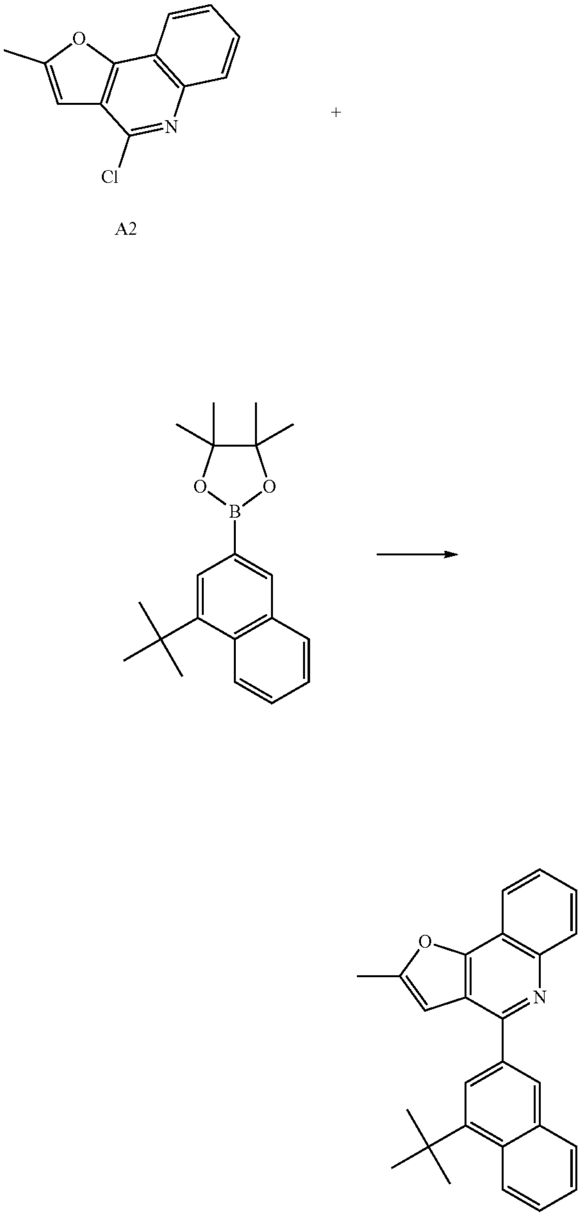

A2

B2

In a reaction vessel, A2 (8 g, 36.77 mmol), 2-(4-(tert-butyl)naphthalen-2-yl)-4,4,5,5-tetramethyl-1,3,2-dioxaborolane (12.5 g, 40.43 mmol), $Pd(PPh_3)_4$ (4.2 g, 3.68 mmol) and $K_2CO_3$ (10.2 g, 73.51 mmol) were dissolved in 1,4-dioxane (120 ml) and distilled water (24 ml) and the mixture was refluxed for 16 hours. After completion of the reaction, the mixture was cooled down to room temperature and then extraction was performed using MC and distilled water. $MgSO_4$ was added to an organic layer to remove moisture, and then the solvent was removed via filtration under reduced pressure. Column chromatography was performed with hexane and MC. Thus, the compound B2 (9.8 g, yield 73%) was obtained.

MS (m/z): 365.47

<Preparation of Compound 42>

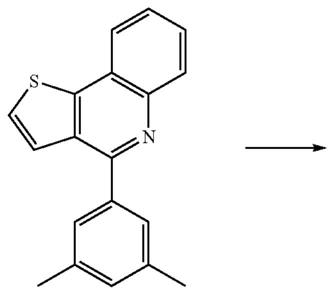

B1

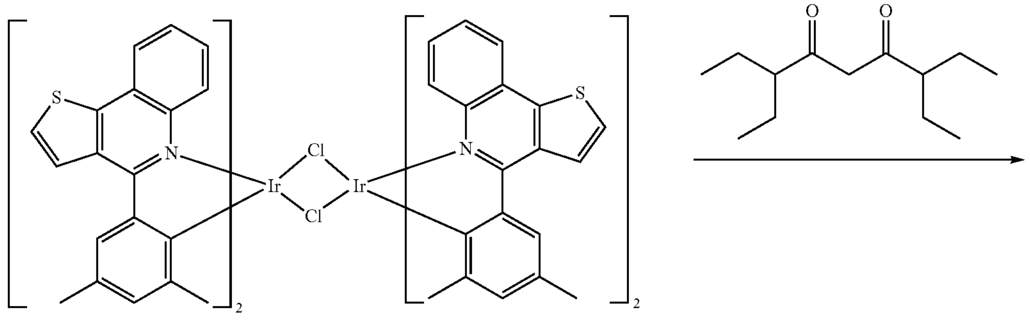

C1

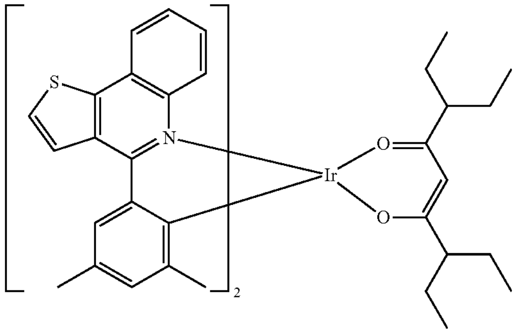

Compound 42

Preparation of Compound C1

B1 (10 g, 34.55 mmol), 2-ethoxyethanol 200 ml, and distilled water 66 ml were added to the reaction vessel, followed by nitrogen bubbling for 1 hour. Then, $IrCl_3 \cdot H_2Ox$ (6.1 g, 15.71 mmol) was added thereto and the mixture was refluxed for 24 hours. After the reaction was completed, the temperature was slowly lowered to room temperature and the resulting solid was filtered. The filtered solid was washed with methanol and dried to obtain the compound C1 (10.1 g, yield 80%).

Preparation of Compound 42

C1 (10.1 g, 6.28 mmol), 3,7-diethylnonane-4,6-dione (12.7 g, 59.64 mmol), $Na_2CO_3$ (13 g, 122.46 mmol), and 300 ml of 2-ethoxyethanol were added to the reaction vessel and the mixture was slowly stirred for 24 hours. After the reaction was completed, dichloromethane was added to the reaction product to dissolve the reaction product, and then extraction was performed with dichloromethane and distilled water. Water in an organic layer was removed using $MgSO_4$, and then the solvent was removed via filtration under reduced pressure. Column chromatography was performed with hexane and dichloromethane to obtain the compound 42 (5.2 g, yield 43%).

MS (m/z): 966.28

<Preparation of Compound 5>
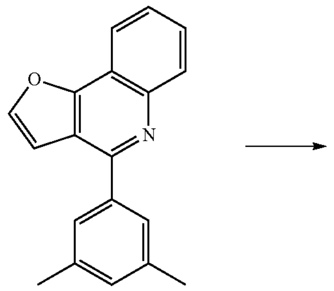
B3
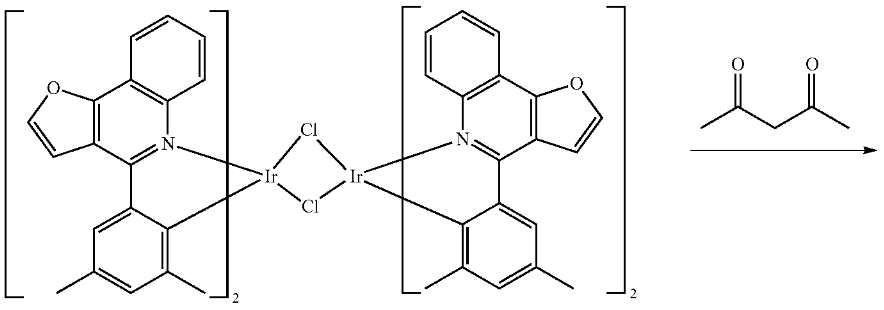
C3
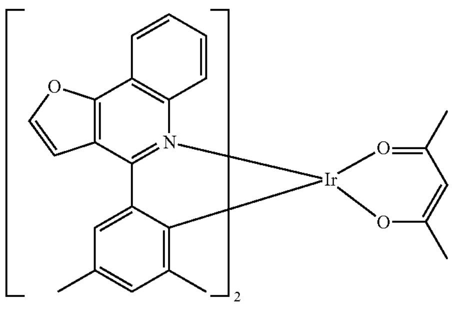
Compound 5

Preparation of Compound C3

The compound C3 (6.4 g, yield 83%) was obtained in the same manner as in the preparation method of the compound C1, except that B3 (6.0 g, 22 mmol) and $IrCl_3 \cdot H_2Ox$ (3.5 g, 10 mmol) were used instead of B1 (10 g, 34.55 mmol) and $IrCl_3 \cdot H_2Ox$ (6.1 g, 15.71 mmol)

Preparation of Compound 5

The compound 5 (3.5 g, yield 50%) was obtained in the same manner as in the preparation method of the compound 42, except that C1 (10.1 g, 6.28 mmol) and 3,7-diethyl-nonane-4,6-dione (12.7 g, 59.64 mmol) and $Na_2CO_3$ (13 g, 122.46 mmol) were replaced with C3 (6.4 g, 4.15 mmol) and pentane-2,4-dione (4.2 g, 41.50 mmol) and $Na_2CO_3$ (8.8 g, 83 mmol).

MS (m/z): 836.22

<Preparation of Compound 7>

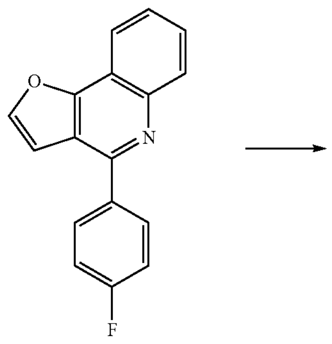

B4

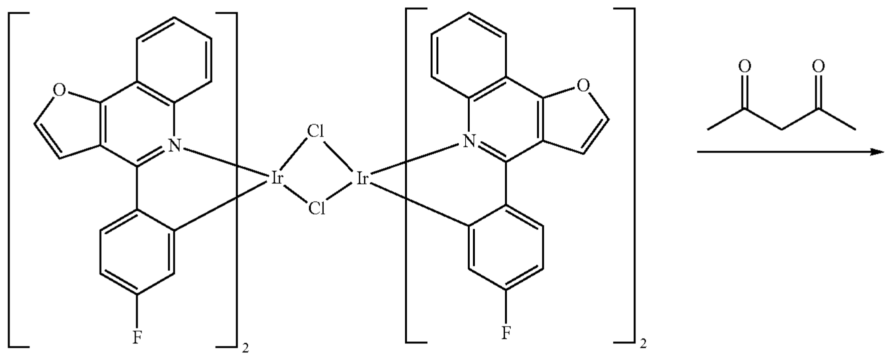

C4

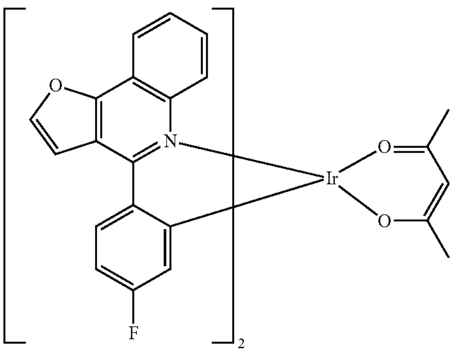

Compound 7

Preparation of Compound C4

The compound C4 (5.3 g, yield 70%) was obtained in the same manner as in the preparation method of the compound C1, except that B1 (10 g, 34.55 mmol) and $IrCl_3{\cdot}H_2Ox$ (6.1 g, 15.71 mmol) were replaced with B4 (5.8 g, 22 mmol) and $IrCl_3{\cdot}H_2Ox$ (3.5 g, 10 mmol).

Preparation of Compound 7

The compound 7 (2.3 g, yield 40%) was obtained in the same manner as in the preparation method of the compound 42, except that C1 (10.1 g, 6.28 mmol) and 3,7-diethyl-nonane-4,6-dione (12.7 g, 59.64 mmol) and $Na_2CO_3$ (13 g, 122.46 mmol) were replaced with C4 (5.3 g, 3.50 mmol) and pentane-2,4-dione (3.5 g, 35.00 mmol) and $Na_2CO_3$ (7.4 g, 70 mmol).

MS (m/z): 816.14

<Preparation of Compound 8>

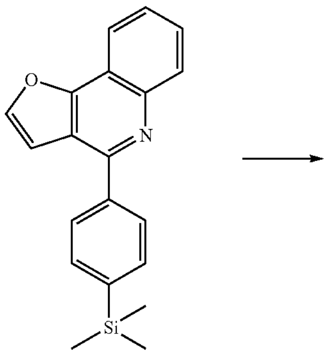

B5

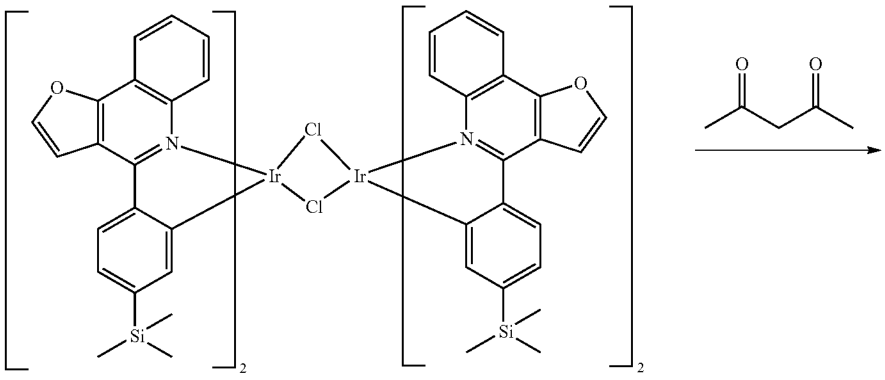

C5

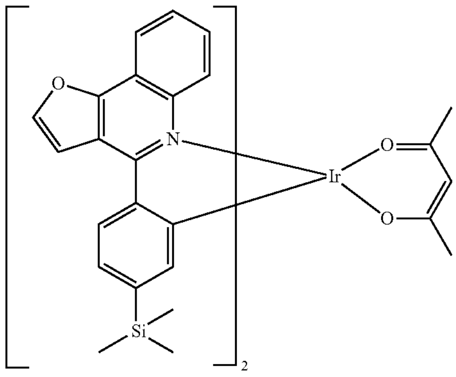

Compound 8

Preparation of Compound C5

The compound C5 (6.7 g, yield 78%) was obtained in the same manner as in the preparation method of the compound C1, except that B1 (10 g, 34.55 mmol) and $IrCl_3{\cdot}H_2Ox$ (6.1 g, 15.71 mmol) were replaced with B5 (7.0 g, 22 mmol) and $IrCl_3{\cdot}H_2Ox$ (3.5 g, 10 mmol).

Preparation of Compound 8

The compound 8 (3.0 g, yield 41%) was obtained in the same manner as in the preparation method of the compound 42, except that C1 (10.1 g, 6.28 mmol) and 3,7-diethylnonane-4,6-dione (12.7 g, 59.64 mmol) and $Na_2CO_3$ (13 g, 122.46 mmol) were replaced with C5 (6.7 g, 3.90 mmol) and pentane-2,4-dione (3.9 g, 39.00 mmol) and $Na_2CO_3$ (8.3 g, 78 mmol).

MS (m/z): 924.24

<Preparation of Compound 10>

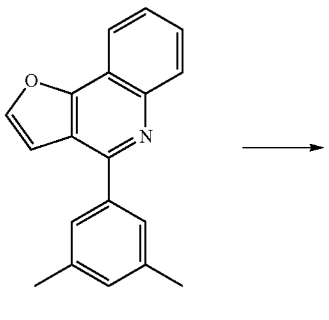

B6

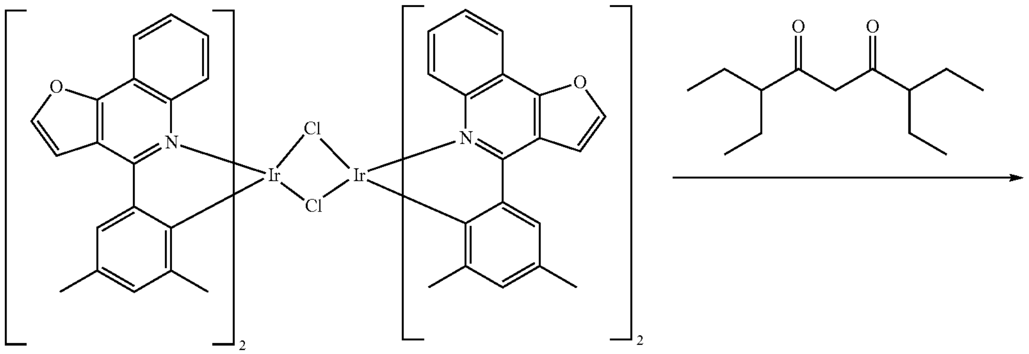

C6

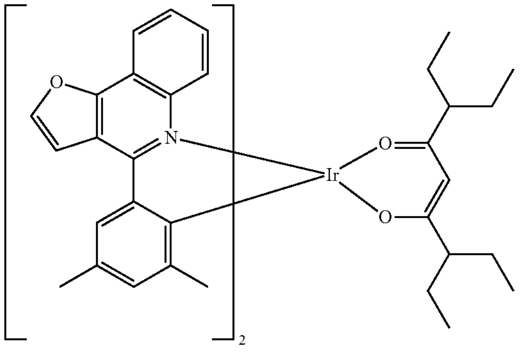

Compound 10

Preparation of Compound C6

The compound C6 (6.4 g, yield 83%) was obtained in the same manner as in the preparation method of the compound C1, except that B1 (10 g, 34.55 mmol) and $IrCl_3 \cdot H_2Ox$ (6.1 g, 15.71 mmol) were replaced with B6 (6.0 g, 22 mmol) and $IrCl_3 \cdot H_2Ox$ (3.5 g, 10 mmol).

Preparation of Compound 10

The compound 10 (3.4 g, yield 43%) was obtained in the same manner as in the preparation method of the compound 42, except that C1 (10.1 g, 6.28 mmol) and 3,7-diethylnonane-4,6-dione (12.7 g, 59.64 mmol) and $Na_2CO_3$ (13 g, 122.46 mmol) were replaced with C6 (6.4 g, 4.15 mmol) and 3,7-diethylnonane-4,6-dione (8.8 g, 41.50 mmol) and $Na_2CO_3$ (8.8 g, 83 mmol).

MS (m/z): 948.35

<Preparation of Compound 11>

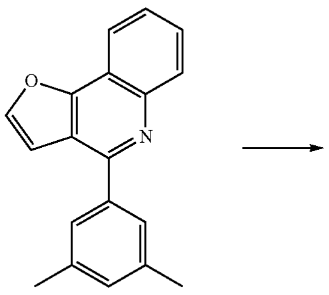

B7

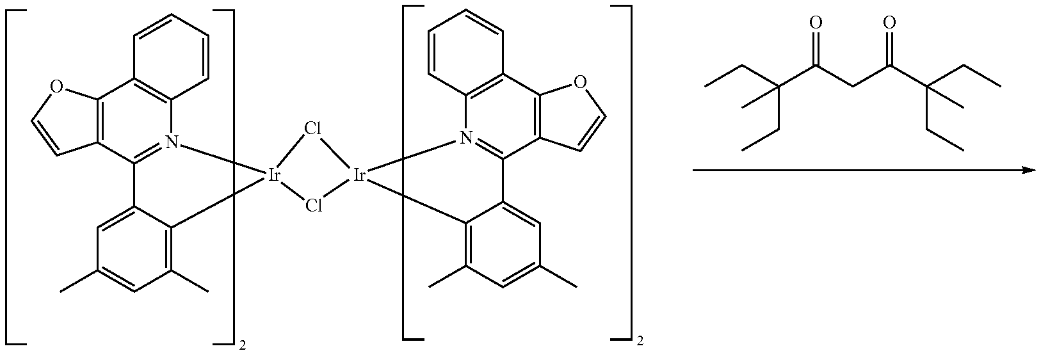

C7

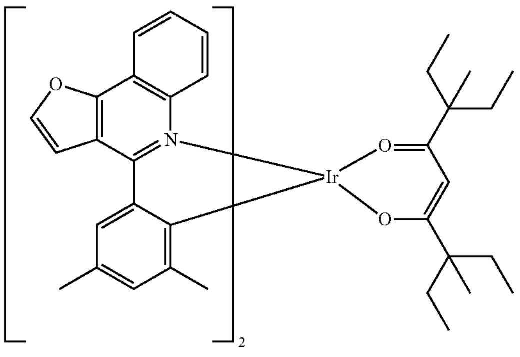

Compound 11

Preparation of Compound C7

The compound C7 (6.4 g, yield 83%) was obtained in the same manner as in the preparation method of the compound C1, except that B1 (10 g, 34.55 mmol) and $IrCl_3 \cdot H_2Ox$ (6.1 g, 15.71 mmol) were replaced with B7 (6.0 g, 22 mmol) and $IrCl_3 \cdot H_2Ox$ (3.5 g, 10 mmol).

Preparation of Compound 11

The compound 11 (3.4 g, yield 42%) was obtained in the same manner as in the preparation method of the compound 42 except that C1 (10.1 g, 6.28 mmol) and 3,7-diethyl-nonane-4,6-dione (12.7 g, 59.64 mmol) and $Na_2CO_3$ (13 g, 122.46 mmol) were replaced with C7 (6.4 g, 4.15 mmol) and 3,7-diethyl-3,7-dimethylnonane-4,6-dione (10.0 g, 41.50 mmol) and $Na_2CO_3$ (8.8 g, 83 mmol).

MS (m/z): 976.38

<Preparation of Compound 15>

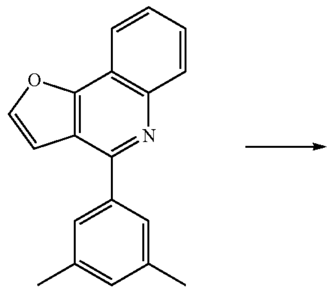

B8

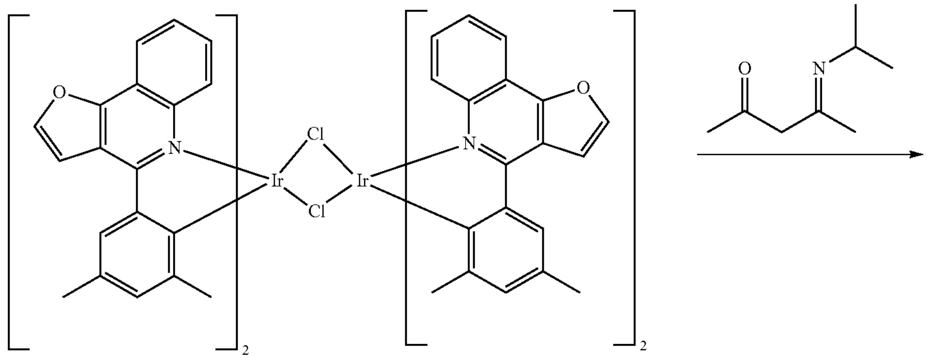

C8

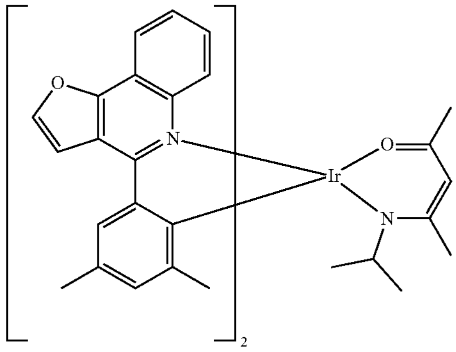

Compound 15

Preparation of Compound C8

The compound C8 (6.4 g, yield 83%) was obtained in the same manner as in the preparation method of the compound C1, except that B1 (10 g, 34.55 mmol) and $IrCl_3 \cdot H_2Ox$ (6.1 g, 15.71 mmol) were replaced with B8 (6.0 g, 22 mmol) and $IrCl_3 \cdot H_2Ox$ (3.5 g, 10 mmol).

Preparation of Compound 15

The compound 15 (2.9 g, yield 40%) was prepared in the same manner as in the preparation method of the compound 42 except that C1 (10.1 g, 6.28 mmol) and 3,7-diethyl-nonane-4,6-dione (12.7 g, 59.64 mmol) and $Na_2CO_3$ (13 g, 122.46 mmol) were replaced with C8 (6.4 g, 4.15 mmol) and (E)-4-(isopropylimino)pentan-2-one (5.9 g, 41.50 mmol) and $Na_2CO_3$ (8.8 g, 83 mmol).

MS (m/z): 877.29

<Preparation of Compound 16>

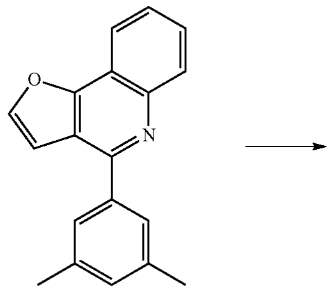

B9

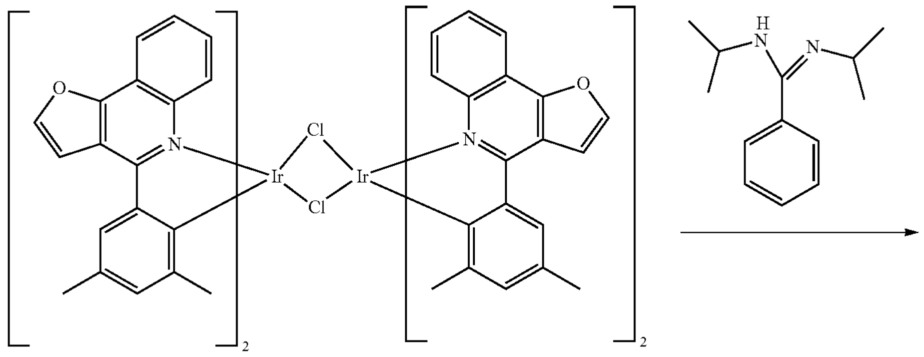

C9

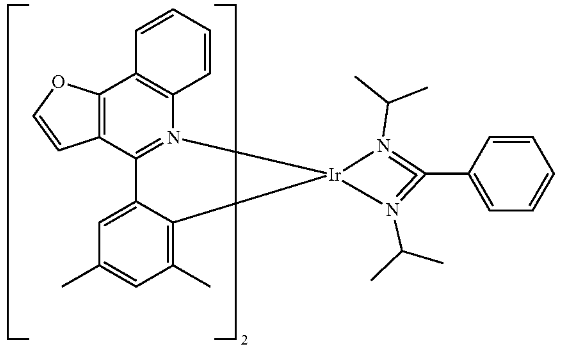

Compound 16

Preparation of Compound C9

The compound C9 (6.4 g, yield 83%) was obtained in the same manner as in the preparation method of the compound C1 except for using B9 (6.0 g, 22 mmol) and $IrCl_3{\cdot}H_2Ox$ (3.5 g, 10 mmol) instead of B1 (10 g, 34.55 mmol) and $IrCl_3{\cdot}H_2Ox$ (6.1 g, 15.71 mmol).

Preparation of Compound 16

The compound 16 (2.9 g, yield 37%) was obtained in the same manner as in the preparation method of the compound 42 except that C1 (10.1 g, 6.28 mmol) and 3,7-diethyl-nonane-4,6-dione (12.7 g, 59.64 mmol) and $Na_2CO_3$ (13 g, 122.46 mmol) were replaced with C9 (6.4 g, 4.15 mmol) and (E)-N,N'-diisopropylbenzimidamide (8.5 g, 41.50 mmol) and $Na_2CO_3$ (8.8 g, 3 mmol).

MS (m/z): 940.33

<Preparation of Compound 19>

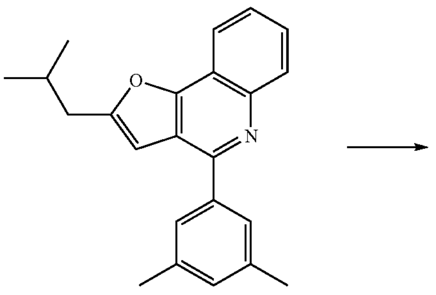

B10

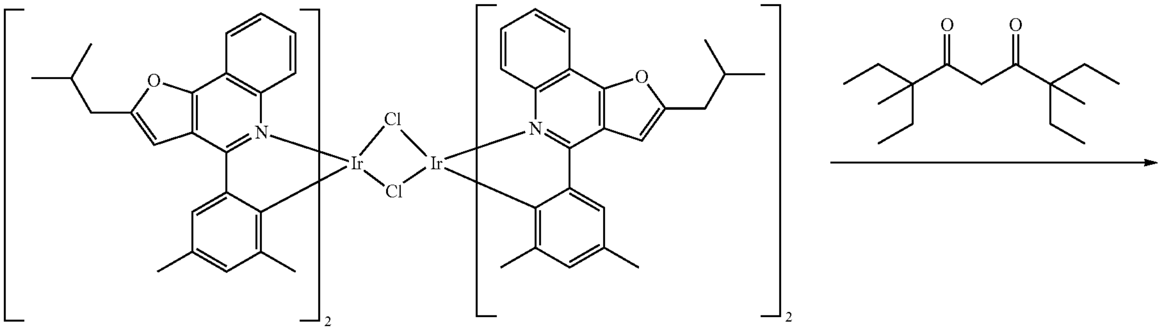

C10

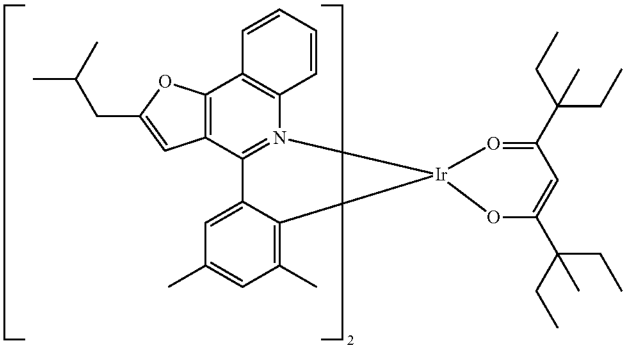

Compound 19

Preparation of Compound C10

The compound C10 (6.6 g, yield 75%) was obtained in the same manner as in the preparation method of the compound C1, except that B1 (10 g, 34.55 mmol) and $IrCl_3 \cdot H_2Ox$ (6.1 g, 15.71 mmol) were replaced with B10 (7.2 g, 22 mmol) and $IrCl_3 \cdot H_2Ox$ (3.5 g, 10 mmol).

Preparation of Compound 19

The compound 19 (3.3 g, yield 41%) was obtained in the same manner as in the preparation method of the compound 42, except that C1 (10.1 g, 6.28 mmol) and 3,7-diethylnonane-4,6-dione (12.7 g, 59.64 mmol) and $Na_2CO_3$ (13 g, 122.46 mmol) were replaced with C10 (1.6 g, 3.75 mmol) and 3,7-diethyl-3,7-dimethylnonane-4,6-dione (9.0 g, 37.50 mmol) and $Na_2CO_3$ (7.9 g, 75 mmol).

MS (m/z): 1088.50

<Preparation of Compound 21>

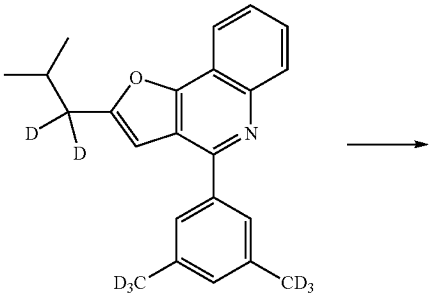

B11

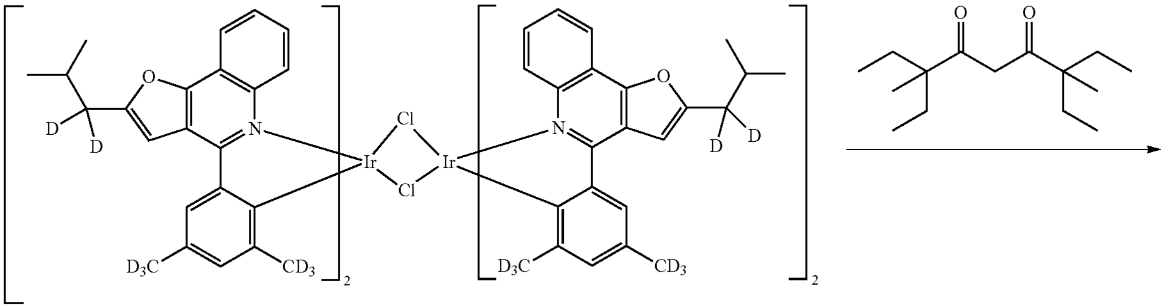

C11

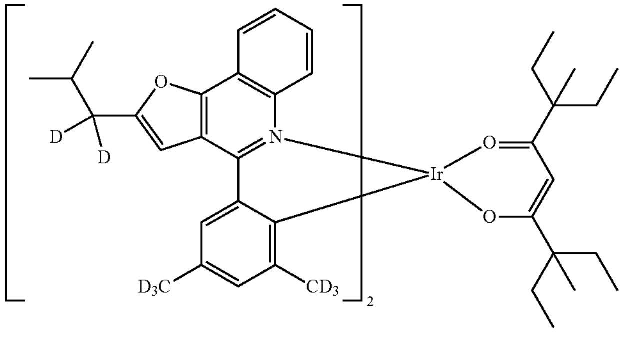

Compound 21

Preparation of Compound C11

The compound C11 (6.7 g, yield 74%) was obtained in the same manner as in the preparation method of the compound C1, except that B1 (10 g, 34.55 mmol) and $IrCl_3 \cdot H_2Ox$ (6.1 g, 15.71 mmol) were replaced with B11 (7.4 g, 22 mmol) and $IrCl_3 \cdot H_2Ox$ (3.5 g, 10 mmol).

Preparation of Compound 21

The compound 21 (3.4 g, yield 41%) was obtained in the same manner as in the preparation method of the compound 42 except that C1 (10.1 g, 6.28 mmol) and 3,7-diethyl-nonane-4,6-dione (12.7 g, 59.64 mmol) and $Na_2CO_3$ (13 g, 122.46 mmol) were replaced with C11 (0.7 g, 3.70 mmol) and 3,7-diethyl-3,7-dimethylnonane-4,6-dione (8.9 g, 37.00 mmol) and $Na_2CO_3$ (7.8 g, 74 mmol).

<Preparation of Compound 28>

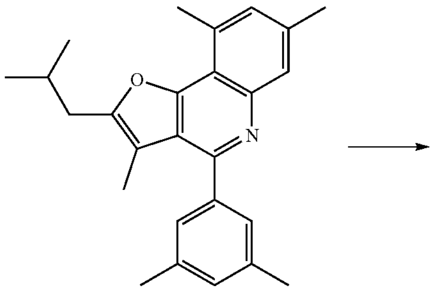

B12

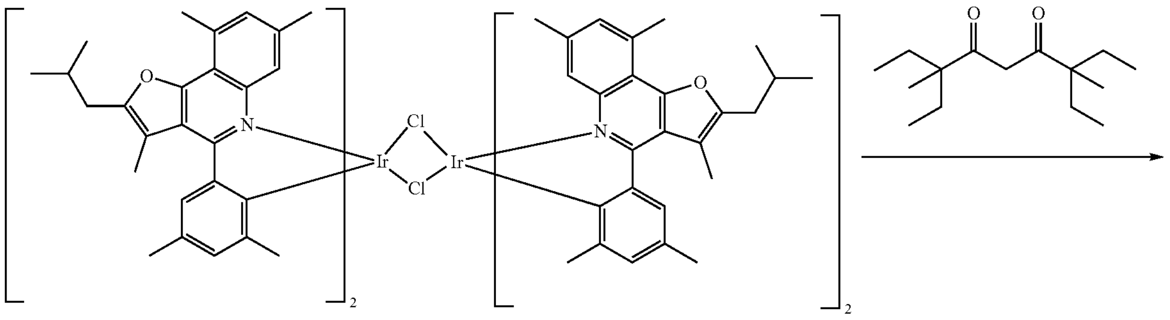

C12

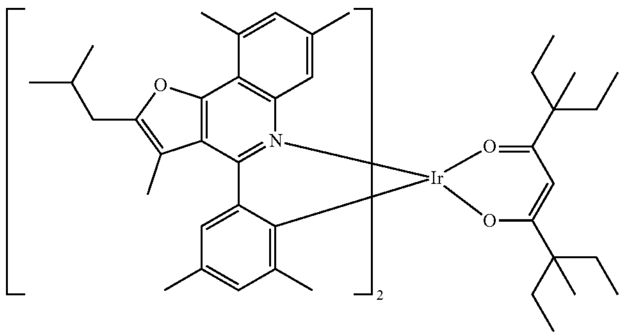

Compound 28

Preparation of Compound C12

The compound C12 (6.8 g, yield 70%) was obtained in the same manner as in the preparation method of the compound C1, except that B1 (10 g, 34.55 mmol) and $IrCl_3 \cdot H_2Ox$ (6.1 g, 15.71 mmol) were replaced with B12 (8.2 g, 22 mmol) and $IrCl_3 \cdot H_2Ox$ (3.5 g, 10 mmol).

Preparation of Compound 28

The compound 28 (3.3 g, yield 40%) was obtained in the same manner as in the preparation method of the compound 42 except that C1 (10.1 g, 6.28 mmol) and 3,7-diethyl-nonane-4,6-dione (12.7 g, 59.64 mmol) and $Na_2CO_3$ (13 g, 122.46 mmol) were replaced with C12 (6.8 g, 3.50 mmol) and 3,7-diethyl-3,7-dimethylnonane-4,6-dione (8.4 g, 35.00 mmol) and $Na_2CO_3$ (0.4 g, 70 mmol).

MS (n/z): 1172.60

<Preparation of Compound 32>

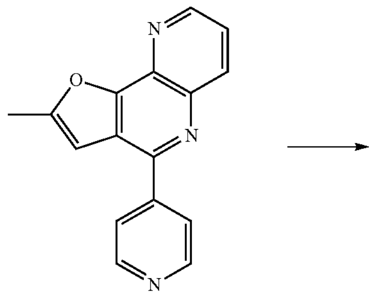

B13

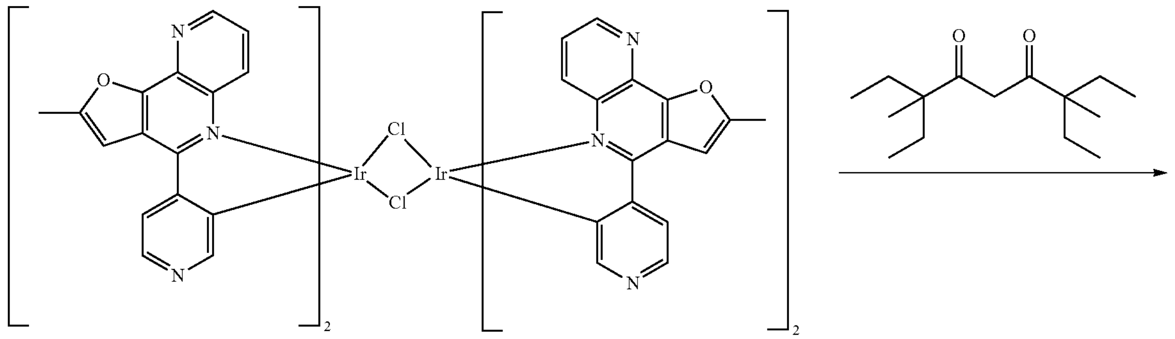

C13

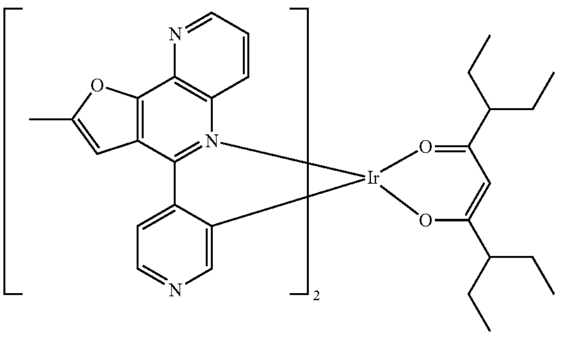

Compound 32

Preparation of Compound C13

The compound C13 (5.1 g, yield 68%) was obtained in the same manner as in the preparation method of the compound C1, except that B1 (10 g, 34.55 mmol) and $IrCl_3 \cdot H_2Ox$ (6.1 g, 15.71 mmol) were replaced with B13 (5.7 g, 22 mmol) and $IrCl_3 \cdot H_2Ox$ (3.5 g, 10 mmol).

Preparation of Compound 32

The compound 32 (2.5 g, yield 40%) was obtained in the same manner as in the preparation method of the compound 42, except that C1 (10.1 g, 6.28 mmol) and 3,7-diethylnonane-4,6-dione (12.7 g, 59.64 mmol) and $Na_2CO_3$ (13 g, 122.46 mmol) were replaced with C13 (5.1 g, 3.40 mmol) and 3,7-diethylnonane-4,6-dione (7.2 g, 34.00 mmol) and $Na_2CO_3$ (7.2 g, 68 mmol).

MS (m/z): 924.30

<Preparation of Compound 83>

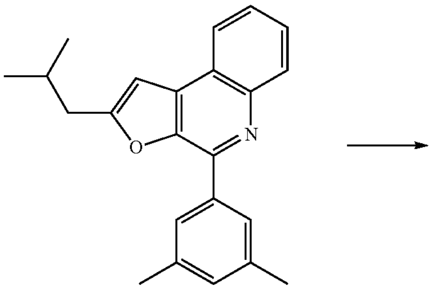

B14

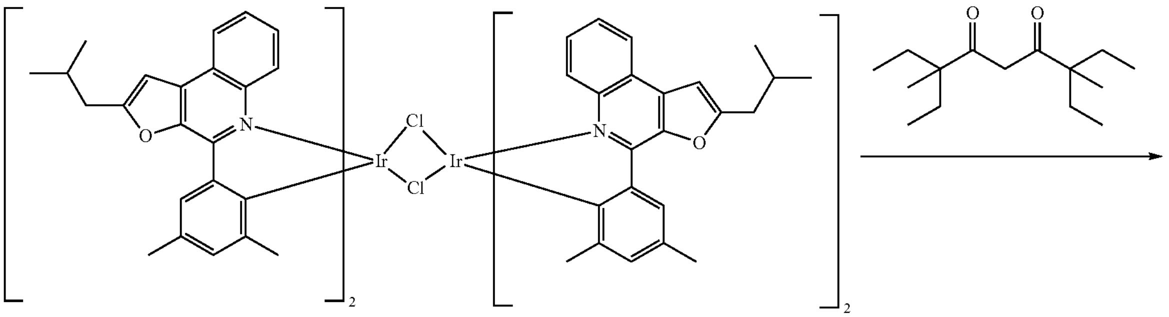

C14

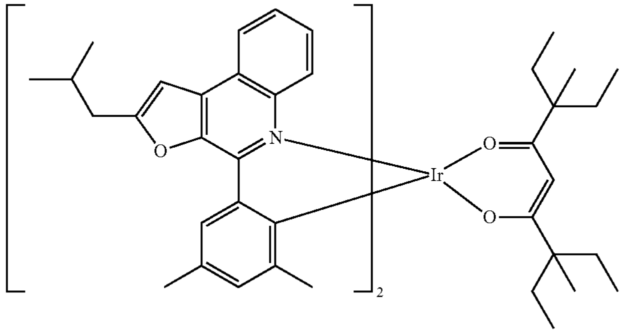

Compound 83

Preparation of Compound C14

The compound C14 (6.6 g, yield 75%) was obtained in the same manner as in the preparation method of the compound C1, except that B1 (10 g, 34.55 mmol) and $IrCl_3 \cdot H_2Ox$ (6.1 g, 15.71 mmol) were replaced with B14 (7.2 g, 22 mmol) and $IrCl_3 \cdot H_2Ox$ (3.5 g, 10 mmol)

Preparation of Compound 83

The compound 83 (3.3 g, yield 41%) was obtained in the same manner as in the preparation method of the compound 42 except that C1 (10.1 g, 6.28 mmol) and 3,7-diethylnonane-4,6-dione (12.7 g, 59.64 mmol) and $Na_2CO_3$ (13 g, 122.46 mmol) were replaced with C14 (0.6 g, 3.75 mmol) and 3,7-diethyl-3,7-dimethylnonane-4,6-dione (9.0 g, 37.50 mmol) and $Na_2CO_3$ (0.9 g, 75 mmol).

MS (m/z): 1088.50

<Preparation of Compound 115>

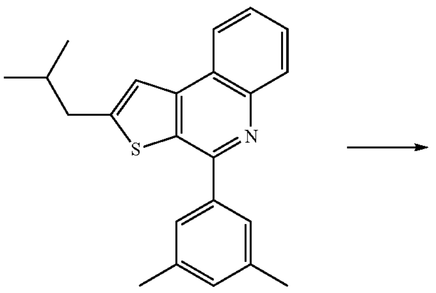

B15

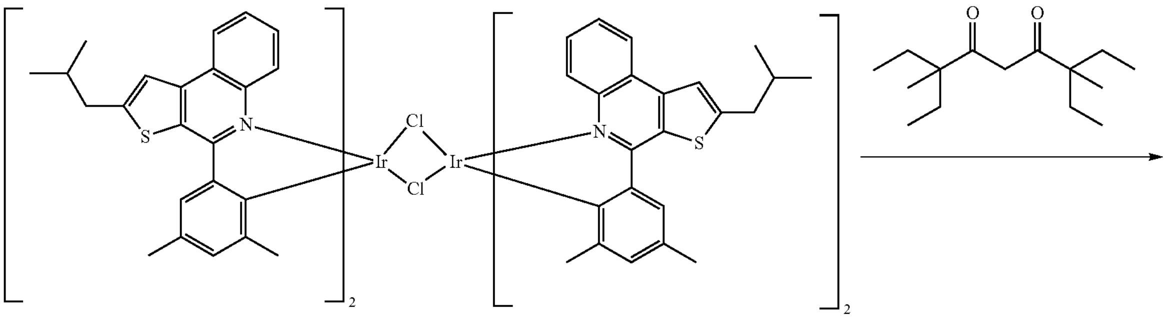

C15

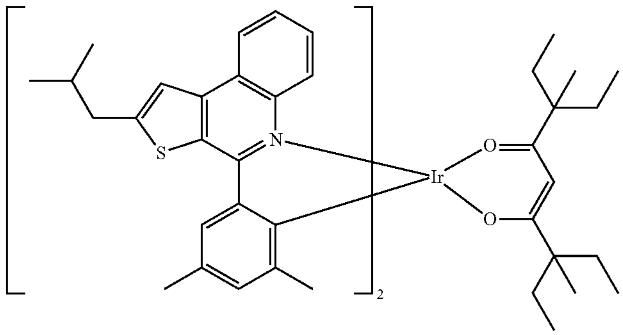

Compound 115

Preparation of Compound C15

The compound C15 (6.6 g, yield 72%) was obtained in the same manner as in the preparation method of the compound C1, except that B1 (10 g, 34.55 mmol) and $IrCl_3 \cdot H_2Ox$ (6.1 g, 15.71 mmol) were replaced with B15 (7.6 g, 22 mmol) and $IrCl_3 \cdot H_2Ox$ (3.5 g, 10 mmol).

Preparation of Compound 115

The compound 115 (3.1 g, yield 39%) was obtained in the same manner as in the preparation method of the compound 42 except that C1 (10.1 g, 6.28 mmol) and 3,7-diethylnonane-4,6-dione (12.7 g, 59.64 mmol) and $Na_2CO_3$ (13 g, 122.46 mmol) were replaced with C15 (6.6 g, 3.60 mmol) and 3,7-diethyl-3,7-dimethylnonane-4,6-dione (8.7 g, 36.00 mmol) and $N_2CO_3$ (7.9 g, 75 mmol).

MS (m/z): 1088.50

<Preparation of Compound 145>

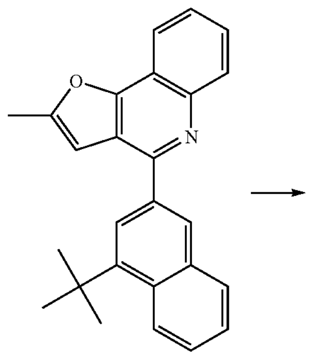

B2

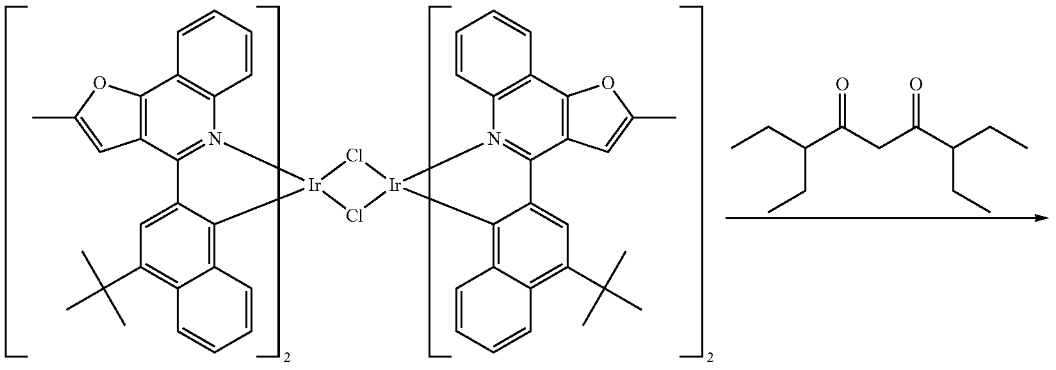

C2

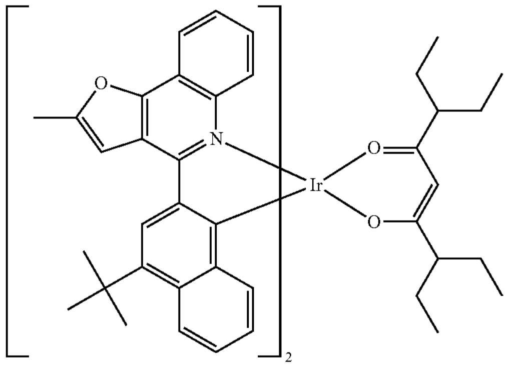

Compound 145

Preparation of Compound C2

B2 (9 g, 24.63 mmol), 2-ethoxyethanol 200 ml, and distilled water 66 ml were added to the reaction vessel, followed by nitrogen bubbling for 1 hour. Then, $IrCl_3 \cdot H_2Ox$ (4.3 g, 11.19 mmol) was added thereto and the mixture was refluxed for 24 hours. After the reaction was completed, the temperature was slowly lowered to room temperature and the resulting solid was filtered. The filtered solid was washed with methanol and dried to obtain the compound C2 (4.9 g, yield 46%).

Preparation of Compound 145

C2 (4.9 g, 2.56 mmol), 3,7-diethylnonane-4,6-dione (5.3 g, 24.98 mmol), $Na_2CO_3$ (5.3 g, 49.92 mmol), 200 ml of 2-ethoxyethanol were added to the reaction vessel and were stirred slowly for 24 hours. After the reaction was completed, dichloromethane was added to the reaction product to dissolve the reaction product, and then extraction was performed with dichloromethane and distilled water. Water in an organic layer was removed using $MgSO_4$, and then the solvent was removed via filtration under reduced pressure. Column chromatography was performed with hexane and dichloromethane to obtain the compound 145 (2.7 g, yield 60%).

MS (m/z): 1132.46

<Preparation of Compound 131>

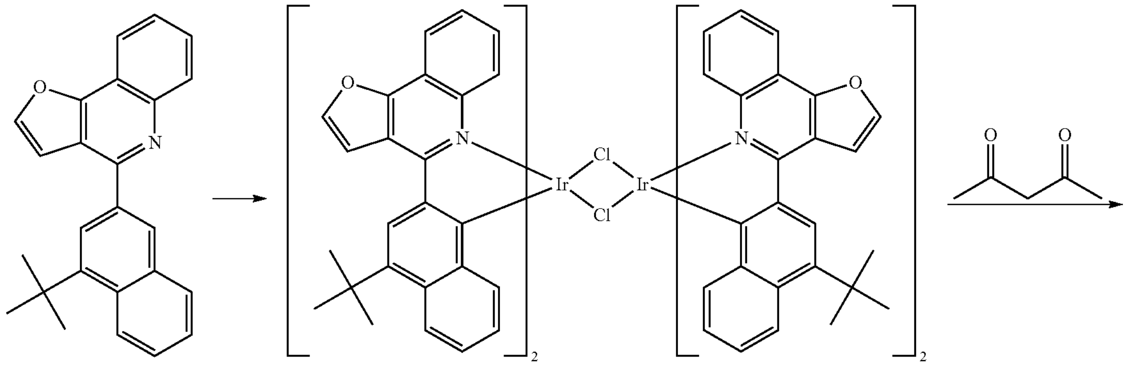

B16 C16

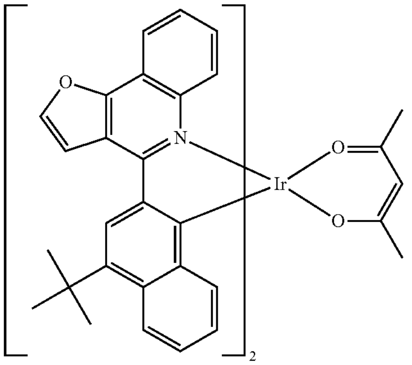

Compound 131

Preparation of Compound C16

The compound C16 (4.1 g, yield 44%) was obtained in the same manner as in the preparation method of the compound C2, except that B2 (9 g, 24.63 mmol) and $IrCl_3{\cdot}H_2Ox$ (4.3 g, 11.19 mmol) were replaced with B16 (7.7 g, 22 mmol) and $IrCl_3{\cdot}H_2Ox$ (3.5 g, 10 mmol).

Preparation of Compound 131

The compound 131 (2.8 g, yield 65%) was obtained in the same manner as in the preparation method of the compound 42, except that C2 (4.9 g, 2.56 mmol) and 3,7-diethyl-nonane-4,6-dione (5.3 g, 24.98 mmol) and $Na_2CO_3$ (5.3 g, 49.92 mmol) were replaced with C16 (4.1 g, 2.20 mmol) and pentane-2,4-dione (2.2 g, 22.00 mmol) and $Na_2CO_3$ (4.7 g, 44 mmol).

MS (m/z): 992.32

<Preparation of Compound 135>

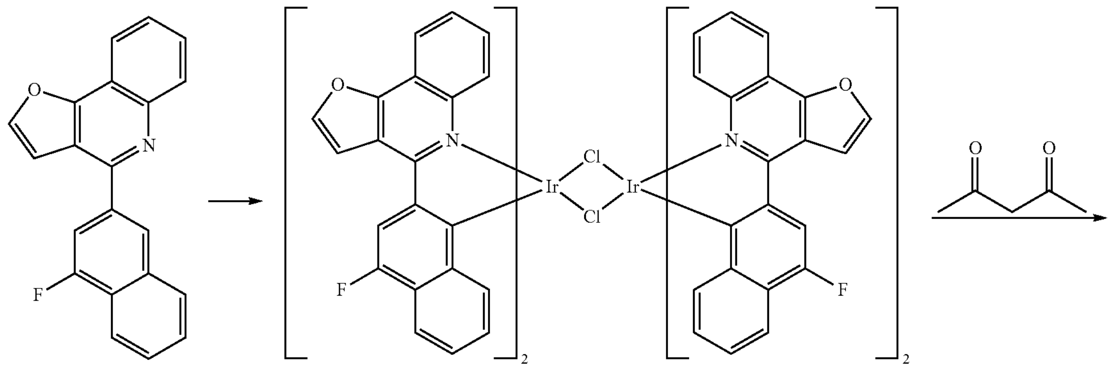

B17 C17

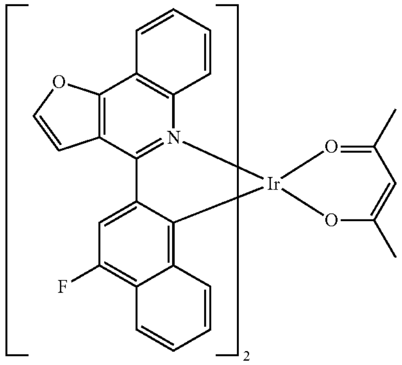

Compound 135

Preparation of Compound C17

The compound C17 (3.4 g, yield 40%) was obtained in the same manner as in the preparation method of the compound C2, except that B2 (9 g, 24.63 mmol) and $IrCl_3 \cdot H_2Ox$ (4.3 g, 11.19 mmol) were replaced with B17 (6.9 g, 22 mmol) and $IrCl_3 \cdot H_2Ox$ (3.5 g, 10 mmol)

Preparation of Compound 135

The compound 135 (2.0 g, yield 55%) was obtained in the same manner as in the preparation method of the compound 42, except that C2 (4.9 g, 2.56 mmol) and 3,7-diethyl-nonane-4,6-dione (5.3 g, 24.98 mmol) and $Na_2CO_3$ (5.3 g, 49.92 mmol) were replaced with C17 (3.4 g, 2.00 mmol) and pentane-2,4-dione (2.0 g, 20.00 mmol) and $Na_2CO_3$ (4.2 g, 40 mmol).

MS (m/z): 916.17

<Preparation of Compound 136>

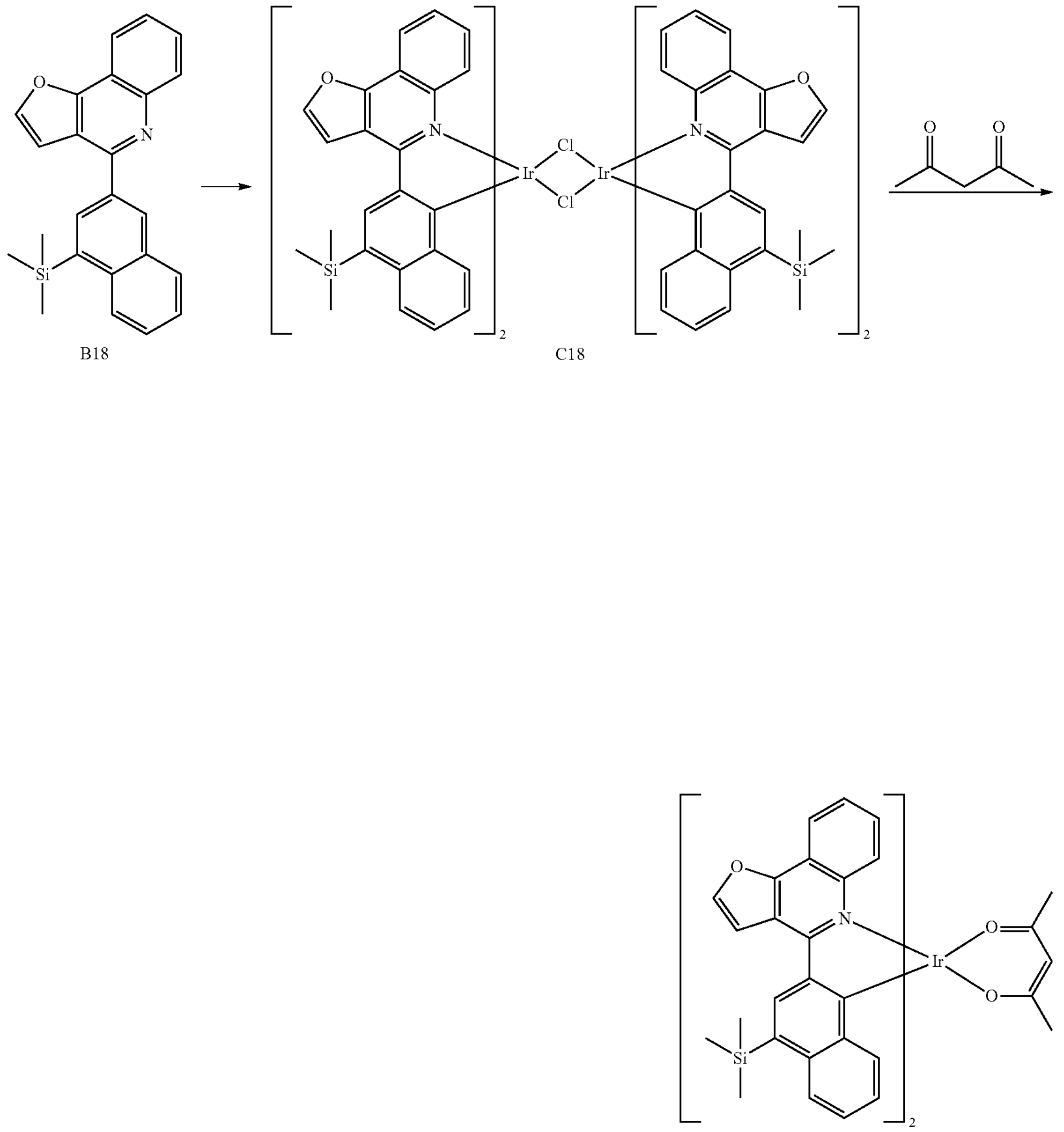

B18

C18

Compound 136

Preparation of Compound C18

The compound C18 (4.1 g, yield 43%) was obtained in the same manner as in the preparation method of the compound C2 except that B2 (9 g, 24.63 mmol) and $IrCl_3 \cdot H_2Ox$ (4.3 g, 11.19 mmol) were replaced with B18 (8.1 g, 22 mmol) and $IrCl_3 \cdot H_2Ox$ (3.5 g, 10 mmol)

Preparation of Compound 136

The compound 136 (2.7 g, yield 62%) was obtained in the same manner as in the preparation method of the compound 42, except that C2 (4.9 g, 2.56 mmol) and 3,7-diethyl-nonane-4,6-dione (5.3 g, 24.98 mmol) and $Na_2CO_3$ (5.3 g, 49.92 mmol) were replaced with C18 (4.1 g, 2.15 mmol) and pentane-2,4-dione (2.2 g, 21.50 mmol) and $Na_2CO_3$ (4.6 g, 43 mmol).

MS (m/z): 1024.27

<Preparation of Compound 138>

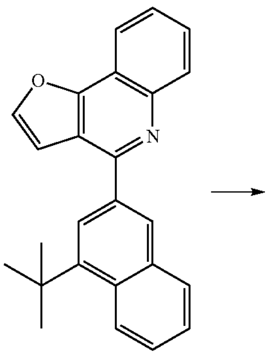

B19

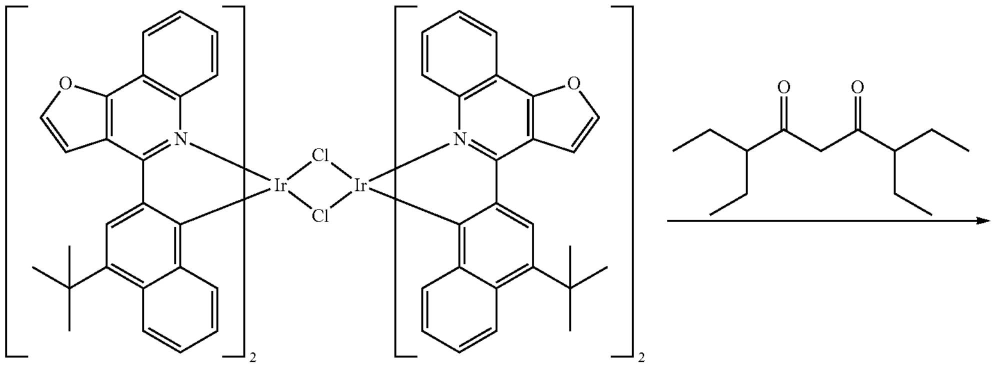

C19

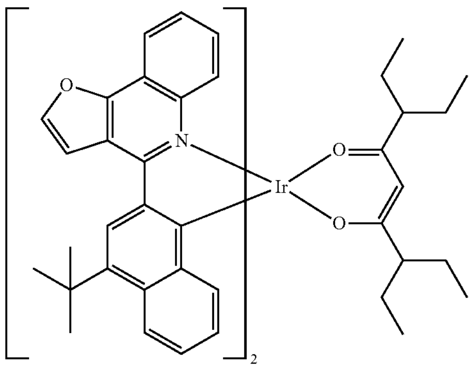

Compound 138

Preparation of Compound C19

The compound C19 (4.1 g, yield 44%) was obtained in the same manner as in the preparation method of the compound C2, except that B2 (9 g, 24.63 mmol) and $IrCl_3 \cdot H_2Ox$ (4.3 g, 11.19 mmol) were replaced with B19 (7.7 g, 22 mmol) and $IrCl_3 \cdot H_2Ox$ (3.5 g, 10 mmol)

Preparation of Compound 138

The compound 138 (3.0 g, yield 61%) was obtained in the same manner as in the preparation method of the compound 42, except that C2 (4.9 g, 2.56 mmol) and 3,7-diethylnonane-4,6-dione (5.3 g, 24.98 mmol) and $Na_2CO_3$ (5.3 g, 49.92 mmol) were replaced with C19 (4.1 g, 2.20 mmol) and 3,7-diethylnonane-4,6-dione (4.7 g, 22.00 mmol) and $Na_2CO_3$ (4.7 g, 44 mmol).

MS (m/z): 1104.44

<Preparation of Compound 139>

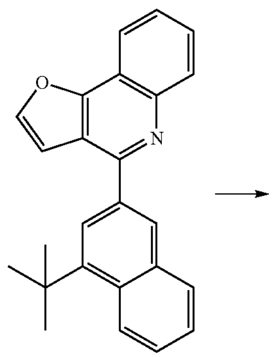

B20

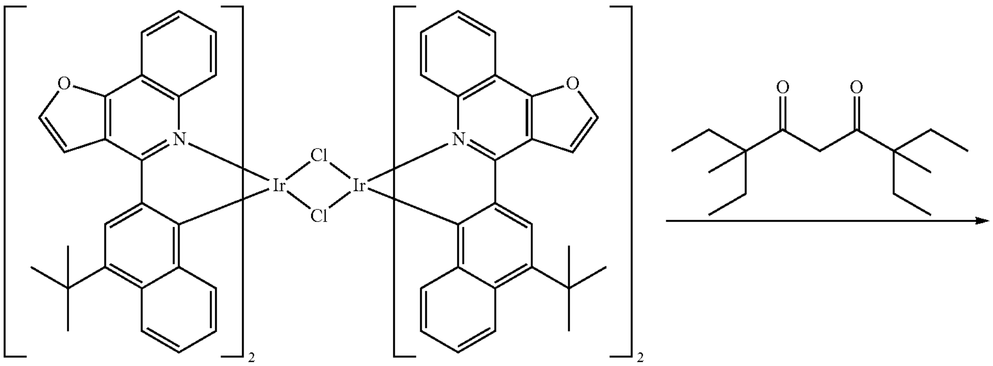

C29

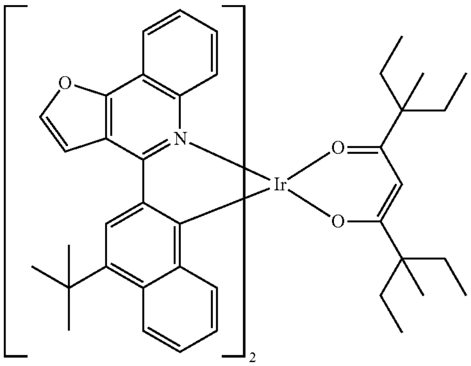

Compound 139

Preparation of Compound C20

The compound C20 (4.1 g, yield 44%) was obtained in the same manner as in the preparation method of the compound C2 except that B2 (9 g, 24.63 mmol) and $IrCl_3 \cdot H_2Ox$ (4.3 g, 11.19 mmol) were replaced with B20 (7.7 g, 22 mmol) and $IrCl_3 \cdot H_2Ox$ (3.5 g, 10 mmol)

Preparation of Compound 139

The compound 139 (3.0 g, yield 60%) was obtained in the same manner as in the preparation method of the compound 42, except that C2 (4.9 g, 2.56 mmol) and 3,7-diethyl-nonane-4,6-dione (5.3 g, 24.98 mmol) and $Na_2CO_3$ (5.3 g, 49.92 mmol) were replaced with C20 (4.1 g, 2.20 mmol) and 3,7-diethyl-3,7-dimethylnonane-4,6-dione (5.3 g, 22.00 mmol) and $Na_2CO_3$ (4.7 g, 44 mmol).

MS (m/z): 1132.47

<Preparation of Compound 143>

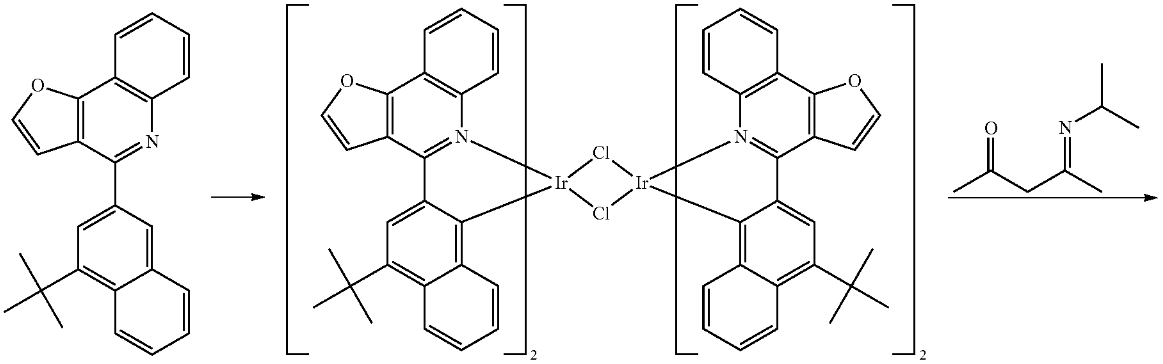

B21 C21

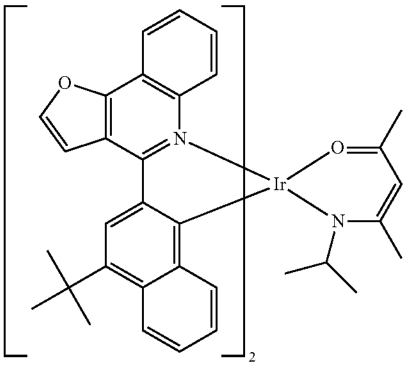

Compound 143

Preparation of Compound C21

The compound C21 (4.1 g, yield 44%) was obtained in the same manner as in the preparation method of the compound C2 except that B2 (9 g, 24.63 mmol) and $IrCl_3 \cdot H_2Ox$ (4.3 g, 11.19 mmol) were replaced with B21 (7.7 g, 22 mmol) and $IrCl_3 \cdot H_2Ox$ (3.5 g, 10 mmol).

Preparation of Compound 143

The compound 143 (2.4 g, yield 52%) was obtained in the same manner as in the preparation method of the compound 42 except that C2 (4.9 g, 2.56 mmol) and 3,7-diethylnonane-4,6-dione (5.3 g, 24.98 mmol) and $Na_2CO_3$ (5.3 g, 49.92 mmol) were replaced with C21 (4.1 g, 2.20 mmol) and (E)-4-(isopropylimino)pentan-2-one (3.1 g, 22.00 mmol) and $Na_2CO_3$ (4.7 g, 44 mmol).

MS (m/z): 1033.38

<Preparation of Compound 144>

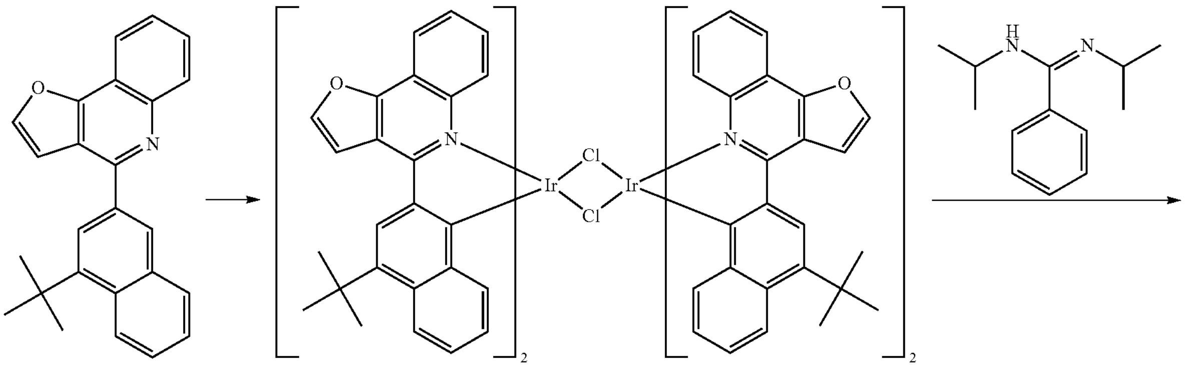

B22

C22

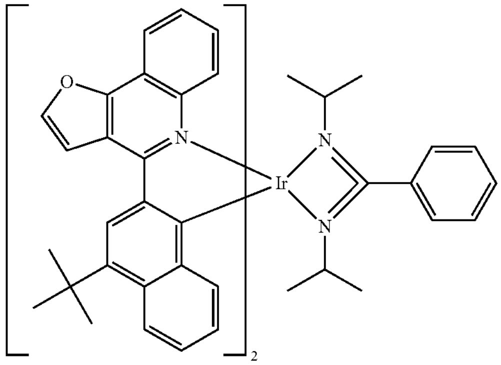

Compound 144

Preparation of Compound C22

The compound C22 (4.1 g, yield 44%) was obtained in the same manner as in the preparation method of the compound C2 except that B2 (9 g, 24.63 mmol) and $IrCl_3 \cdot H_2Ox$ (4.3 g, 11.19 mmol) were replaced with B22 (7.7 g, 22 mmol) and $IrCl_3 \cdot H_2Ox$ (3.5 g, 10 mmol).

Preparation of Compound 144

The compound 144 (1.9 g, yield 40%) was obtained in the same manner as in the preparation method of the compound 42 except that C2 (4.9 g, 2.56 mmol) and 3,7-diethylnonane-4,6-dione (5.3 g, 24.98 mmol) and $Na_2CO_3$ (5.3 g, 49.92 mmol) were replaced with C22 (4.1 g, 2.20 mmol) and (E)-N,N'-diisopropylbenzimidamide (4.5 g, 22.00 mmol) and $Na_2CO_3$ (4.7 g, 44 mmol).

MS (m/z): 1096.39

<Preparation of Compound 147>

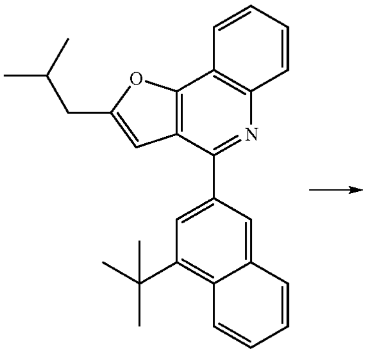

B23

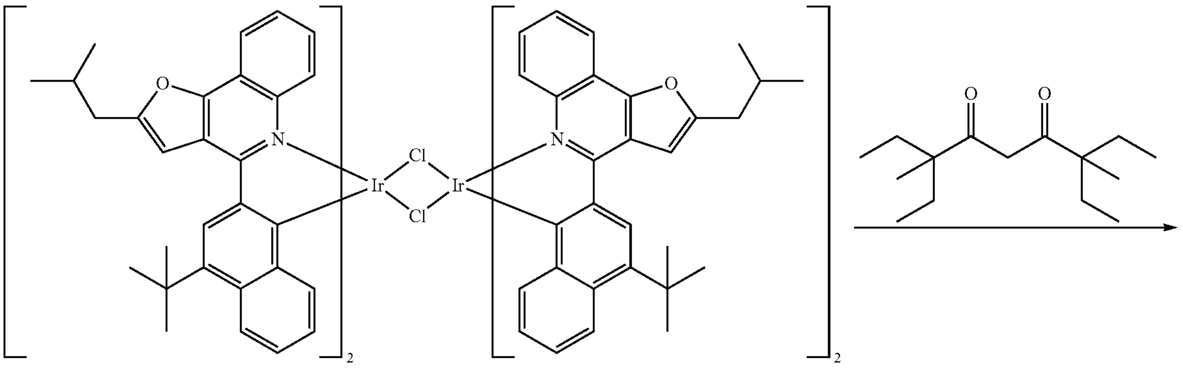

C23

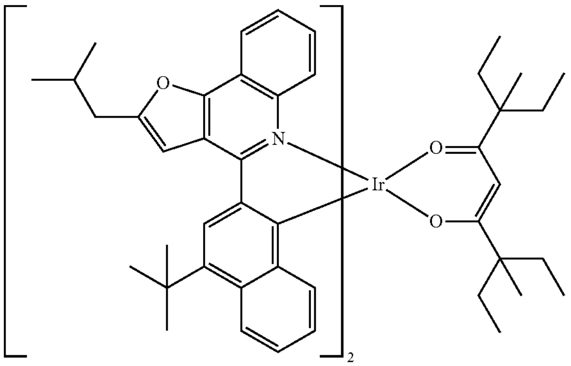

Compound 147

Preparation of Compound C23

The compound C23 (5.2 g, yield 50%) was obtained in the same manner as in the preparation method of the compound C2 except that B2 (9 g, 24.63 mmol) and $IrCl_3 \cdot H_2Ox$ (4.3 g, 11.19 mmol) were replaced with B23 (9.0 g, 22 mmol) and $IrCl_3 \cdot H_2Ox$ (3.5 g, 10 mmol).

Preparation of Compound 147

The compound 147 (3.6 g, yield) 58%) was obtained in the same manner as in the preparation method of the compound 42, except that C2 (4.9 g, 2.56 mmol) and 3,7-diethylnonane-4,6-dione (5.3 g, 24.98 mmol) and $Na_2CO_3$ (5.3 g, 49.92 mmol) were replaced with C23 (5.2 g, 2.50 mmol) and 3,7-diethyl-3,7-dimethylnonane-4,6-dione (6.0 g, 25.00 mmol) and $Na_2CO_3$ (5.3 g, 50 mmol).

MS (m/z): 1244.60

<Preparation of Compound 149>

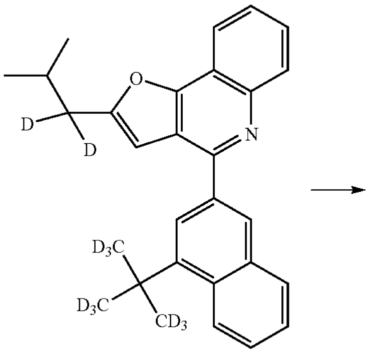

B24

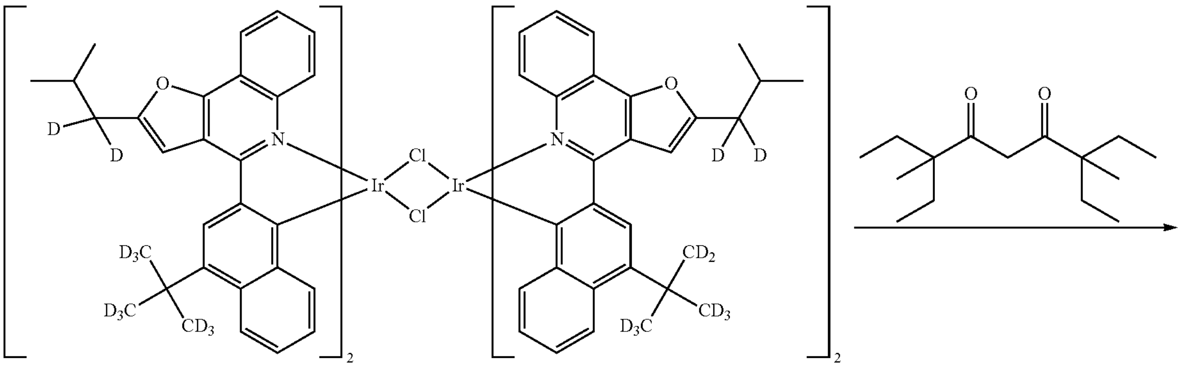

C24

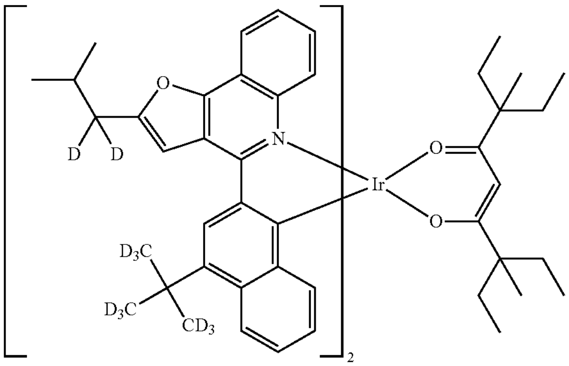

Compound 149

Preparation of Compound C24

The compound C24 (5.2 g, yield 49%) was obtained in the same manner as in the preparation method of the compound C2, except that B2 (9 g, 24.63 mmol) and $IrCl_3 \cdot H_2Ox$ (4.3 g, 11.19 mmol) were replaced with B24 (9.2 g, 22 mmol) and $IrCl_3 \cdot H_2Ox$ (3.5 g, 10 mmol).

Preparation of Compound 149

The compound 149 (3.5 g, yield 57%) was obtained in the same manner as in the preparation method of the compound 42, except that C2 (4.9 g, 2.56 mmol) and 3,7-diethylnonane-4,6-dione (5.3 g, 24.98 mmol) and $Na_2CO_3$ (5.3 g, 49.92 mmol) were replaced with C24 (5.2 g, 2.45 mmol) and 3,7-diethyl-3,7-dimethylnonane-4,6-dione (5.9 g, 24.50 mmol) and $Na_2CO_3$ (5.2 g, 49 mmol).

MS (m/z): 1266.74

<Preparation of Compound 156>

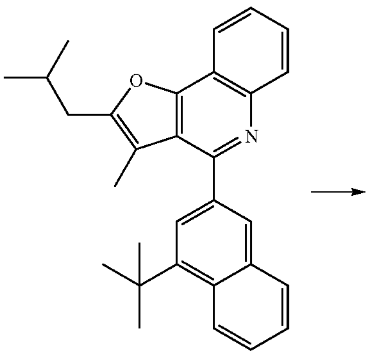

B25

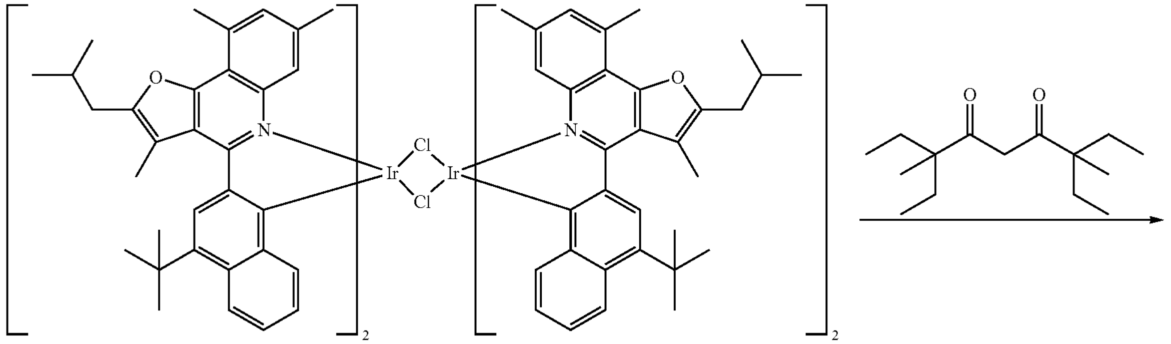

C25

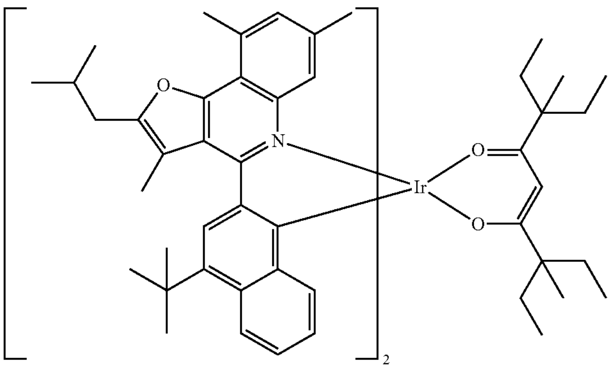

Compound 156

Preparation of Compound C25

The compound C25 (5.8 g, yield 52%) was obtained in the same manner as in the preparation method of the compound C2 except that B2 (9 g, 24.63 mmol) and $IrCl_3 \cdot H_2Ox$ (4.3 g, 11.19 mmol) were replaced with B25 (9.9 g, 22 mmol) and $IrCl_3 \cdot H_2Ox$ (3.5 g, 10 mmol).

Preparation of Compound 156

The compound 156 (4.1 g, yield) was obtained in the same manner as in the preparation method of the compound 42 except that C2 (4.9 g, 2.56 mmol) and 3,7-diethylnonane-4,6-dione (5.3 g, 24.98 mmol) and $Na_2CO_3$ (5.3 g, 49.92 mmol) were replaced with C25 (0.8 g, 2.60 mmol) and 3,7-diethyl-3,7-dimethylnonane-4,6-dione (6.2 g, 26.00 mmol) and $Na_2CO_3$ (5.5 g, 52 mmol).

MS (m/z): 1328.69

<Preparation of Compound 160>

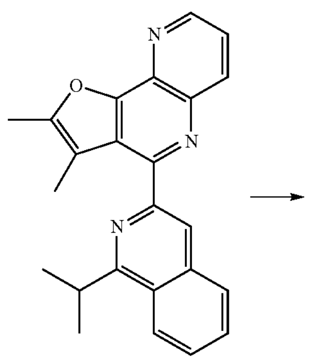

B26

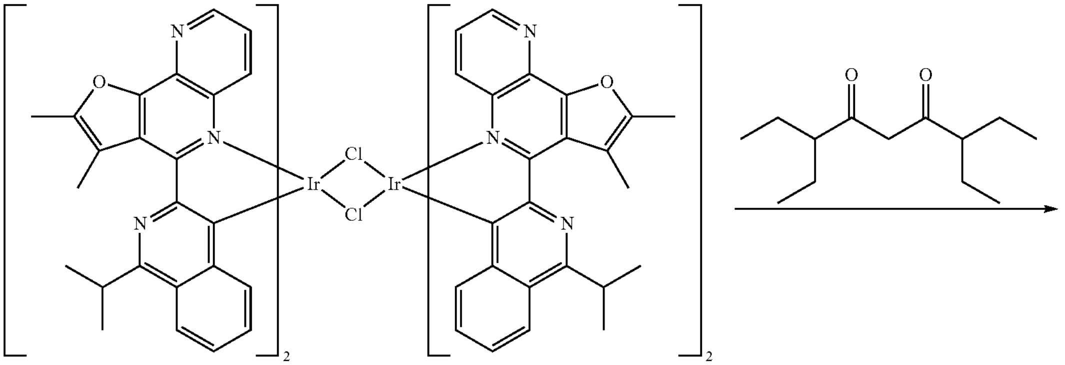

C26

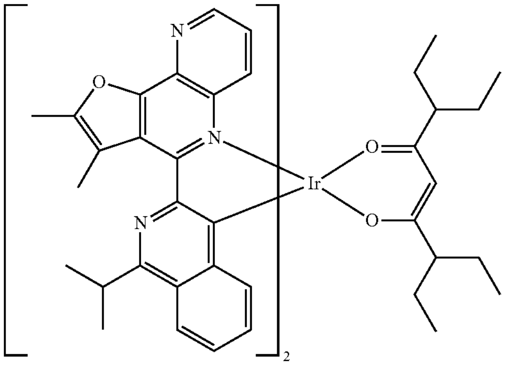

Compound 160

Preparation of Compound C26

The compound C26 (3.7 g, yield 38%) was obtained in the same manner as in the preparation method of the compound C2, except that B2 (9 g, 24.63 mmol) and $IrCl_3 \cdot H_2Ox$ (4.3 g, 11.19 mmol) were replaced with B26 (8.1 g, 22 mmol) and $IrCl_3 \cdot H_2Ox$ (3.5 g, 10 mmol).

Preparation of Compound 160

The compound 160 (2.2 g, yield 50%) was obtained in the same manner as in the preparation method of the compound 42, except that C2 (4.9 g, 2.56 mmol) and 3,7-diethylnonane-4,6-dione (5.3 g, 24.98 mmol) and $Na_2CO_3$ (5.3 g, 49.92 mmol) were replaced with C26 (3.7 g, 1.90 mmol) and 3,7-diethylnonane-4,6-dione (4.0 g, 19.00 mmol) and $Na_2CO_3$ (4.0 g, 38 mmol).

MS (m/z): 1136.45

<Preparation of Compound 177>

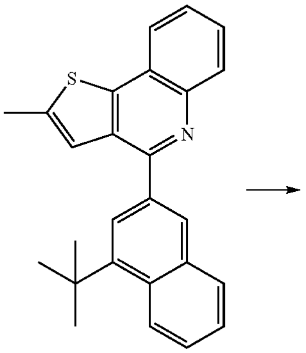

B27

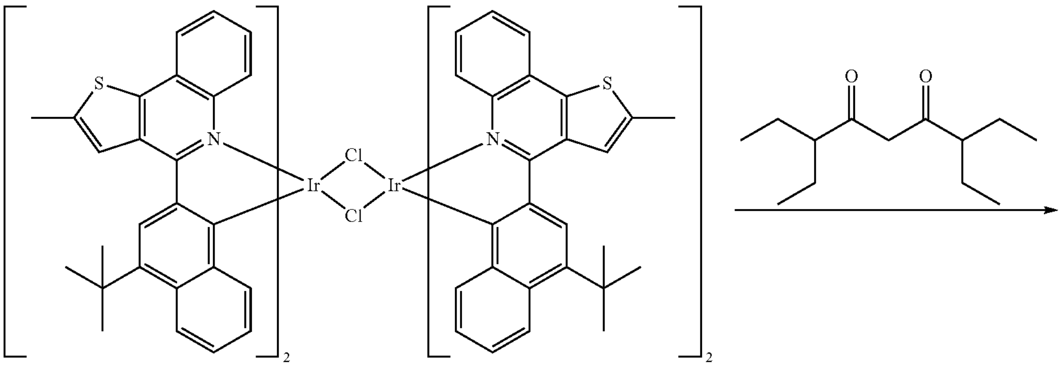

C27

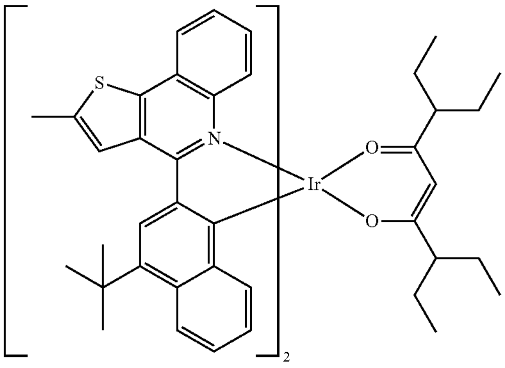

Compound 177

Preparation of Compound C27

The compound C27 (4.7 g, yield 48%) was obtained in the same manner as in the preparation method of the compound C2, except that B2 (9 g, 24.63 mmol) and $IrCl_3 \cdot H_2Ox$ (4.3 g, 11.19 mmol) were replaced with B27 (8.4 g, 22 mmol) and $IrCl_3 \cdot H_2Ox$ (3.5 g, 10 mmol).

Preparation of Compound 177

The compound 177 (3.1 g, yield 55%) was obtained in the same manner as in the preparation method of the compound 42, except that C2 (4.9 g, 2.56 mmol) and 3,7-diethylnonane-4,6-dione (5.3 g, 24.98 mmol) and $Na_2CO_3$ (5.3 g, 49.92 mmol) were replaced with C27 (4.7 g, 2.40 mmol) and 3,7-diethylnonane-4,6-dione (5.1 g, 24.00 mmol) and $Na_2CO_3$ (5.1 g, 48 mmol).

MS (m/z): 1164.43

<Preparation of Compound 211>

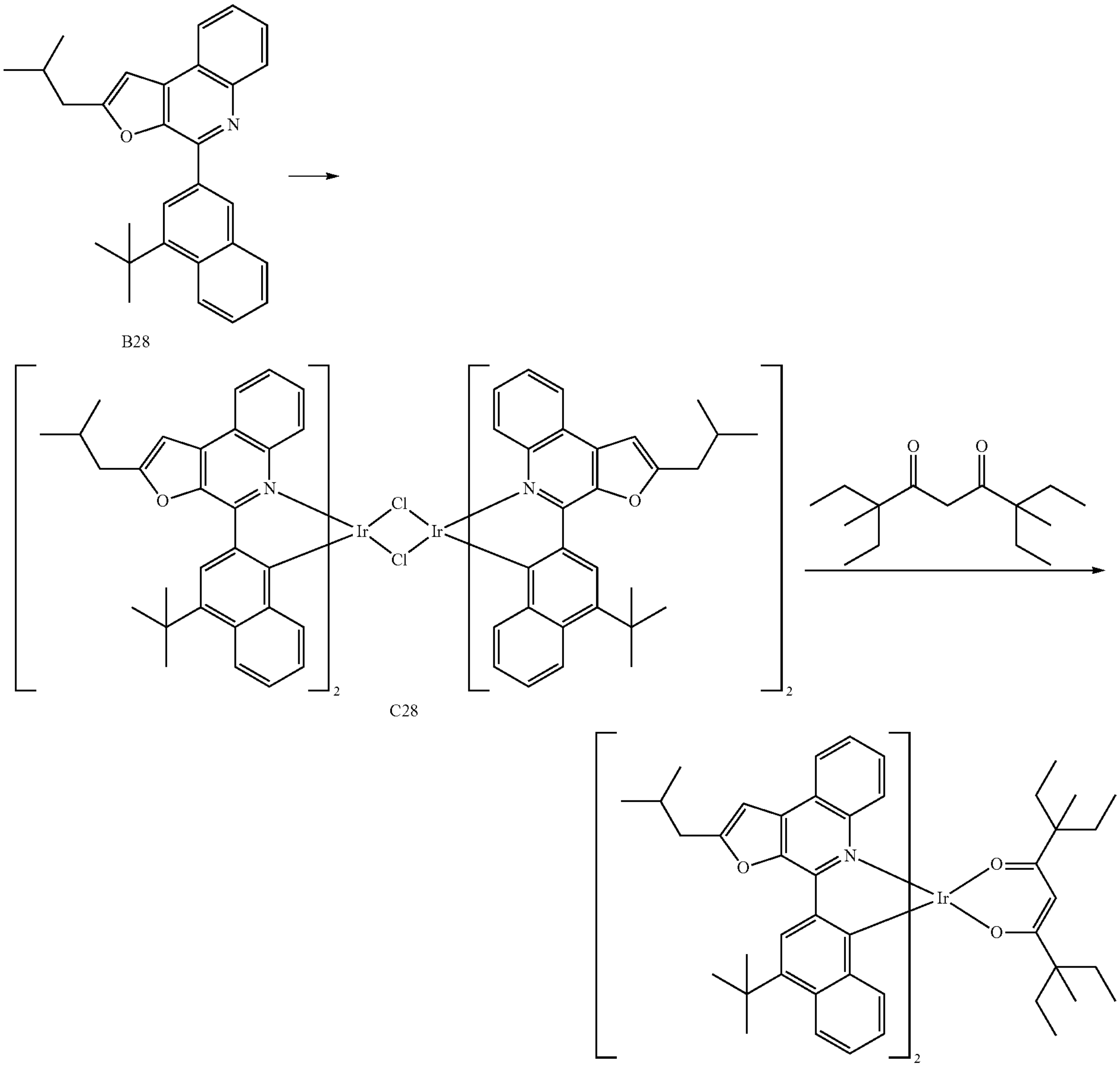

B28

C28

Compound 211

Preparation of Compound C28

The compound C28 (4.6 g, yield 44%) was obtained in the same manner as in the preparation method of the compound C2 except for using B28 (9.0 g, 22 mmol) and $IrCl_3 \cdot H_2Ox$ (3.5 g, 10 mmol) instead of B2 (9 g, 24.63 mmol) and $IrCl_3 \cdot H_2Ox$ (4.3 g, 11.19 mmol) to obtain Preparation of Compound 211

The compound 211 (3.4 g, yield) 62%) was obtained in the same manner as in the preparation method of the compound 42, except that C2 (4.9 g, 2.56 mmol) and 3,7-diethylnonane-4,6-dione (5.3 g, 24.98 mmol) and $Na_2CO_3$ (5.3 g, 49.92 mmol) were replaced with C28 (4.6 g, 2.20 mmol) and 3,7-diethyl-3,7-dimethylnonane-4,6-dione (5.3 g, 22.00 mmol) and $Na_2CO_3$ (4.7 g, 44 mmol).

MS (n/z): 1244.60

<Preparation of Compound 245>

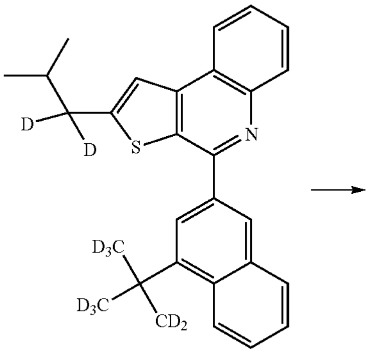

B29

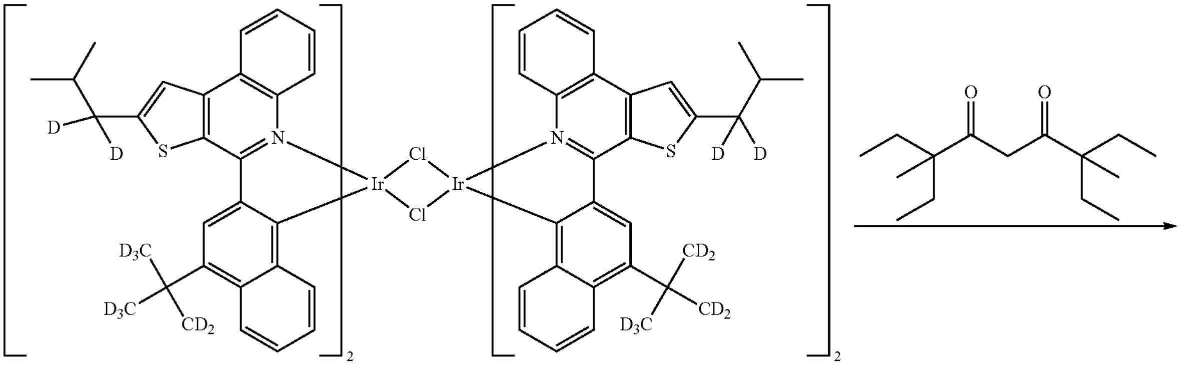

C29

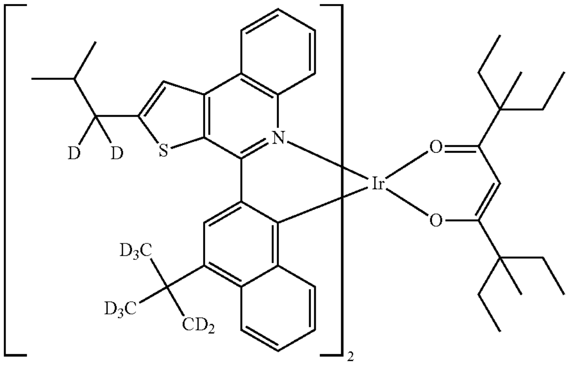

Compound 245

Preparation of Compound C29

The compound C29 (5.1 g, yield 47%) was obtained in the same manner as in the preparation method of the compound C2 except that B2 (9 g, 24.63 mmol) and $IrCl_3 \cdot H_2Ox$ (4.3 g, 11.19 mmol) were replaced with B29 (9.6 g, 22 mmol) and $IrCl_3 \cdot H_2Ox$ (3.5 g, 10 mmol)

Preparation of Compound 245

The compound 245 (3.7 g, yield) 60%) was obtained in the same manner as in the preparation method of the compound 42, except that C2 (4.9 g, 2.56 mmol) and 3,7-diethylnonane-4,6-dione (5.3 g, 24.98 mmol) and $Na_2CO_3$ (5.3 g, 49.92 mmol) were replaced with C29 (5.1 g, 2.35 mmol) and 3,7-diethyl-3,7-dimethylnonane-4,6-dione (5.6 g, 23.50 mmol) and $Na_2CO_3$ (5.0 g, 47 mmol).

MS (m/z): 1298.69

EXAMPLES

Present Example 1

A glass substrate having a thin film made of ITO (indium tin oxide) of a thickness of 1,000 Å coated thereon was washed and was subjected to ultrasonic cleaning using a solvent such as isopropyl alcohol, acetone, or methanol and was dried.

HI-1 as a hole injection material of a thickness of 60 nm was formed on the prepared ITO transparent electrode via thermal vacuum deposition. NPB as a hole transport material was thermally vacuum deposited to have a thickness of 80 nm on the hole injection layer. A light-emitting layer was thermally vacuum deposited on the hole transport material. In this regard, the light-emitting layer contains CBP as a host material and the compound 5 as the dopant. A doping concentration was 5% and a thickness of the light emission layer was 30 nm. ET-1:Liq (1:1) (30 nm) as materials for the electron transport layer and the electron injection layer was thermally vacuum deposited on the light-emitting layer. Then, 100 nm thick aluminum was deposited thereon to form a negative electrode. Thus, an organic electroluminescent device was fabricated. The materials used in above Present Example 1 are as follow.

Hi-1

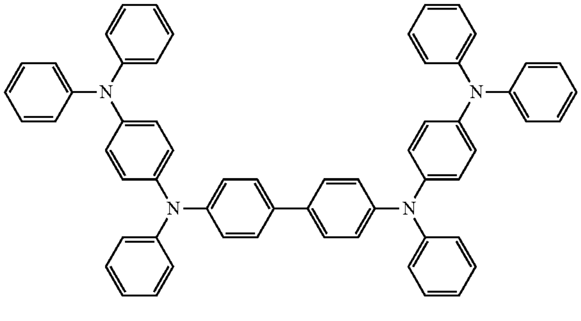

-continued

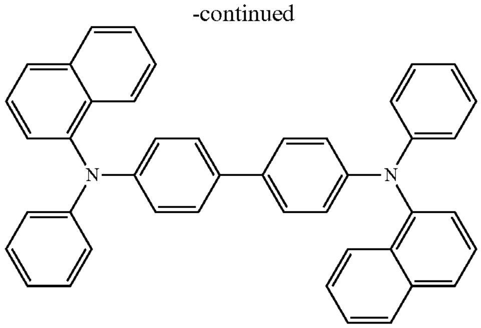

NPB

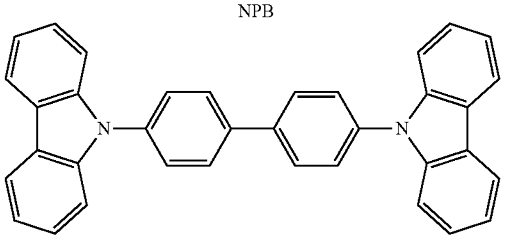

CBP

ET-1

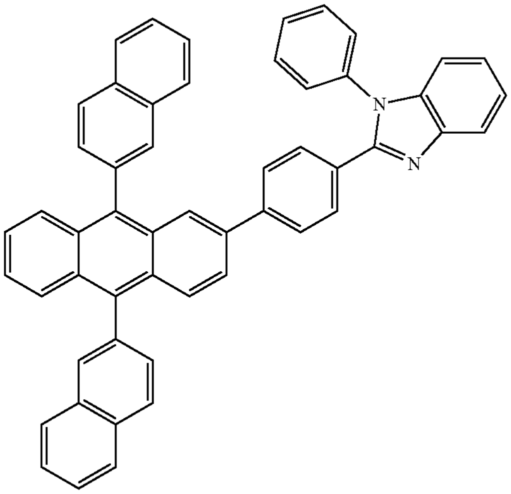

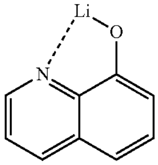

Liq

In this regard, HI-1 is NPNPB and ET-1 is ZADN.

Present Example 2

An organic electroluminescent device was fabricated in the same manner as in above Present Example 1 except that the compound 7 was used instead of the compound 5 in above Present Example 1.

Present Example 3

An organic electroluminescent device was fabricated in the same manner as in above Present Example 1, except that the compound 8 was used instead of the compound 5 in above Present Example 1.

Present Example 4

An organic electroluminescent device was fabricated in the same manner as in above Present Example 1, except that the compound 10 was used instead of the compound 5 in above Present Example 1.

Present Example 5

An organic electroluminescent device was fabricated in the same manner as in above Present Example 1, except that the compound 11 was used instead of the compound 5 in above Present Example 1.

Present Example 6

An organic electroluminescent device was fabricated in the same manner as in above Present Example 1, except that the compound 15 was used instead of the compound 5 in above Present Example 1.

Present Example 7

An organic electroluminescent device was fabricated in the same manner as in above Present Example 1, except that the compound 16 was used instead of the compound 5 in above Present Example 1.

Present Example 8

An organic electroluminescent device was manufactured in the same manner as in above Present Example 1, except that the compound 19 was used instead of the compound 5 in above Present Example 1.

Present Example 9

An organic electroluminescent device was fabricated in the same manner as in above Present Example 1, except that the compound 21 was used instead of the compound 5 in above Present Example 1.

Present Example 10

An organic electroluminescent device was fabricated in the same manner as in above Present Example 1, except that the compound 28 was used instead of the compound 5 in above Present Example 1.

Present Example 11

An organic electroluminescent device was fabricated in the same manner as in above Present Example 1, except that the compound 32 was used instead of the compound 5 in above Present Example 1.

Present Example 12

An organic electroluminescent device was fabricated in the same manner as in above Present Example 1, except that the compound 42 was used instead of the compound 5 in above Present Example 1.

Present Example 13

An organic electroluminescent device was fabricated in the same manner as in above Present Example 1, except that the compound 83 was used instead of the compound 5 in above Present Example 1.

Present Example 14

An organic electroluminescent device was manufactured in the same manner as in above Present Example 1, except that the compound 115 was used instead of the compound 5 in above Present Example 1.

Present Example 15

An organic electroluminescent device was fabricated in the same manner as in above Present Example 1 except that the compound 131 was used instead of the compound 5 in above Present Example 1.

Present Example 16

An organic electroluminescent device was fabricated in the same manner as in above Present Example 1, except that the compound 135 was used instead of the compound 5 in above Present Example 1.

Present Example 17

An organic electroluminescent device was manufactured in the same manner as in above Present Example 1, except that the compound 136 was used instead of the compound 5 in above Present Example 1.

Present Example 18

An organic electroluminescent device was fabricated in the same manner as in above Present Example 1, except that the compound 138 was used instead of the compound 5 in above Present Example 1.

Present Example 19

An organic electroluminescent device was fabricated in the same manner as in above Present Example 1 except that the compound 139 was used instead of the compound 5 in above Present Example 1.

Present Example 20

An organic electroluminescent device was manufactured in the same manner as in above Present Example 1, except that the compound 143 was used instead of the compound 5 in above Present Example 1.

Present Example 21

An organic electroluminescent device was fabricated in the same manner as in above Present Example 1 except that the compound 144 was used instead of the compound 5 in above Present Example 1.

Present Example 22

An organic electroluminescent device was fabricated in the same manner as in above Present Example 1, except that the compound 145 was used instead of the compound 5 in above Present Example 1.

Present Example 23

An organic electroluminescent device was fabricated in the same manner as in above Present Example 1, except that the compound 147 was used instead of the compound 5 in above Present Example 1.

Present Example 24

An organic electroluminescent device was fabricated in the same manner as in above Present Example 1, except that the compound 149 was used instead of the compound 5 in above Present Example 1.

Present Example 25

An organic electroluminescent device was fabricated in the same manner as in above Present Example 1, except that the compound 156 was used instead of the compound 5 in above Present Example 1.

Present Example 26

An organic electroluminescent device was manufactured in the same manner as in above Present Example 1 except that the compound 160 was used instead of the compound 5 in above Present Example 1.

Present Example 27

An organic electroluminescent device was fabricated in the same manner as in above Present Example 1, except that the compound 177 was used instead of the compound 5 in above Present Example 1.

Present Example 28

An organic electroluminescent device was fabricated in the same manner as in above Present Example 1 except that the compound 211 was used instead of the compound 5 in above Present Example 1.

Present Example 29

An organic electroluminescent device was fabricated in the same manner as in above Present Example 1, except that the compound 245 was used instead of the compound 5 in above Present Example 1.

Present Example 30

An organic electroluminescent device was fabricated in the same manner as in above Present Example 1, except that the compound 257 was used instead of the compound 5 in above Present Example 1.

Present Example 31

An organic electroluminescent device was fabricated in the same manner as in above Present Example 1, except that the compound 258 was used instead of the compound 5 in above Present Example 1.

Present Example 32

An organic electroluminescent device was fabricated in the same manner as in above Present Example 1, except that the compound 259 was used instead of the compound 5 in above Present Example 1.

Present Example 33

An organic electroluminescent device was fabricated in the same manner as in above Present Example 1, except that the compound 260 was used instead of the compound 5 in above Present Example 1.

Present Example 34

An organic electroluminescent device was fabricated in the same manner as in above Present Example 1, except that the compound 261 was used instead of the compound 5 in above Present Example 1.

Present Example 35

An organic electroluminescent device was fabricated in the same manner as in above Present Example 1, except that the compound 262 was used instead of the compound 5 in above Present Example 1.

Present Example 36

An organic electroluminescent device was fabricated in the same manner as in above Present Example 1, except that the compound 263 was used instead of the compound 5 in above Present Example 1.

Present Example 37

An organic electroluminescent device was fabricated in the same manner as in above Present Example 1, except that the compound 264 was used instead of the compound 5 in above Present Example 1.

Present Example 38

An organic electroluminescent device was fabricated in the same manner as in above Present Example 1, except that the compound 265 was used instead of the compound 5 in above Present Example 1.

Present Example 39

An organic electroluminescent device was fabricated in the same manner as in above Present Example 1, except that the compound 266 was used instead of the compound 5 in above Present Example 1.

Present Example 40

An organic electroluminescent device was fabricated in the same manner as in above Present Example 1, except that the compound 267 was used instead of the compound 5 in above Present Example 1.

Present Example 41

An organic electroluminescent device was fabricated in the same manner as in above Present Example 1, except that the compound 268 was used instead of the compound 5 in above Present Example 1.

Present Example 42

An organic electroluminescent device was fabricated in the same manner as in above Present Example 1, except that the compound 269 was used instead of the compound 5 in above Present Example 1.

Present Example 43

An organic electroluminescent device was fabricated in the same manner as in above Present Example 1, except that the compound 270 was used instead of the compound 5 in above Present Example 1.

Present Example 44

An organic electroluminescent device was fabricated in the same manner as in above Present Example 1, except that the compound 271 was used instead of the compound 5 in above Present Example 1.

Present Example 45

An organic electroluminescent device was fabricated in the same manner as in above Present Example 1, except that the compound 272 was used instead of the compound 5 in above Present Example 1.

Present Example 46

An organic electroluminescent device was fabricated in the same manner as in above Present Example 1, except that the compound 273 was used instead of the compound 5 in above Present Example 1.

Present Example 47

An organic electroluminescent device was fabricated in the same manner as in above Present Example 1, except that the compound 274 was used instead of the compound 5 in above Present Example 1.

Present Example 48

An organic electroluminescent device was fabricated in the same manner as in above Present Example 1, except that the compound 275 was used instead of the compound 5 in above Present Example 1.

Present Example 49

An organic electroluminescent device was fabricated in the same manner as in above Present Example 1, except that the compound 276 was used instead of the compound 5 in above Present Example 1.

Present Example 50

An organic electroluminescent device was fabricated in the same manner as in above Present Example 1, except that the compound 277 was used instead of the compound 5 in above Present Example 1.

Present Example 51

An organic electroluminescent device was fabricated in the same manner as in above Present Example 1, except that the compound 278 was used instead of the compound 5 in above Present Example 1.

Present Example 52

An organic electroluminescent device was fabricated in the same manner as in above Present Example 1, except that the compound 279 was used instead of the compound 5 in above Present Example 1.

Present Example 53

An organic electroluminescent device was fabricated in the same manner as in above Present Example 1, except that the compound 280 was used instead of the compound 5 in above Present Example 1.

Present Example 54

An organic electroluminescent device was fabricated in the same manner as in above Present Example 1, except that the compound 281 was used instead of the compound 5 in above Present Example 1.

Present Example 55

An organic electroluminescent device was fabricated in the same manner as in above Present Example 1, except that the compound 282 was used instead of the compound 5 in above Present Example 1.

Present Example 56

An organic electroluminescent device was fabricated in the same manner as in above Present Example 1, except that the compound 283 was used instead of the compound 5 in above Present Example 1.

Present Example 57

An organic electroluminescent device was fabricated in the same manner as in above Present Example 1, except that the compound 284 was used instead of the compound 5 in above Present Example 1.

Present Example 58

An organic electroluminescent device was fabricated in the same manner as in above Present Example 1, except that the compound 285 was used instead of the compound 5 in above Present Example 1.

Present Example 59

An organic electroluminescent device was fabricated in the same manner as in above Present Example 1, except that the compound 286 was used instead of the compound 5 in above Present Example 1.

Present Example 60

An organic electroluminescent device was fabricated in the same manner as in above Present Example 1, except that the compound 287 was used instead of the compound 5 in above Present Example 1.

Present Example 61

An organic electroluminescent device was fabricated in the same manner as in above Present Example 1, except that the compound 288 was used instead of the compound 5 in above Present Example 1.

Present Example 62

An organic electroluminescent device was fabricated in the same manner as in above Present Example 1, except that the compound 289 was used instead of the compound 5 in above Present Example 1.

Present Example 63

An organic electroluminescent device was fabricated in the same manner as in above Present Example 1, except that the compound 290 was used instead of the compound 5 in above Present Example 1.

Present Example 64

An organic electroluminescent device was fabricated in the same manner as in above Present Example 1, except that the compound 291 was used instead of the compound 5 in above Present Example 1.

Comparative Example 1

An organic electroluminescent device was fabricated in the same manner as in above Present Example 1, except that RD having a following structure was used instead of the compound 5 in above Present Example 1.

RD

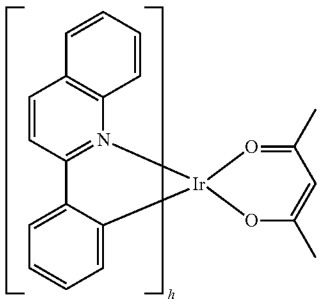

EXPERIMENTAL EXAMPLES

Each of the organic electroluminescent devices prepared in Present Examples 1 to 64 and Comparative Example 1, respectively, was connected to an external power source, and the organic electroluminescent device characteristics were evaluated at room temperature using a current source and a photometer.

Specifically, a driving voltage, external quantum efficiency (EQE), lifespan characteristics (LT95), a full width at half maximum (FWHM), and an aspect ratio were measured under a current of 10 mA/cm$^2$, and the results are shown in Table 1 and Table 2 below.

The aspect ratio was calculated as (molecular dimension in long axis direction (N-Metal-N direction) centered on metal)/(molecular dimension in short axis direction perpendicular to long axis direction centered on metal) and was determined based on a calculating result of a distance between atoms in the molecule using a Gaussian molecular calculation program (Gaussian 16).

LT95 lifetime refers to a time it takes for a display element to lose 5% of initial brightness thereof. The LT95 lifetime is the most difficult customer specification to meet, and determines whether the display will experience image burn-in.

Figure 3:
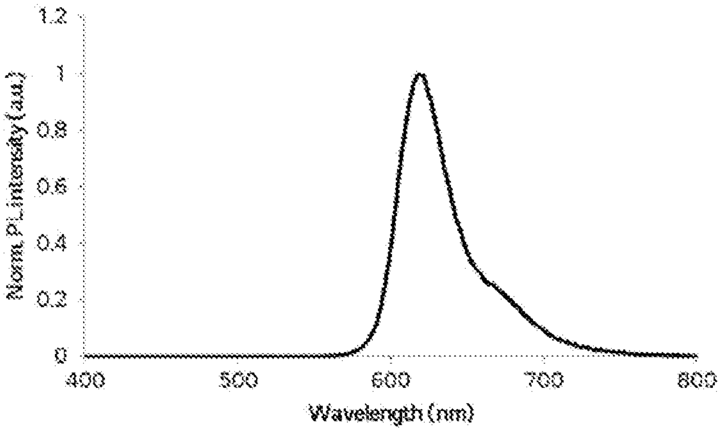
FIG. 3 and FIG. 4 are respectively graphs plotting emission wavelengths and FWHMs (full width at half maximum) of organic electroluminescent devices to which a compound 42 of Present Example 12 and a compound 145 of Present Example 22 of the present disclosure are respectively applied, wherein a vertical axis indicates photoluminescence (PL) intensity, and a horizontal axis indicates a wavelength (nm).
Figure 4:
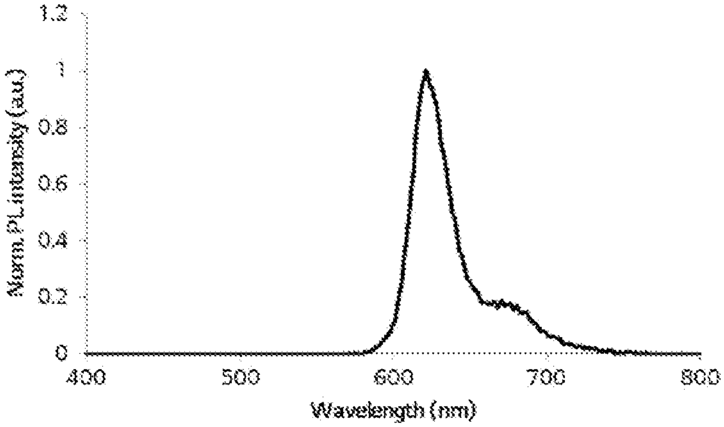

The full Width at Half Maximum (FWHM) means a wavelength width corresponding to ½ of the maximum value of a curve (kr) representing a wavelength (see FIG. 3 and FIG. 4). A narrow FWHM means that a range of colors that can be rendered is wide, and thus means that colors closer to natural colors can be realized and color gamut is improved.

The full width at half maximum (FWHM) was evaluated based on photoluminescence (PL) intensity measurement, and a Model/Maker of the measuring equipment is FS-5/Edinburgh Instruments.

TABLE 1

| | Dopant | Drive voltage (%, relative value) | EQE (%, relative value) | LT95 (%, relative value) | FWHM (%, relative value) | Aspect ratio (%, relative value) |
|---|---|---|---|---|---|---|
| Comparative Example 1 | Compound RD | 100 | 100 | 100 | 100 | 100 |
| Present Example 1 | Compound 5 | 97 | 109 | 115 | 75 | 130 |
| Present Example 2 | Compound 7 | 99 | 103 | 101 | 77 | 134 |
| Present Example 3 | Compound 8 | 98 | 115 | 109 | 72 | 121 |
| Present Example 4 | Compound 10 | 97 | 127 | 128 | 72 | 104 |

TABLE 1-continued

| | Dopant | Drive voltage (%, relative value) | EQE (%, relative value) | LT95 (%, relative value) | FWHM (%, relative value) | Aspect ratio (%, relative value) |
|---|---|---|---|---|---|---|
| Present Example 5 | Compound 11 | 97 | 133 | 135 | 70 | 104 |
| Present Example 6 | Compound 15 | 96 | 139 | 109 | 80 | 130 |
| Present Example 7 | Compound 16 | 96 | 145 | 103 | 83 | 120 |
| Present Example 8 | Compound 19 | 97 | 145 | 154 | 67 | 154 |
| Present Example 9 | Compound 21 | 97 | 145 | 179 | 67 | 154 |
| Present Example 10 | Compound 28 | 98 | 152 | 160 | 65 | 154 |
| Present Example 11 | Compound 32 | 96 | 115 | 141 | 78 | 124 |
| Present Example 12 | Compound 42 | 96 | 121 | 122 | 72 | 104 |
| Present Example 13 | Compound 83 | 97 | 152 | 147 | 65 | 154 |
| Present Example 14 | Compound 115 | 97 | 145 | 145 | 65 | 154 |
| Present Example 15 | Compound 131 | 95 | 133 | 154 | 58 | 116 |
| Present Example 16 | Compound 135 | 97 | 127 | 128 | 60 | 135 |
| Present Example 17 | Compound 136 | 96 | 139 | 141 | 58 | 113 |
| Present Example 18 | Compound 138 | 95 | 142 | 167 | 55 | 102 |
| Present Example 19 | Compound 139 | 95 | 145 | 173 | 55 | 101 |
| Present Example 20 | Compound 143 | 94 | 164 | 141 | 63 | 115 |
| Present Example 21 | Compound 144 | 94 | 170 | 128 | 67 | 108 |
| Present Example 22 | Compound 145 | 94 | 152 | 179 | 50 | 106 |
| Present Example 23 | Compound 147 | 95 | 170 | 186 | 48 | 135 |
| Present Example 24 | Compound 149 | 95 | 170 | 212 | 48 | 135 |
| Present Example 25 | Compound 156 | 96 | 176 | 192 | 48 | 135 |
| Present Example 26 | Compound 160 | 94 | 139 | 173 | 62 | 106 |
| Present Example 27 | Compound 177 | 94 | 145 | 171 | 50 | 107 |
| Present Example 28 | Compound 211 | 96 | 167 | 174 | 47 | 135 |
| Present Example 29 | Compound 245 | 96 | 164 | 203 | 47 | 139 |

TABLE 2

| | Dopant | Drive voltage (%, relative value) | EQE (%, relative value) | LT95 (%, relative value) | FWHM (%, relative value) | Aspect ratio (%, relative value) |
|---|---|---|---|---|---|---|
| Comparative Example 1 | Compound RD | 100 | 100 | 100 | 100 | 100 |
| Present Example 30 | Compound 257 | 94 | 174 | 188 | 48 | 135 |
| Present Example 31 | Compound 258 | 95 | 180 | 192 | 48 | 135 |
| Present Example 32 | Compound 259 | 96 | 182 | 194 | 46 | 135 |
| Present Example 33 | Compound 260 | 94 | 175 | 190 | 49 | 128 |
| Present Example 34 | Compound 261 | 95 | 181 | 193 | 47 | 135 |
| Present Example 35 | Compound 262 | 95 | 183 | 195 | 47 | 140 |

TABLE 2-continued

| | Dopant | Drive voltage (%, relative value) | EQE (%, relative value) | LT95 (%, relative value) | FWHM (%, relative value) | Aspect ratio (%, relative value) |
|---|---|---|---|---|---|---|
| Present Example 36 | Compound 263 | 95 | 185 | 196 | 47 | 140 |
| Present Example 37 | Compound 264 | 96 | 187 | 198 | 46 | 128 |
| Present Example 38 | Compound 265 | 93 | 168 | 165 | 49 | 108 |
| Present Example 39 | Compound 266 | 95 | 172 | 175 | 49 | 130 |
| Present Example 40 | Compound 267 | 93 | 166 | 160 | 49 | 110 |
| Present Example 41 | Compound 268 | 95 | 181 | 220 | 48 | 135 |
| Present Example 42 | Compound 269 | 95 | 182 | 225 | 48 | 135 |
| Present Example 43 | Compound 270 | 95 | 183 | 240 | 48 | 135 |
| Present Example 44 | Compound 271 | 95 | 183 | 230 | 48 | 135 |
| Present Example 45 | Compound 272 | 95 | 179 | 194 | 47 | 125 |
| Present Example 46 | Compound 273 | 96 | 181 | 177 | 48 | 132 |
| Present Example 47 | Compound 274 | 96 | 178 | 168 | 49 | 133 |
| Present Example 48 | Compound 275 | 95 | 178 | 188 | 48 | 135 |
| Present Example 49 | Compound 276 | 95 | 183 | 195 | 46 | 135 |
| Present Example 50 | Compound 277 | 94 | 188 | 160 | 56 | 146 |
| Present Example 51 | Compound 278 | 94 | 190 | 165 | 55 | 146 |
| Present Example 52 | Compound 279 | 94 | 190 | 163 | 55 | 135 |
| Present Example 53 | Compound 280 | 94 | 192 | 168 | 54 | 135 |
| Present Example 54 | Compound 281 | 93 | 195 | 145 | 60 | 140 |
| Present Example 55 | Compound 282 | 93 | 197 | 150 | 59 | 140 |
| Present Example 56 | Compound 283 | 95 | 175 | 180 | 48 | 137 |
| Present Example 57 | Compound 284 | 95 | 177 | 182 | 48 | 137 |
| Present Example 58 | Compound 285 | 96 | 179 | 184 | 47 | 131 |
| Present Example 59 | Compound 286 | 96 | 177 | 195 | 47 | 135 |
| Present Example 60 | Compound 287 | 96 | 179 | 190 | 47 | 129 |
| Present Example 61 | Compound 288 | 96 | 174 | 187 | 47 | 129 |
| Present Example 62 | Compound 289 | 96 | 173 | 188 | 48 | 133 |
| Present Example 63 | Compound 290 | 93 | 171 | 186 | 58 | 135 |
| Present Example 64 | Compound 291 | 93 | 172 | 181 | 59 | 133 |

RD as the dopant compound of the light-emitting layer in Comparative Example 1 of the present disclosure has a structural difference from the compound represented by the Chemical Formula I in Present Example of the present disclosure in that no additional fused ring is introduced to 2-phenylquinoline.

As can be identified from the results in Table 1 and Table 2, the organic electroluminescent device in which the organometallic compound used in each of Present Examples 1 to 64 of the present disclosure is used as the dopant of the light-emitting layer has lowered driving voltage, improved external quantum Efficiency (EQE) and lifespan (LT95), and improved color purity due to the narrow full width at half maximum (FWHM), compared to Comparative Example 1.

A scope of protection of the present disclosure should be construed by the scope of the claims, and all technical ideas within the scope equivalent thereto should be construed as being included in the scope of the present disclosure. Although the embodiments of the present disclosure have been described in more detail with reference to the accompanying drawings, the present disclosure is not necessarily limited to these embodiments. The present disclosure can be implemented in various modified manners within the scope not departing from the technical idea of the present disclosure. Accordingly, the embodiments disclosed in the resent disclosure are not intended to limit the technical idea of the present disclosure, but to describe the present disclosure. the scope of the technical idea of the present disclosure is not limited by the embodiments. Therefore, it should be understood that the embodiments as described above are illustrative and non-limiting in all respects. The scope of protection of the present disclosure should be interpreted by the claims, and all technical ideas within the scope of the present disclosure should be interpreted as being included in the scope of the present disclosure.

What is claimed is:

1. An organometallic compound represented by one of the following compounds:

42

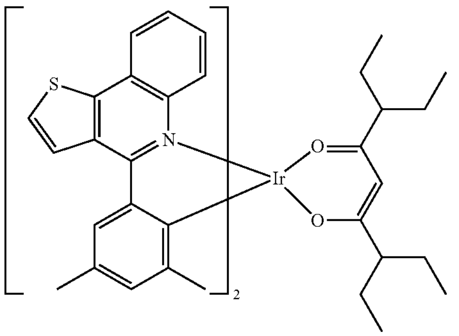

145

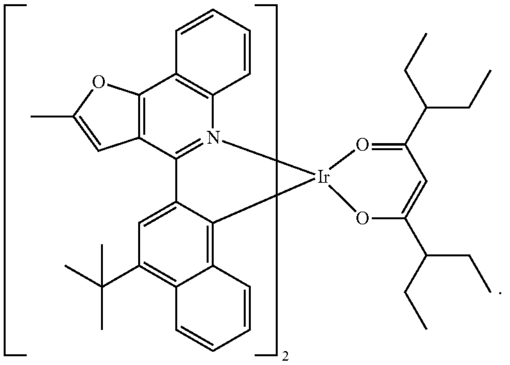

2. The organometallic compound of claim 1, wherein the compound is used as a red phosphorescent material or a green phosphorescent material.

3. An organic electroluminescent device comprising:

a first electrode;

a second electrode facing the first electrode; and an organic layer disposed between the first electrode and the second electrode, wherein the organic layer includes a light-emitting layer, and wherein the light-emitting layer contains the organometallic compound according to claim 1.

4. The organic electroluminescent device of claim 3, wherein the organometallic compound is used as dopant of the light-emitting layer.

5. The organic electroluminescent device of claim 3, wherein the organic layer further includes at least one selected from a group consisting of a hole injection layer, a hole transport layer, an electron transport layer and an electron injection layer.

6. An organic light-emitting display device comprising:

a substrate;

a driving element positioned on the substrate; and an organic light-emitting element disposed on the substrate and connected to the driving element, wherein the organic light-emitting element includes the organic electroluminescent device according to claim 3.

7. The organic electroluminescent device of claim 3, wherein the organic layer is formed by sequentially stacking a hole injection layer, a hole transport layer, a light emission layer, an electron transport layer and an electron injection layer on the first electrode.

8. The organic electroluminescent device of claim 7, wherein the hole injection layer comprises a compound selected from a group consisting of MTDATA, CuPc, TCTA, NPB(NPD), HATCN, TDAPB, PEDOT/PSS, N-(biphenyl-4-yl)-9,9-dimethyl-N-(4-(9-phenyl-9H-carbazol-3-yl)phenyl)-9H-fluoren-2-amine, and NPNPB (N,N'-diphenyl-N,N'-di[4-(N,N-diphenyl-amino)phenyl]benzidine).

9. The organic electroluminescent device of claim 7, wherein the hole transport layer comprises a compound selected from a group consisting of TPD, NPD, CBP, N-(biphenyl-4-yl)-9,9-dimethyl-N-(4-(9-phenyl-9H-carbazol-3-yl)phenyl)-9H-fluoren-2-amine, and N-(biphenyl-4-yl)-N-(4-(9-phenyl-9H-carbazol-3-yl)phenyl)biphenyl)-4-amine.

10. The organic electroluminescent device of claim 4, wherein the light-emitting layer includes a host and the organometallic compound as dopant, and wherein the host material is selected from a group consisting of CBP (carbazole biphenyl), and mCP (1,3-bis(carbazol-9-yl).

11. The organic electroluminescent device of claim 5, wherein the electron transport layer and the electron injection layer are sequentially stacked between the light-emitting layer and the second electrode.

12. The organic electroluminescent device of claim 5, wherein the electron transport layer comprises a compound selected from a group consisting of Alq3 (tris(8-hydroxyquinolino)aluminum), Liq (8-hydroxyquinolinolatolithium), PBD (2-(4-biphenylyl)-5-(4-tert-butylphenyl)-1,3,4oxadiazole), TAZ (3-(4-biphenyl)4-phenyl-5-tert-butylphenyl-1,2,4-triazole), spiro-PBD, BAlq (bis(2-methyl-8-quinolinolate)-4-(phenylphenolato)aluminium), SAlq, TPBi (2,2',2-(1,3,5-benzinetriyl)-tris(1-phenyl-1-H-benzimidazole), oxadiazole, triazole, phenanthroline, benzoxazole, benzthiazole, and ZADN (2-[4-(9,10-Di-naphthalen-2-yl-anthracen-2-yl)-phenyl]-1-phenyl-1H-benzoimidazole).

13. The organic electroluminescent device of claim 5, wherein the electron injection layer comprises a compound selected from a group consisting of Alq3 (tris(8-hydroxyquinolino)aluminum), PBD, TAZ, spiro-PBD, BAlq, and SAlq.

14. The organic electroluminescent device of claim 5, wherein the electron injection layer comprises a metal compound selected from the group consisting of Liq, LiF, NaF, KF, RbF, CsF, FrF, $BeF_2$, $MgF_2$, $CaF_2$, $SrF_2$, $BaF_2$ and $RaF_2$.

15. The organic electroluminescent device of claim 5, wherein the organic electroluminescent device has a tandem structure comprising two light-emitting stacks.

16. The organic electroluminescent device of claim 5, wherein the organic electroluminescent device has a tandem structure comprising three light-emitting stacks.

* * * * *